United States Patent
Gotoda et al.

(10) Patent No.: US 9,334,239 B2
(45) Date of Patent: May 10, 2016

(54) AMORPHOUS FORM OF QUINOLINE DERIVATIVE, AND METHOD FOR PRODUCING SAME

(71) Applicant: Eisai R&D Management Co., Ltd., Tokyo (JP)

(72) Inventors: Masaharu Gotoda, Tsukuba (JP); Kenshi Yoshida, Tsukuba (JP); Nao Shibuguchi, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 14/438,366

(22) PCT Filed: Dec. 19, 2013

(86) PCT No.: PCT/JP2013/084052
§ 371 (c)(1),
(2) Date: Apr. 24, 2015

(87) PCT Pub. No.: WO2014/098176
PCT Pub. Date: Jun. 26, 2014

(65) Prior Publication Data
US 2015/0291532 A1 Oct. 15, 2015

(30) Foreign Application Priority Data

Dec. 21, 2012 (JP) ................................. 2012-279158

(51) Int. Cl.
*C07D 215/48* (2006.01)
(52) U.S. Cl.
CPC ........... *C07D 215/48* (2013.01); *C07B 2200/13* (2013.01)
(58) Field of Classification Search
CPC .......................... C07D 215/48; C07B 2200/13
See application file for complete search history.

(56) References Cited

U.S. PATENT DOCUMENTS

| | | |
|---|---|---|
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |
| 6,596,311 B1 | 7/2003 | Dobetti et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,074,880 B2 | 7/2006 | Rhine et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,211,587 B2 | 5/2007 | Kubo et al |
| 7,253,286 B2 | 8/2007 | Funahashi et al. |

(Continued)

FOREIGN PATENT DOCUMENTS

| | | |
|---|---|---|
| CA | 2 361 057 | 7/2000 |
| CH | 656535 | 7/1986 |

(Continued)

OTHER PUBLICATIONS

International Search Report for PCT/JP2013/084052 dated Mar. 4, 2014.
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium and Beruf, DT. Apotheker-Verl, Stuttgart; DE, Jan. 1, 2000, p. 40-p. 52, XP008143620 (English translation).

(Continued)

*Primary Examiner* — D M Seaman
(74) *Attorney, Agent, or Firm* — Fish & Richardson P.C.

(57) ABSTRACT

The invention provides an amorphous form of 4-(3-chloro-4-(cyclopropylaminocarbonyl)aminophenoxy)-7-methoxy-6-quinolinecarboxamide.

23 Claims, 2 Drawing Sheets

(56) References Cited

U.S. PATENT DOCUMENTS

| | | |
|---|---|---|
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,725,303 B2 | 5/2010 | Tramontana |
| 7,759,518 B2 | 7/2010 | Maderna et al. |
| 7,790,885 B2 | 9/2010 | Nagai et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,994,159 B2 | 8/2011 | Yamamoto et al. |
| 7,998,948 B2 | 8/2011 | Hiroshi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,492,560 B2 | 7/2013 | Stokes et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2007/0298111 A1 | 12/2007 | Ueki |
| 2008/0207617 A1 | 8/2008 | Miwa et al. |
| 2008/0214604 A1 | 9/2008 | Furitsu et al. |
| 2008/0241835 A1 | 10/2008 | Mehraban et al. |
| 2008/0286282 A1 | 11/2008 | Semba et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0202541 A1 | 8/2009 | Bruns et al. |
| 2009/0209580 A1 | 8/2009 | Matsui |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0020410 A1 | 1/2011 | Nonomura et al. |
| 2011/0060049 A1 | 3/2011 | Vernier et al. |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0207756 A1 | 8/2011 | Matsui |
| 2011/0293615 A1 | 12/2011 | Yamamoto |
| 2012/0022076 A1 | 1/2012 | Maderna et al. |
| 2012/0053177 A1 | 3/2012 | Ibrahim et al. |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0085152 A1 | 4/2013 | Matsui et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CN | 1293041 | 5/2001 |
| CN | 1473041 | 2/2004 |
| CN | 1478078 | 2/2004 |
| CN | 1634043 | 7/2005 |
| CN | 1772052 | 5/2006 |
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454286 | 6/2009 |
| CN | 101454311 | 6/2009 |
| CN | 101616671 | 12/2009 |
| CN | 102470133 | 5/2012 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |
| EP | 0 870 842 | 10/1998 |
| EP | 0 930 305 | 7/1999 |
| EP | 0 930 310 | 7/1999 |
| EP | 1 029 853 | 8/2000 |

(56) References Cited

FOREIGN PATENT DOCUMENTS

| | | |
|---|---|---|
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 473 043 | 11/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 719 763 | 11/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1894918 * | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 058 302 | 5/2009 |
| EP | 2062886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| EP | 2293071 | 3/2011 |
| GB | 2253848 | 9/1992 |
| GB | 2456907 | 8/2009 |
| IL | 148756 | 10/2007 |
| IN | 236500 | 11/2009 |
| JP | 61-148115 | 7/1986 |
| JP | 63-028427 | 6/1988 |
| JP | 1-022874 | 1/1989 |
| JP | H1-22874 | 1/1989 |
| JP | 2-291295 | 12/1990 |
| JP | 4-341454 | 11/1992 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001/131071 | 5/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-033472 | 2/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005/501074 | 1/2005 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-515884 | 6/2006 |
| JP | 2006-230816 | 9/2006 |
| JP | 2007-153894 | 6/2007 |
| JP | 2008-546797 | 12/2008 |
| JP | 2009-132660 | 6/2009 |
| JP | 2010-535233 | 11/2010 |
| KR | 2003-40552 | 5/2003 |
| KR | 10-0589032 | 11/2005 |
| RU | 2328489 | 7/2008 |
| RU | 2362771 | 7/2009 |
| WO | WO 86/03222 | 6/1986 |
| WO | WO 92/20642 | 11/1992 |
| WO | WO 93/11748 | 6/1993 |
| WO | WO 94/09010 | 4/1994 |
| WO | WO 95/15758 | 6/1995 |
| WO | WO 95/17181 | 6/1995 |
| WO | WO 95/19774 | 7/1995 |
| WO | WO 96/09294 | 3/1996 |
| WO | WO 96/26997 | 9/1996 |
| WO | WO 96/30347 | 10/1996 |
| WO | WO 96/33980 | 10/1996 |
| WO | WO 96/39145 | 12/1996 |
| WO | WO 96/40080 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | WO 97/17329 | 5/1997 |
| WO | WO 97/21437 | 6/1997 |
| WO | WO 97/38984 | 10/1997 |
| WO | WO 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | WO 98/13350 | 4/1998 |
| WO | WO 98/14437 | 4/1998 |
| WO | WO 98/23613 | 6/1998 |
| WO | WO 98/29137 | 7/1998 |
| WO | WO 98/32436 | 7/1998 |
| WO | WO 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/35146 | 7/1999 |
| WO | WO 99/43654 | 9/1999 |
| WO | WO 99/62890 | 12/1999 |
| WO | WO 00/19985 | 4/2000 |
| WO | WO 00/31048 | 6/2000 |
| WO | WO 00/42012 | 7/2000 |
| WO | WO 00/43366 | 7/2000 |
| WO | WO 00/43384 | 7/2000 |
| WO | WO 00/44728 | 8/2000 |
| WO | WO 00/47212 | 8/2000 |

(56) References Cited

FOREIGN PATENT DOCUMENTS

| | | |
|---|---|---|
| WO | WO 00/50405 | 8/2000 |
| WO | WO 00/71097 | 11/2000 |
| WO | WO 01/02369 | 1/2001 |
| WO | WO 01/23375 | 4/2001 |
| WO | WO 01/27081 | 4/2001 |
| WO | WO 01/32926 | 5/2001 |
| WO | WO 01/36403 | 5/2001 |
| WO | WO 01/40217 | 6/2001 |
| WO | WO 01/45689 | 6/2001 |
| WO | WO 01/47890 | 7/2001 |
| WO | WO 01/47931 | 7/2001 |
| WO | WO 01/60814 | 8/2001 |
| WO | WO 02/16348 | 2/2002 |
| WO | 02/32872 | 4/2002 |
| WO | WO 02/32872 | 4/2002 |
| WO | WO 02/36117 | 5/2002 |
| WO | WO 02/41882 | 5/2002 |
| WO | WO 02/44156 | 6/2002 |
| WO | WO 02/072578 | 9/2002 |
| WO | WO 02/080975 | 10/2002 |
| WO | WO 02/088110 | 11/2002 |
| WO | WO 02/092091 | 11/2002 |
| WO | WO 02/096361 | 12/2002 |
| WO | WO 03/000660 | 1/2003 |
| WO | WO 03/006462 | 1/2003 |
| WO | WO 03/013529 | 2/2003 |
| WO | WO 03/024386 | 3/2003 |
| WO | WO 03/027102 | 3/2003 |
| WO | WO 03/028711 | 4/2003 |
| WO | WO 03/033472 | 4/2003 |
| WO | WO 03/050090 | 6/2003 |
| WO | WO 03/074045 | 9/2003 |
| WO | WO 03/075840 | 9/2003 |
| WO | WO 03/079020 | 9/2003 |
| WO | WO 03/087026 | 10/2003 |
| WO | WO 03/099771 | 12/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | 2004/080462 | 9/2004 |
| WO | WO 2004/076412 | 9/2004 |
| WO | WO 2004/078144 | 9/2004 |
| WO | WO 2004/080462 | 9/2004 |
| WO | WO 2004/080966 | 9/2004 |
| WO | WO 2004/089286 | 10/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/082855 | 9/2005 |
| WO | WO 2005/092896 | 10/2005 |
| WO | WO 2005/117867 | 12/2005 |
| WO | WO 2005/117887 | 12/2005 |
| WO | WO 2006/004636 | 1/2006 |
| WO | WO 2006/014325 | 2/2006 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/038552 | 4/2006 |
| WO | WO 2006/062984 | 6/2006 |
| WO | WO 2006/090930 | 8/2006 |
| WO | WO 2006/090931 | 8/2006 |
| WO | 2006/137474 | 12/2006 |
| WO | WO 2006/137474 | 12/2006 |
| WO | WO 2007/000347 | 1/2007 |
| WO | WO 2007/002325 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/136103 | 11/2007 |
| WO | WO 2008/023698 | 2/2008 |
| WO | WO 2008/026577 | 3/2008 |
| WO | WO 2008/026748 | 3/2008 |
| WO | WO 2008/088088 | 7/2008 |
| WO | WO 2008/093855 | 8/2008 |
| WO | WO 2008/102870 | 8/2008 |
| WO | WO 2008/155387 | 12/2008 |
| WO | 2009/018238 | 2/2009 |
| WO | WO 2009/060945 | 5/2009 |
| WO | WO 2009/077874 | 6/2009 |
| WO | WO 2009/096377 | 8/2009 |
| WO | WO 2009/140549 | 11/2009 |
| WO | WO 2009/150256 | 12/2009 |
| WO | WO 2010/006225 | 1/2010 |
| WO | WO 2011/017583 | 2/2011 |
| WO | WO 2011/022335 | 2/2011 |
| WO | WO 2011/162343 | 12/2011 |
| WO | WO 2012/166899 | 12/2012 |

OTHER PUBLICATIONS

Abrams et al., SU11248 Inhibits KIT and Platelet-derived Growth Factor Receptor Beta in Preclinical Models of Human Small Cell Lung CancerMolecular Cancer Therapeutics., 2: 471-478, 2003.

Agnieszka et al., "Emergence of potential biomarkers of response to anti-angiogenic anti-tumor agents," International Journal of Cancer, Sep. 2010, 127(6):1251-1258.

Amended Claims filed in KR App. Ser. No. 10-2010-7011023, filed Jul. 17, 2013, 15 pages (with English translation).

Amendment and Response to Final Office Action under 37 C.F.R. §1.116 for U.S. Appl. No. 12/092,539, filed Jun. 15, 2011, 9 pages.

Amendment and Response to Final Office Action under 37 C.F.R. §1.116 for U.S. Appl. No. 12/864,817, filed Dec. 5, 2011, 10 pages.

Amendment and Response to Non-Final Office Action for U.S. Appl. No. 11/997,543, filed Aug. 19, 2011, 34 pages.

Amendment and Response to Office Action under 37 C.F.R. §1.111 for U.S. App. U.S. Appl. No. 11/997,719, filed Dec. 23, 2010, 21 pages.

Amendment and Response to Office Action under 37 C.F.R. §1.111 for U.S. Appl. No. 12/092,539, filed Mar. 11, 2011, 9 pages.

Amendment and Response to Office Action under 37 C.F.R. §1.111 for U.S. Appl. No. 12/439,339, filed Feb. 7, 2012, 11 pages.

Amendment and Response to Office Action under 37 C.F.R. §1.111 for U.S. Appl. No. 12/524,754, filed Feb. 17, 2012, 13 pages.

Amendment and Response to Office Action under 37 C.F.R. §1.111 for U.S. Appl. No. 12/741,682, filed Jul. 30, 2012, 49 pages.

Amendment and Response to Office Action under 37 C.F.R. §1.111 for U.S. Appl. No. 12/864,817, filed Aug. 9, 2011, 12 pages.

Amendment and Response to Office Action under 37 C.F.R. §1.111 for U.S. Appl. No. 13/205,328, filed Apr. 11, 2012, 12 pages.

Amendment and Response to Office Action under 37 C.F.R. §1.116 for U.S. Appl. No. 11/997,543, filed Jan. 9, 2012, 27 pages.

Amendment and Response to Office Action under 37 C.F.R. §1.116 for U.S. Appl. No. 12/439,339, filed Jul. 30, 2012, 9 pages.

Amendment filed in KR App. Ser. No. 10-2008-7029472, dated Nov. 20, 2013, 81 pages (with English translation).

Amendment filed in KR App. Ser. No. 10-2013-7020616, dated Nov. 22, 2013, 22 pages (with English translation).

Amendment filed on Apr. 11, 2006 for CN App. Ser. No. 01819710.8, 35 pages. (with English translation).

(56) References Cited

OTHER PUBLICATIONS

Amendment filed on May 21, 2009 for JP App. Ser. No. 2005-124034, 14 pages (with English translation).
Amendment filed on Oct. 1, 2013 in IN App. U.S. Ser. No. 10502/CHENP/2012, 10 pages.
Amendment in EP App. Ser. No. 07793075.8, dated Mar. 3, 2009, 5 pages.
Amendment, Response to Office Action under 37 C.F.R. § 1.111 and Information Disclosure Statement for U.S. Appl. No. 13/624,278, filed Jun. 28, 2013, 23 pages.
Anderson et al., "Preparation of Water-soluble Compounds through Salt Formation. The Practice of Medicinal Chemistry," Technomics, 347-349 and 355-356 (Sep. 25, 1999).
Argument and Amendment for JP App. U.S. Appl. No. 2008-556208, filed Mar. 21, 2013, 15 pages (with English translation).
Argument and Amendment for JP App. Ser. No. 2008-532141, filed Nov. 29, 2012, 12 pages (with English translation).
Australian ("AU") Office Action issued on Oct. 29, 2009 for corresponding AU Application No. 2006285673, 3 pages.
Bankston et al., "A Scaleable synthesis of BAY 43/9006: A Potent Raf Kinase Inhibitor for the Treatment of Cancer", Organic Process Res Dev., 6:777-81 (2002).
Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Carlomagno et al., "BAY 43/9006 inhibition of oncogenic RET mutants," J. Natl. Cancer Inst., 98(5):326-34 (2006).
Carniti et al., "The RetC62OR Mutation Affects Renal and Enteric Development in a mouse Model of Hirschprung's Disease", American Journal of Pathology, 168, 1262-1275, (2006).
Carter et al., "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated Volume 5, No Fear of Proteins", Visual Laboratory Notebook Series, Section 6, Immunostaining, pp. 127-163, Shujunsha, Co., Ltd., 1997 (Japanese).
Chinese Office Action directed at Appl. No. 200780017371 .9 mailed on Oct. 20, 2010, 13 pages with English translation.
Chinese Office Action for Application No. 200680041355.9 issued on Aug. 24, 2010, 10 pages (with English translation).
Chinese Office Action for Application No. 200680041355.9 issued on Mar. 5, 2010, 21 pages (with English translation).
Chinese Office Action with the English translation dated, Feb. 29, 2012, for Application No. 200680036592.6, 7 pages.
Chinese Response to Office Action directed at Appl. No. 200780017371 .9 filed on Feb. 24, 2011, 10 pages with English translation.
Chinese Response to Office Action for Application No. 200680041355.9 filed on Jul. 19, 2010, 4 pages with English translation.
Chinese Response to Office Action for Application No. 200680041355.9 filed on Nov. 8, 2010, 6 pages with English translation.
CN200780032071.8 Office Action issued on Oct. 13, 2010, 29 pp. with English translation.
Corvi et al., "RET IPCM-1: a novel fusion gene in papillary thyroid carcinoma", Oncogene, 19:4236-4242 (2000).
European Office Action for Application No. 06832529.9 issued on Oct. 15, 2009, 1 page.
European Office Action for Application No. 06832529.9 issued on Sep. 12, 2011, 3 pages.
Forbes et al., "Dissolution kinetics and solubilities of p-aminosalicylic acid and its salts," International Journal of Pharmaceutics, 126:199-208 (1995).
Funahashi et al., "P-2123, Lenvatinib treatment of differentiated thyroid cancer (DTC): Analysis to identify biomarkers associated with response," the 71$^{st}$ Annual Meeting of the Japanese Cancer Association, Sep. 19-21, 2012, p. 339.

Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Grieco et al., "PTC is a Novel Rearranged Form of the ret Proto-Oncogene and is Frequentrly Detected in Vivo in Human Thyroid Papillary Carcinomas", Cell, 60: 557-563 (1990).
Guo et al., "Expression of gastric cancer-associated MG7 antigen in gastric cancer, precancerous lesions and H. pylori-associated gastric diseased", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Inhibition of c-kit receptor tyrosine kinase activity by STI 571, a selective tyrosine kinase inhibitor," Blood, 96(3):925-932 (2000) (XP001097629).
Hertel LW., et al., "Evaluation of the Antitumor Activity of Gemcitabine (2',2'-Difluoro-2'-deoxycytidine)", Cancer Research, 50, 4417-4422, 1990.
Hori et al., "Suppression of Solid Tumor Growth by Immunoneutralizing Monoclonal Antibody against Human Basic Fibroblast Growth Factor", Cancer Research., 51, 6180-4, 1991.
Inai et al., "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
International Preliminary Report on Patentability in International Application No. PCT/JP2006/322516 issued on May 7, 2008,8 pages.
International Search Report for App. Ser. No. PCT/JP2005/016941, dated on Nov. 15, 2005, 4 pages.
International Search Report for PCT/JP2012/060279, May 29, 2012, 5 pages.
Invitation to declare maintenance of the application for EP App. No. 06023078.6, dated May 2, 2007, 1 page.
Joao et al., "Somatic trinucleotide change encompassing codons 882 and 883 of the RET protooncogene in a patient with sporadic medullary thyroid carcinoma", European Journal of Endocrinology, 142,573-575, (2000).
Kay et al., "Eosinophils and Eosinophil-Associated Cytokines in Allergic Inflammation," Int. Arch. Allergy Immunol., 113:196-199 (1997).
Kim, "Technology evaluation: Matuzumab, Merck KGaA", Curr Opin Mol Ther. 2004; 6(1 ):96-103.
Klugbauer et al., "Detection of a Novel Type of RET Rearrangement (PTC5) in Thyroid Carcinomas after Chernobyl and Analysis of the Involved RET-fused Gene RFG5", Cancer Research, 58:198-203 (1998).
Kotva et al., "Substances with Antineoplastic Activity, LIII. N-(δ-(4-Pyrrolo[2,3-d]Pyrimidinylthio) Valery] } Amino Acids and Analogous Derivatives of Di-and Triglycine," Collection Czechoslov. Chem. Commun., 38:1438-1444 (1973).
Kubo et al., "Novel Potent Orally Active Selective VEGFR-2 Tyrosine Kinase Inhibitors: . . . ureas", Journal of Medicinal Chemistry., 48, 1359-1366, 2005.
Leukemias, Hematology, and Oncology. http://www.merkmanuals.com/professional/print/sec11/ch142a.html Mar. 16, 2011, 5 pages.
Lukacs et al., "Stem Cell Factor (c-kit Ligand) Influences Eosinophil Recruitment and Histamine Levels in Allergic Airway Inflammation," J. Immunol., 156:3945-3951 (1996).
Maintenance and Response to EP Search Report in EP App. Ser. No. 06796594.7, dated Dec. 21, 2011, 43 pages.
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No. 8567, 2 pages.
Mexican Office Action in App. Ser. No. MX/a/2010/008187, dated Aug. 21, 2013, 6 pages (with English translation).
Miyazaki et al., "Synthesis, Structure and Biological Activity Relationship of E7080 and its Derivatives as Novel and Potent

(56) References Cited

OTHER PUBLICATIONS

Antiangiogenic Protein Tyrosine Kinase Inhibitors Including the VEGF Receptors, FGFR1 Receptor and PDGF Receptor," AIMECS03, Kyoto, Japan (Oct. 1417, 2003), 1 page.
Montalbetti and Falque, "Tetrahedron report number 740: Amide bond formation and peptide coupling," Tetrahedron, 2005, 61:10827-10852.
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210215.
Naran eta l., "Inhibition of HGF/MET as therapy for malignancy," Expert Opin. Ther. Targets, 2009, p. 569-581.
Notice of Acceptance in AA App. Ser. No. 2006282456, dated Aug. 17, 2009, 1 page.
Notice of Allowance dated Apr. 24, 2012 for U.S. Appl. No. 12/524,754, 10 pages.
Office Action dated Aug. 8, 2003 for PH App. Ser. No. 1-2003-500266, 1 page.
Office Action dated Jul. 24, 2009 for CN App. Ser. No. 200710007096.4, 8 pages (with English translation).
Office Action in CA App. Ser. No. 2704000, dated Mar. 27 ,2015, 3 pages.
Office Action in KR App. Ser. No. 10-2009-7005657, dated Mar. 28, 2014, 6 pages (with English translation).
Office Action in U.S. Appl. No. 12039381, dated Oct. 7, 2015, 22 pages.
Okayama et al., "Human Lung Mast Cells are Enriched in the Capacity to Produce Granulocyte-Macrophage Colony-Stimulating Factor in Response to IgE-Dependent Stimulation," Eur. J. Immunol , 28:708-715 (1998).
Pacini, "38th Annual Meeting of the European Thyroid Association", European Thyroid Association, Santiago de Compostela, Spain, Aug. 15, 2014, p. 73-p. 226.
Podar et al., "GW654652, the pan-inhibitor of VEGF receptors, blocks the growth and migration of multiple myeloma cells in the bone marrow microenvironment", Blood.,103, 3474-3479, 2004.
Preliminary Amendment and Response to Restriction Requirement in U.S. Appl. No. 12/439,339, filed Aug. 10, 2011, 24 pages.
Preliminary Amendment and Response to Restriction Requirement in U.S. Appl. No. 13/083,338, filed Apr. 30, 2012, 16 pages.
Preliminary Amendment filed on Dec. 2, 2005 for U.S. Appl. No. 10/420,466, 36 pages.
Request for Continued Examination (RCE) transmittal for U.S. Appl. No. 12/864,817, filed Dec. 22, 2011, 1 page.
Response filed IN App. Ser. No. 1571/CHENP/2007, dated Oct. 30, 2013, 9 pages.
Response filed in MX App. Ser. No. MX/a/2010/008187, dated Nov. 4, 2013, 21 pages (with English language translation).
Response filed on ug. 18, 2008 for NO App. Ser. No. 20031731, 2 pages (with English translation).
Response to Extended European Search Report in EP App. Ser. No. 07793075.8, dated Nov. 8, 2010, 11 pages.
Response to Office Action filed on Jan. 25,2013 for CA App. Ser. No. 2627598, 9 pages.
Response to Office Action under 37 C.F.R. §1.111 for U.S. Appl. No. 12/523,495, filed Dec. 7, 2011, 13 pages.
Response to Office Action under 37 C.F.R. §1.111 for U.S. Appl. No. 13/083,338, filed Apr. 8, 2011, 6 pages.
Response to Office Action under 37 C.F.R. §1.111 for U.S. Appl. No. 13/083,338, filed Sep. 6, 2012, 8 pages.
Response to Restriction Requirement for U.S. Appl. No. 11/997,543, filed Mar. 22, 2011, 4 pages.
Response to Restriction Requirement for U.S. Appl. No. 12/301,353, filed Nov. 23, 2010, 4 pages.
Response to Restriction Requirement for U.S. Appl. No. 12/524,754, filed Dec. 1, 2011, 2 pages.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Santoro et al., "Molecular Mechanisms of RET Activation in Human Cancer," Ann. N.Y. Academy of Sciences, 963:116-121 (2002).
Second Preliminary Amendment and Response to Restriction Requirement for U.S. Appl. No. 12/092,539, filed Nov. 22, 2010, 5 pages.
Shirai, et al., ""Role of low-substituted hydroxypropylcellulose in dissociation and bioavalability of novel fine granule system for masking bitter taste," Biol. Pharm. Bull, 17(3): 427-431 (1994)."
Submission Document Before the Patent Office dated Apr. 22, 2013 for IL App. Ser. No. 207089, 7 pages (with English translation).
Submissioin Document re RCE and Information Disclosure Statement on Oct. 18, 2013, in U.S. Appl. No. 12/524,754, 17 pages.
Submission documents re RCE in U.S. Appl. No. 12/524,754, filed Feb. 3, 2014, 1 page.
Submission of Amendments and Complete Specification dated Apr. 10, 2013 for in App. Ser. No. 1571/CHENP/2007, 15 pages.
Sun et al., "Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethy1-1H-pyrrole-3carboxylic acid . . . Tyrosine Kinase", Journal of Medicinal Chemistry., 46:1116-1119 (2003).
Tahara et al., "Lenvatinib in Radioactive Iodine-refractory Differentiated Thyroid Cancer: Results of the Phase 3 trial (SELECT trial),"01-18-1, Abstract and Presentation Document, $12^{th}$ Annual Meeting of Japanese Society of Medical Oncology, Jul. 17, 2014, 21 pages.
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011, 15 pages.
Wozniak et al., "Randomized trial comparing cisplatin with cisplatin plus vinorelbine in the treatment of advanced non-small-cell lung cancer: a Southwest Oncology Group study," *J. Clin. Oncol.*, 16(7):2459-2465 (1998).
Yamada et al., "New technique for staining," Monthly Medical Technology Supplementary Volume (Apr. 1999) (with English translation), 13 pages.
Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*,45:1070-1071 (Mar. 2004).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zurita et al., "Circulatmg biomarkers for vascular-endothelial growth factor inhibitors in renal cell carcinoma," Cancer, May 2009, 115(S10):2346-2354.
"Carboxymethyl Cellulose Sodium." Chemical Land 21. Retrieved Apr. 24, 2012. <http://www.chemicalland21.comlindustrialchem/perfonnancepolymer/Carboxymethyl%20CELLULOSE%20SODIUM%20SAL T.htm>, 2 pages.
"Carboxymethylcellulose Sodium." Merck Index: An Encyclopedia of Chemicals, Drugs, & Biologicals: 13th Ed. New Jersey: Merck & Co (2001), p. 308.
"Current Protocols in Molecular Biology", John Wiley & Sons Section 11.4-11.13 (1987), 62 pages.
"Pharmacokinetics (PK) and tolerability of GW786034, a VEGFR tyrosine kinase inhibitor, after daily oral administration to patients with solid tumors." Proc. Am. Soc. Clin. Oncology, (Abstract 3054), 2004, 2 pages.

(56) References Cited

OTHER PUBLICATIONS

"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, pp. 1-5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium and Beruf, DT. Apotheker-Verl, Stuttgart; DE, Jan. 1, 2000, pp. 40-52, XP008143620 (English translation).
"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
AACR American Association Cancer Research, 92nd Annual Meeting, 42:583, Mar. 24-28, 2001, New Orleans, LA, USA, 3126.
Abrams et al., SU11248 Inhibits KIT and Platelet-derived Growth Factor Receptor Beta in Preclinical Models of Human Small Cell Lung CancerMolecular Cancer Therapeutics., 2:471-478, 2003.
Abuzar et al., "Synthesis of some new 7-chloro-4-substituted quinolines as potential antiparasitic agents," Eur. J. Med. Chem., 21(1):5-8 (1986).
Additional Response in IL App. Ser. No. 188670, dated Oct. 25, 2011, 4 pages (with English translation).
Advisory Action for U.S. Appl. No. 12/092,539 issued on Jun. 28, 2011, 3 pages.
Advisory Action in U.S. Appl. No. 12/315,291, dated Mar. 24, 2011, 10 pages.
Agarwal et al., "Binding of discoidin domain receptor 2 to collagen I: an atomic force microscopy investigation," Biochemistry, 41(37):11091-11098 (2002).
Agnieszka et al., "Emergence of potential biomarkers of" response to anti-angiogenic anti-tumor agents," International Journal of Cancer, Sep. 2010, 127(6):1251-1258.
Almarsson et al., "High-Throughput Surveys of Crystal Form Diversity of Highly Polymorphic Pharmaceutical Compounds," Crystal Growth & Design, Sep. 10, 2003, 3(6):927-933.
Altschul et al., "Basic Local Alignment Search Tool", J. Mol. Biol. 215:403-410 (1990).
Amended Claims filed in EP App. Ser. No. 11798224.9, filed Aug. 2, 2013, 35 pages.
Amended Claims filed in KR App. Ser. No. 10-2010-7011023, filed Jul. 17, 2013, 15 pages. (with English translation).
Amended Claims filed in RU App. Ser. No. 2013140169, dated Aug. 29, 2013, 17 pages (with English translation).
Amended Claims in BR App. Ser. No. BR112012003592-4, dated Oct. 23, 2014, 12 pages (with English translation).
Amended claims in EP App. Ser. No. 04807580.8, dated Jun. 16, 2014, 7 pages.
Amended Claims in MY App. Ser. No. PI2011700172, dated in Jul. 3, 2014, 15 pages.
Amended description filed after receipt of search report for EP Patent App. No. 10809938.3, filed Dec. 8, 2011, 2 pages.
Amended description filed after receipt of search report for EP Patent App. No. 10809938.3, filed Sep. 14, 2010, 2 pages.
Amended Drawing in IL App. Ser. No. 217197, dated Oct. 22, 2014, 4 pages (with English translation).
Amended Drawing in PH App. Ser. No. 1-2011-502441, dated Oct. 17, 2014, 2 pages.
Amended drawings in EP App. Ser. No. 10809938.3, dated Nov. 11, 2014, 14 pages.
Amended set of Claims in EP App. Ser. No. 11798224.9, dated Sep. 19, 2014, 53 pages.
Amended Specification filed in AU App. Ser. No. 2012246490, filed Aug. 2, 2013, 15 pages.
Amendment after Allowance filed on Jan. 4, 2011 for CA App. Ser. No. 2426461, 12 pages.
Amendment and Argument filed on Apr. 27, 2012 in response to the JP Office Action for JP2007-542863, 13 pages and English translation.
Amendment and RCE submission documents filed in U.S. Appl. No. 12/039,381, dated Oct. 23, 2013, 13 pages.
Amendment and Request for Continued Examiner (RCE) in U.S. Appl. No. 13/083,338, dated Oct. 10, 2014, 5 pages.
Amendment and Response filed in U.S. Appl. No. 11/997,543, dated Dec. 19, 2013, 38 pages.
Amendment and Response for Application No. IL Patent Application No. 195282 dated Jul. 11, 2013, 13 pages (with English translation).
Amendment and Response to Final Office Action under 37 C.F.R. §1.116 for U.S. Appl. No. 12/092,539, filed on Jun. 15, 2011, 9 pages.
Amendment and Response to Final Office Action under 37 C.F.R. §1.116 for U.S. Appl. No. 12/864817, filed on Dec. 5, 2011, 10 pages.
Amendment and Response to Non-Final Office Action for U.S. Appl. No. 11/997,543, filed on Aug. 19, 2011, 34 pages.
Amendment and Response to Office Action under 37 C.F.R § 1.111 for U.S. Appl. No. 12/439,339, dated Aug. 22, 2013, 14 pages.
Amendment and Response to Office Action under 37 C.F.R. § 1.111 dated Apr. 2, 2013 for U.S. Appl. No. 13/083,338, 9 pages.
Amendment and Response to Office Action under 37 C.F.R. §1.111 for U.S. Appl. No. 11/997,719, filed on Dec. 23, 2010, 21 pages.
Amendment and Response to Office Action under 37 C.F.R. §1.111 for U.S. Appl. No. 12/092539, filed on Mar. 11, 2011, 9 pages.
Amendment and Response to Office Action under 37 C.F.R. §1.111 for U.S. Appl. No. 12/439,339, filed on Feb. 7, 2012, 11 pages.
Amendment and Response to Office Action under 37 C.F.R. §1.111 for U.S. Appl. No. 12/524,754, filed on Feb. 17, 2012, 13 pages.
Amendment and Response to Office Action under 37 C.F.R. §1.111 for U.S. Appl. No. 12/741,682, filed on Jul. 30, 2012, 49 pages.
Amendment and Response to Office Action under 37 C.F.R. §1.111 for U.S. Appl. No. 12/864,817, filed on Aug. 9, 2011, 12 pages.
Amendment and Response to Office Action under 37 C.F.R. §1.111 for U.S. Appl. No. 13/205,328, filed on Apr. 11, 2012, 12 pages.
Amendment and Response to Office Action under 37 C.F.R. §1.116 for U.S. Appl. No. 11/997,543, filed on Jan. 9, 2012, 27 pages.
Amendment and Response to Office Action under 37 C.F.R. §1.116 for U.S. Appl. No. 12/439,339, filed on Jul. 30, 2012, 9 pages.
Amendment filed in BR App. Ser. No. BR112012032462-4, dated Nov. 4, 2013, 21 pages (with English translation).
Amendment filed in EP App. Ser. No. 12774278.1, filed Aug. 13, 2013, 12 pages.
Amendment filed in EP App. Ser. No. 12793322.4, dated Nov. 28, 2013, 6 pages.
Amendment filed in JP App. Ser. No. 2008-532141, filed Jul. 5, 2013, 2 pages (with English translation).
Amendment filed in KR App. Ser. No. 10-2008-7027527, dated Jan. 27, 2014, 12 pages (with English translation).
Amendment filed in KR App. Ser. No. 10-2008-7029472, dated May 1, 2014, 14 pages (with English translation).
Amendment filed in KR App. Ser. No. 10-2008-7029472, dated Nov. 20, 2013, 81 pages. (with English translation).
Amendment filed in KR App. Ser. No. 10-2009-7005657, dated May 7, 2014, 15 pages (with English translation).
Amendment filed in KR App. Ser. No. 10-2009-7017694, dated Feb. 28, 2014, 7 pages.
Amendment filed in KR App. Ser. No. 10-2013-7020616, dated Nov. 22, 2013, 22 pages. (with English translation).
Amendment filed in U.S. Appl. No. 13/805,826, dated Sep. 9, 2013, 14 pages.
Amendment filed on Apr. 11, 2006 for CN App. Ser. No. 01819710.8, 35 pages (with English translation).
Amendment filed on Apr. 17, 2002 for TW App. Ser. No. 90125928, 26 pages (with English translation).
Amendment filed on Apr. 19, 2005 for JP App. Ser. No. 2002-536056, 26 pages (with English translation).
Amendment filed on Aug. 13, 2013 in JP App. Ser. No. P2009-540099, 8 pages (with English translation).

(56) References Cited

OTHER PUBLICATIONS

Amendment filed on Aug. 17, 2004 for ZA App. Ser. No. 2003/3567, 39 pages.
Amendment filed on Aug. 29, 2013 in CN App. Ser. No. 201280010898.X, 24 pages (with English translation).
Amendment filed on Aug. 4, 2004 for ZA App. Ser. No. 2003/3567, 95 pages.
Amendment filed on Aug. 6 2013, for JP App. Ser. No. 2009-551518, 6 pages (with English translation).
Amendment filed on Dec. 12, 2011 for JO Patent App. No. 55/2011, 6 pages (with English translation).
Amendment filed on Dec. 15, 2011 for VN App. Ser. No. 1-2011-03484, 5 pages (with English translation).
Amendment filed on Dec. 22, 2011 for ZA App. Ser. No. 2011/08697, 2 pages.
Amendment filed on Feb. 9, 2011 for TW App. Ser. No. 100104281, 2 pages.
Amendment filed on Jan. 11, 2010 for CN App. Ser. No. 200580026468.7, 4 pages (with English translation).
Amendment filed on Jan. 26, 2010 for CN App. Ser. No. 200710007097.9, 9 pages (with English translation).
Amendment filed on Jul. 2, 2009 for CN App. Ser. No. 200710007097.9, 9 pages (with English translation).
Amendment filed on Jun. 22, 2010 for CN App. Ser. No. 200710007097.9, 9 pages (with English translation).
Amendment filed on Mar. 20, 2012 for KR Patent App. No. 10-2012-7003846, 7 pages (with English translation).
Amendment filed on Mar. 23, 2009 for JP Patent Application No. 2005-124034, 29 pages (with English translation).
Amendment filed on Mar. 6, 2006 for KR App. Ser. No. 10-2003-7005506, 34 pages (with English translation).
Amendment filed on Mar. 7, 2005 for JP App. Ser. No. 2002-536056, 23 pages (with English translation).
Amendment filed on Mar. 8, 2006 for KR App. Ser. No. 10-2005-7020292, 33 pages (with English translation).
Amendment filed on May 10, 2012 for JP Patent Application No. 2011-527665, 5 pages.
Amendment filed on May 21, 2009 for JP App. Ser. No. 2005-124034, 14 pages. (with English translation).
Amendment filed on May 28, 2003 for CN App. Ser. No. 01819710.8, 8 pages (with English translation).
Amendment filed on Nov. 19, 2009 for CN App. Ser. No. 200710007097.9, 9 pages (with English translation).
Amendment filed on Nov. 24, 2011 for KR App. Ser. No. 10-2007-7001347, 7 pages (with English translation).
Amendment filed on Oct. 1, 2013 in IN App. Ser. No. 10502/CHENP/2012, 10 pages.
Amendment filed on Oct. 25, 2005 for KR App. Ser. No. 10-2003-7005506, 53 pages (with English translation).
Amendment filed on Oct. 28, 2011 for LB Patent App. No. 9292, 2 pages.
Amendment filed on Oct. 9, 2006 for CN App. Ser. No. 01819710.8, 28 pages (with English translation).
Amendment filed on Sep. 13, 2005 for CN App. Ser. No. 01819710.8, 51 pages (with English translation).
Amendment filed on Sep. 23, 2009 for CN App. Ser. No. 200580026468.7, 11 pages (with English translation).
Amendment filed on Sep. 23, 2013 in AU App. Ser. No. 2011270165, 35 pages.
Amendment for Chinese Patent Application No. 201080030508.6 dated Feb. 7, 2013, 17 pages with English translation.
Amendment for IN App. Ser. No. 7026/CHENP/2013, dated Sep. 5, 2013, 8 pages.
Amendment in AU App. Ser. No. 2005217325, dated Aug. 9, 2006, 11 pages.
Amendment in AU App. Ser. No. 2005217328, dated Aug. 9, 2006, 10 pages.
Amendment in AU App. Ser. No. 2006282456, dated Apr. 26, 2012, 6 pages.
Amendment in AU App. Ser. No. 2006282456, dated Jan. 25, 2008, 26 pages.
Amendment in AU App. Ser. No. 2007289787, dated Apr. 7, 2009, 16 pages.
Amendment in BD App. Ser. No. 184/2006, dated May 6, 2008, 3 pages.
Amendment in BD App. Ser. No. 184/2006, dated Sep. 26, 2007, 4 pages.
Amendment in BR App. Ser. No. PI0616799/3, dated May 29, 2012, 6 pages.
Amendment in Canadian App. Ser. No. 2828946, dated Aug. 30, 2013, 14 pages.
Amendment in CN App. Ser. No. 200580001760.3, dated May 15, 2007, 31 pages (with English translation).
Amendment in CN App. Ser. No. 200680021939.X, dated Dec. 18, 2007, 23 pages (with English translation).
Amendment in CN App. Ser. No. 200780019520.5, dated Nov. 27, 2008, 10 pages (with English translation).
Amendment in CN App. Ser. No. 2008800045113, dated Aug. 7, 2009, 36 pages (with English translation).
Amendment in EP App. Ser. No. 05719973.9, dated Oct. 30, 2006, 2 pages.
Amendment in EP App. Ser. No. 06796594.7, dated Apr. 19, 2012, 3 pages.
Amendment in EP App. Ser. No. 06796594.7, dated Jan. 11, 2008, 3 pages.
Amendment in EP App. Ser. No. 06796594.7, dated Nov. 16, 2007, 3 pages.
Amendment in EP App. Ser. No. 07793075.8, dated Jan. 26, 2011, 12 pages.
Amendment in EP App. Ser. Appl. No. 07793075.8, dated Mar. 3, 2009, 5 pages.
Amendment in EP App. Ser. No. 08711837.8, dated Sep. 8, 2009, 23 pages.
Amendment in EP App. Ser. No. 09713617.0, dated Sep. 1, 2010, 3 pages.
Amendment in IL App. Ser. No. 188670, dated May 2, 2012, 7 pages (with English translation).
Amendment in IL App. Ser. No. 197002, dated Feb. 11, 2009, 4 pages.
Amendment in IL App. Ser. No. 200466, dated Aug. 18, 2009, 28 pages.
Amendment in IN App. Ser. No. 1424/CHENP/2008, dated Apr. 27, 2012, 4 pages.
Amendment in IN App. Ser. No. 2371/CHENP/2012, dated Oct. 30, 2014, 2 pages.
Amendment in Israeli App. Ser. No. 200090, dated Oct. 2, 2013, 10 pages (with English translation).
Amendment in JO App. Ser. No. 280/2006, dated Oct. 19, 2007, 3 pages (with English translation).
Amendment in JP App. Ser. No. 2007-532099, dated Dec. 25, 2007, 6 pages (with English translation).
Amendment in JP App. Ser. No. 2007-532099, dated Sep. 25, 2007, 28 pages (with English translation).
Amendment in JP App. Ser. No. 2008-530917, dated Dec. 13, 2012, 6 pages (with English translation).
Amendment in JP App. Ser. No. 2009-554285, dated Aug. 19, 2010, 7 pages (with English translation).
Amendment in JP App. Ser. No. P2009-510543, dated Nov. 9, 2009, 25 pages (with English translation).
Amendment in Korean App. Ser. No. 10-2012-7033886, dated Sep. 27, 2013, 34 pages (with English translation).
Amendment in KR App. Ser. No. 10-2006-7013907, dated Sep. 28, 2007, 10 pages (with English translation).
Amendment in KR App. Ser. No. 10-2006-7013940, dated Oct. 1, 2007, 43 pages (with English translation).
Amendment in KR App. Ser. No. 10-2007-7026886, dated Dec. 27, 2007, 4 pages (with English translation).
Amendment in KR App. Ser. No. 10-2007-7026886, dated Nov. 21, 2007, 9 pages (with English translation).
Amendment in KR App. Ser. No. 10-2007-7026886, dated Oct. 27, 2009, 4 pages (with English translation).

(56) References Cited

OTHER PUBLICATIONS

Amendment in KR App. Ser. No. 10-2008-7029577, dated Apr. 1, 2009, 6 pages (with English translation).
Amendment in KR App. Ser. No. 10-2009-7013723, dated Aug. 10, 2009, 17 pages (with English translation).
Amendment in KR App. Ser. No. 10-2010-7011023, dated Oct. 21, 2014, 31 pages.
Amendment in KR App. Ser. No. 10-2010-7018835, dated Dec. 1, 2014, 18 pages (with English translation).
Amendment in KR App. Ser. No. 10-2012-7003846, dated Nov. 26, 2014, 20 pages (with English translation).
Amendment in Mexican App. Ser. No. MX/a/2012/014776, dated Oct. 21, 2013, 10 pages (with English translation).
Amendment in MY App. Ser. No. PI20071922, dated Jul. 17, 2008, 243 pages.
Amendment in NO App. Ser. No. 20080460, dated May 14, 2012, 4 pages (with English translation).
Amendment in PH App. Ser. No. 1-2007-502319, dated May 14, 2012, 3 pages.
Amendment in Russian App. Ser. No. 2012158142, dated Oct. 17, 2013, 48 pages (with English translation).
Amendment in SA App. Ser. No. 06270287, dated Oct. 22, 2007, 12 pages.
Amendment in SG App. Ser. No. 200718614/1, dated Aug. 24, 2010, 13 pages.
Amendment in TH App. Ser. No. 0601004017, dated Sep. 25, 2007, 6 pages (with English translation).
Amendment in TW App. Ser. No. 100104281, dated Oct. 22, 2014, 8 pages.
Amendment in U.S. Appl. No. 11/662,425, dated Sep. 2, 2014, 6 pages.
Amendment in U.S. Appl. No. 11/892,785, dated Dec. 17, 2008, 17 pages.
Amendment in U.S. Appl. No. 11/065,631, dated May 28, 2008, 16 pages.
Amendment, Response to Office Action under 37 C.F.R. §1.111 and Information Disclosure Statement for U.S. Appl. No. 13/624,278, filed Jun. 28, 2013, 23 pages.
Amendments received before examination for EP App. Ser. No. 01976786.2, dated Sep. 10, 2004, 126 pages.
Amendments to the specification filed on Mar. 26, 2012 for AU Patent Appl. No. 2010285740, 15 pages.
American Association for Cancer Research, "Redefining the Frontiers of Science," 94th Annual Meeting, vol. 44, 2nd Edition, Washington Convention Center, Washington, DC (Jul. 11-14, 2003), 3 pages.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Anderson and Flora, "Preparation of Water-Soluble Compounds Through Salt Formation," Practice of Medicinal Chem., 1996, pp. 739-754.
Anderson et al, "Clinical, Safety, and Economic Evidence in Radioactive Iodine-Refractory Differentiated Thyroid Cancer: A Systematic Literature Review", Thyroid, 23(4):392-407, 2013.
Anderson et al., "Preparation of Water -soluble Compounds through Salt Formation. The Practice of Medicinal Chemistry," Technomics, 347-349 and 355-356 (Sep. 25, 1999).
Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143).
Antibodies: A Laboratory Manual, E. Harlow and D. Lane, ed. Cold Spring Harbor Laboratory (Cold Spring Harbour, NY, 1988), 190 pages.
Appeal for Reversal in CO App. Ser. No. 12-022608, dated Jan. 28, 2014, 17 pages (with English translation).
Appeal in SA App. Ser. No. 06270287, dated Jun. 23, 2010, 4 pages (with English translation).
Applicant Interview Summary Under 37 C.F.R § 1.133(b) for U.S. Appl. No. 12/439,339, dated May 31, 2013, 7 pages.
Applicant Observation for CN App. Ser. No. 200780017371.9, filed May 29, 2013, 6 pages (with English translation).
Application for Patent Term Adjustment in U.S. Appl. No. 12/439,339, dated Dec. 18, 2014, 8 pages.
Approval of request for amendments for EP App. Ser. No. 04025700.8, dated Mar. 13, 2008, 1 page.
Argument and Amendment for JP App. Ser. No. 2008-556208, filed Mar. 21, 2013, 15 pages (with English translation).
Argument and Amendment for CN 200880002425.9 filed on Jul. 18, 2011, 8 pages with English translation.
Argument and Amendment for JP App. Ser. No. 2008-532141, filed Nov. 29,2012, 12 pages (with English translation).
Argument and Amendment for JP. App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument Brief filed in KR App. Ser. No. 10-2008-7029577, dated Feb. 27, 2014, 30 pages (with English translation).
Argument Brief filed on Mar. 6, 2006 for KR App. Ser. No. 10-2003-7005506, 45 pages (with English translation).
Argument Brief filed on Mar. 8, 2006 for KR App. Ser. No. 10-2005-7020292, 42 pages (with English translation).
Argument Brief filed on Nov. 24, 2011 for KR App. Ser. No. 10-2007-7001347, 52 pages (with English translation).
Argument Brief filed on Oct. 25, 2005 for KR App. Ser. No. 10-2003-7005506, 20 pages (with English translation).
Argument Brief in KR App. Ser. No. 10-2007-7026886, dated Oct. 27, 2009, 7 pages (with English translation).
Argument filed in KR App. Ser. No. 10-2009-7017694, dated Feb. 28, 2014, 48 pages.
Argument filed on Apr. 19, 2005 for JP App. Ser. No. 2002-536056, 6 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Argument filed on Mar. 23, 2009 for JP App. Ser. No. 2005-124034, 12 pages (with English translation).
Argument filed on May 21, 2009 for JP App. Ser. No. 2005-124034, 5 pages (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al , "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Asano et al., "Broad-spectrum preclinical combination activity of eribulin combined with various anticancer agents in human breast cancer, lung cancer, ovarian cancer, and melanoma xenograft models," European J Cancer, 50(Suppl 6):20, Nov. 19, 2014.
Asu no Shinyaku ("The New Drugs of Tomorrow"), editing/printing by Technomics, Inc., 81-83 (Dec. 2006) (English translation), 14 pages.
Australian (""AU"") Office Action issued on Oct. 29, 2009 for corresponding AU Application No. 2006285673, 3 pages.
Australian ("AU") Notice of Allowance dated Nov. 22, 2010 for corresponding AU Application No. 2006285673, 3 pages.
Australian ("AU") Office Action issued on May 19, 2010 for corresponding AU Application No. 2006285673, 2 pages.
Australian ("AU") Office Action issued on May 7, 2009 for corresponding AU Application No. 2006285673, 2 pages.
Australian Office Action directed at Appl. No. 2007252506 issued on Jan. 13, 2012, 2 pages.
Australian Office Action directed at Appl. No. 2007252506 issued on Nov. 7, 2011, 5 pages.
Australian Office Action for App. Ser. No. 2008205847, issued on Apr. 11, 2012, 2 pages.

(56) References Cited

OTHER PUBLICATIONS

Australian Office Action for App. Ser. No. 2008211952, issued on Apr. 3, 2012, 2 pages.
Australian Office Action for Application No. 2006309551 issued on Feb. 2, 2012, 2 pages.
Australian Office Action for Application No. AU2006309551 issued on Apr. 28, 2011, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012, 81 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Bajwa et al., "Animalarials. 1. Heterocyclic Analogs of N-Substituted Naphthalenebisoxazines"; Journal of Medicinal Chemistry; 1972; 16(2): 134-138.
Baker et al., "Blockade of vascular endothelial growth factor receptor and epidermal growth factor receptor signaling for therapy of metastatic human pancreatic cancer," Cancer Res., 62:1996-2003 (2002).
Bankston et al., "A Scaleable synthesis of BAY 43-9006: A Potent Raf Kinase Inhibitor for the Treatment of Cancer", Organic Process Res Dev., 6:777-81 (2002).
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapyl", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," Journal of Pharmaceutical Sciences, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Besson et al., "Pten/MMAC1/TEP1 in signal transduction and tumorigenesis," Ep J Biochem., 1999, 263:605-611.
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Boissan et al., "c-Kit and c-kit mutations in mastocytosis and other hematological diseases," J. Leukocyte Biol., 67:135-148 (2000).

Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Bramhall, S., "The Matrix Metalloproteinases and Their Inhibitors in Pancreatic Cancer", International J. Pancreatol., 21, 1-12, 1997.
Brief communication to applicant for EP App. Ser. No. 01976786.2, dated Sep. 9, 2005, 1 page.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.
Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Burwell, Jr, "The Cleavage of Ethers," Chem Rev., 54(4):615-685, Feb. 26, 1954.
Bussolino et al., "Role of Soluble Mediators in Angiogenesis," Eur. J. Cancer, 32A(14):2401-2412 (1996).
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action issued on Jan. 14, 2010 for corresponding CA Application No. 2,620,594, 3 pages.
Canadian ("CA") Office Action issued on Jan. 6, 2011 for corresponding CA Application No. 2,620,594, 3 pages.
Canadian Office Action for App. Ser. No. 2426461, dated Dec. 6, 2007, 5 pages.
Canadian Office Action for App. Ser. No. 2426461, dated Feb. 10, 2010, 2 pages.
Canadian Office Action for App. Ser. No. 2426461, dated May 8, 2009, 2 pages.
Canadian Office Action for App. Ser. No. 2426461, dated Nov. 20, 2008, 3 pages.
CancerCare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carey, "Organic Chemistry 4e: Chapter 24: Phenols," McGraw Hill, http://www.mhhe.com/physsci/chemistry/carey/student/olc/ch24reactionsarylethers.html. Accessed Oct. 3, 2014, 2000, 4 pages.
Carlomagno et al., "Point Mutation of the RET Proto-Oncogene in the TT Human Medullary Thyroid Carcinoma cell Line", Biochemical and Biophysical Research Communications, 207,1022-1028 (1995).
Carlomagno et al., "BAY 43-9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carter et al, "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Certificate of Correction in U.S. Appl. No. 12/741,682, dated Aug. 4, 2015, 2 pages.

(56) References Cited

OTHER PUBLICATIONS

Chen et al., "FGFR3 as a therapeutic target of the small molecule inhibitor PKC412 in hematopoietic malignancies," Oncogene, 24:8259-8267 (2005).
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Childhood Papillary Thyroid Carcinoma, Cancer Research, 60: 2786-2789 (2000).
Chinese ("CN") Office Action issued on Dec. 4, 2009 for corresponding CN Application No. 200680036592.6, 8 pages with English translation.
Chinese Office Action directed at Appl. No. 200780017371.9 mailed on Oct. 20, 2010, 13 pages with English translation.
Chinese Office Action for App. Ser. No. 200580026468.7, issued on Jun. 26, 2009, 25 pages (with English translation).
Chinese Office Action for App. Ser. No. 200710007097.9, issued on Mar. 6, 2009, 5 pages.
Chinese Office Action for App. Ser. No. 200780017371.9, issued on Mar. 7, 2012, 8 pages with English translation.
Chinese Office Action for App. Ser. No. 200880002425.9, issued on Mar. 7, 2012, 7 pages (with English translation).
Chinese Office Action for App. Ser. No. 200880003336.6, issued on May 24, 2011, 24 pages (with English translation).
Chinese Office Action for App. Ser. No. 200880115011.7, issued on Feb. 20, 2012, 10 pages (with English translation).
Chinese Office Action for App. Ser. No. 201080030508.6, issued on Nov. 30, 2012, 13 pages, (with English translation).
Chinese Office Action for Application No: 200680041355.9 issued on Aug. 24, 2010, 10 pages (with English translation).
Chinese Office Action for Application No: 200680041355.9 issued on Mar. 5, 2010, 21 pages (with English translation).
Chinese Office Action for CN 200680020317.5 dated Aug. 3, 2012 with English translation, 11 pages.
Chinese Office Action with the English translation dated, Feb. 29, 2012, for Application No, 200680036592.6, 7 pages.
Chinese Response to Office Action directed at Appl. No. 200780017371.9 filed on Feb. 24, 2011, 10 pages with English translation.
Chinese Response to Office Action for Application No: 200680041355.9 filed on Jul. 19, 2010, 4 pages with English translation.
Chinese Response to Office Action for Application No:200680041355.9 filed on Nov. 8, 2010, 6 pages with English translation.
Chinese Response to the Chinese Decision of Rejection, filed on Feb. 7, 2013, for corresponding Chinese Application No. 200680036592.6, 27 pages.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, 98:463-469 (2002).
CA Notice of Allowance for Appl. No. 2,620,594 dated May 3, 2012, 1 page.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010), 3 pages.
CN200780032071.8 Office Action issued on Oct. 13, 2010, 29 pages with English translation.
CN200780032071.8 Response to Office Action filed on Feb. 16, 2011, 62 pages with English translation.
CN200880003336.6 Response to Office Action filed on Oct. 8, 2011, 10 pages.
Codon 915 Mutation, Japanese Journal of D Cancer Research, 90, 1-5, (1999).
Cohen et al., "Expression of Stem Cell Factor and c-kit in Human Neuroblastoma," Blood, 84(10):3465-3472 (1994).
Colombian Office Action for App. Ser. No. 12-022608, dated Oct. 7, 2013, 10 pages (with English translation).
Comments re Board of Appeal in EP App. Ser. No. 04807580.8, dated Jul. 7, 2014, 3 pages.
Communication about intention to grant a European patent for EP App. Ser. No. 01976786.2, dated Sep. 4, 2006, 173 pages.
Communication about intention to grant a European patent for EP App. Ser. No. 04025700.8, dated Oct. 15, 2007, 392 pages.
Communication about intention to grant a European patent for EP App. Ser. No. 05783232.1, dated Nov. 20, 2008, 70 pages.
Communication about intention to grant a European patent for EP App. Ser. No. 06023078.6, dated Jul. 18, 2008, 169 pages.
Communication from the Examining Division for EP App. Ser. No. 01976786.2, dated Aug. 17, 2005, 4 pages.
Communication from the Examining Division for EP App. Ser. No. 01976786.2, dated Mar. 21, 2006, 3 pages.
Communication from the Examining Division for EP App. Ser. No. 01976786.2, dated Sep. 19, 2005, 4 pages.
Communication from the Examining Division for EP App. Ser. No. 04025700.8, dated Apr. 10, 2006, 3 pages.
Communication from the Examining Division for EP App. Ser. No. 04025700.8, dated Oct. 23, 2006, 2 pages.
Communication from the Examining Division for EP App. Ser. No. 05783232.1, dated Feb. 7, 2008, 1 pages.
Communication from the Examining Division for EP App. Ser. No. 06023078.6, dated Aug. 2, 2007, 1 page.
Communication from the Examining Division for EP App. Ser. No. 06023078.6, dated Sep. 26, 2007, 2 pages.
Communication re Intention to Grant Patent in EP App. Ser. No. 07793075.8, dated Nov. 9, 2012, 97 pages.
Communication re Intention to Grant Patent in EP App. Ser. No. 07805959.9, dated Jun. 21, 2011, 70 pages.
Communication regarding the expiry of opposition period for EP App. Ser. No. 01976786.2, dated Jan. 4, 2008, 1 page.
Communication regarding the expiry of opposition period for EP App. Ser. No. 04025700.8, dated May 7, 2009, 1 page.
Communication regarding the expiry of opposition period for EP App. Ser. No. 05783232.1, dated Feb. 19, 2010, 1 page.
Communication regarding the expiry of opposition period for EP App. Ser. No. 06023078.6, dated Nov. 4, 2009, 1 page.
Communication under Rule 71(3) EPC dated Nov. 20, 2008, for Application No. 05783232.1, 70 pages.
Continuation Patent Application, Preliminary Amendment and Information Disclosure Statement for U.S. Appl. No. 13/923,858, filed Jun. 21, 2013, 97 pages.
Corbin et al., "Sensitivity of oncogenic KIT mutants to the kinase inhibitors MLN518 and PD180970," Blood., 104, 3754-3757, 2004.
Correction Request in CO App. Ser. No. 12-022608, dated Dec. 24, 2014, 3 pages (with English translation).
Corvi et al., "RET IPCM—1: a novel fusion gene in papillary thyroid carcinoma", Oncogene, 19:4236-4242 (2000).
Coupling Reagents, "Advanced Automated Peptide Protein Technologies," Published Aug. 3, 2007, 4 pages.
Creates a Novel Rearranged Form (PTC8) of the RET Proto-Oncogene in Radiation-induced.

(56) References Cited

OTHER PUBLICATIONS

Croom et al., "Imatinib mesylate," Drugs, 63(5):513-522 (2003).
Da Silva et al., "A novel germ-line point mutation in RET exon 8 (Gly(533)Cys) in a large kindred with familial medullary thyroid carcinoma," J. Clin. Endocrinol. Metab., 88:5438-5443 (2003).
Dankort et al., "Braf V660E cooperaties with Pten loss to induce metastic melanoma," Nature Genetics, 2009, 41(5):544-552.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
Davies et al., "Mutations of the BRAF gene in human cancer," Nature, Jun. 27, 2002, 417:949-954.
De Lange et al., "Phase II trial of cisplatin and gemcitabine in patients with advanced gastric cancer," Annals of Oncology, 15:484-488 (2004).
Decision of Final Rejection issued in CN App. Ser. No. 200780017371.9, dated Jul. 3, 2013, 16 pages (with English translation).
Decision of Grant in RU App. Ser. No. 2008110932, dated Feb. 6, 2009, 29 pages (with English translation).
Decision of Rejection mailed on Oct. 30, 2012 issued for corresponding Chinese Application No. 200680036592.6, 8 pages with full English language translation.
Decision to grant a European patent for EP App. Ser. No. 01976786.2, dated Feb. 1, 2007, 2 pages.
Decision to grant a European patent for EP App. Ser. No. 04025700.8, dated Jun. 5, 2008, 2 pages.
Decision to grant a European patent for EP App. Ser. No. 05783232.1, dated Mar. 19, 2009, 2 pages.
Decision to grant a European patent for EP App. Ser. No. 06023078.6, dated Dec. 4, 2008, 2 pages.
Decision to Grant Patent in EP App. Ser. No. 05719973.9, dated Jun. 1, 2012, 1 page.
Decision to Grant Patent in EP App. Ser. No. 07805959.9, dated Nov. 4, 2011, 2 pages.
Decision to Grant Patent in JP App. Ser. No. 2007-532099, dated Jan. 8, 2008, 5 pages (with English translation).
Decision to Grant Patent in JP App. Ser. No. 2008-530917, dated Jan. 15, 2013, 6 pages (with English translation).
Decision to Grant Patent in JP App. Ser. No. 2008-532065, dated Nov. 13, 2012, 6 pages (with English translation).
Decision to Grant Patent in JP App. Ser. No. P2009-510543, dated Feb. 2, 2010, 6 pages (with English translation).
Deficiencies in sequence listing for EP App. Ser. No. 06023078.6, dated Dec. 5, 2006, 3 pages.
Demand for Appeal Trial filed in JP App. Ser. No. 2008-532141, filed Jul. 5, 2013, 10 pages (with English translation).
Deplanque et al., "Anti-Angiogenic Agents: Clinical Trial Design and Therapies in Development," European Journal of Cancer, 36:1713-1724 (2000).
Dermer, "Another Anniversary for the War on Cancer," Bio/Technology, 12:320 (1994).
Di Lorenzo et al., "Targeted Therapy in the Treatment of Metastatic Renal Cell Cancer", Oncology, 77(Suppl.1):122-131 (2010).
Di Raimondo et al., "Antiogenic Factors in multiple myeloma: higher levels in bone than in peripheral blood," Haematologica, 85:800-805 (2000).
Dias et al., "IL-12 Regulates VEGF and MMPs in a Murine Breast Cancer Model", International J. Cancer., 78, 361-5, 1998.
Dietrich, "BRAF Inhibition in Refractory Hairy-Cell Leukemia," N Eng J Med., 366(21):2038-2040 (May 24, 2012).
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
EP Communication under Rule 71(3) EPC for Application No. 06832529.9 issued on Nov. 25, 2011, 35 pages.
EP07806561.2 Office Action issued on Dec. 9, 2011, 5 pages.
EP07806561.2 Office Action issued on Feb. 7, 2011, 1 page.
EP07806561.2 Office Actions issued on Jan. 19 and Feb. 7, 2011.
EP07806561.2 Response to Office Action filed on Aug. 9, 2011, 134 pages.
Erber et al., "Combined inhibition of VEGF and PDGF signaling enforces tumor vessel regression by interfering with pericyte-mediated endothelial cell survival mechanisms," Faseb J., 18(2):338-340 (2004).
Erdem et al, "Correlation of E-cadherin, VEGF, COX-2 expression to prognostic parameters in papillary thyroid carcinoma", Experimental Mole Pathol., 90:312-317, Feb. 16, 2011.
European Office Action for App. Ser. No. 04719054.1, issued on Oct. 30, 2009, 5 pages.
European Office Action for App. Ser. No. 04807580.8, issued on Apr. 18, 2011, 11 pages.
European Office Action for App. Ser. No. 04807580.8, issued on Dec. 3, 2010, 7 pages.
European Office Action for App. Ser. No. 04807580.8, issued on Oct. 25, 2011, 17 pages.
European Office Action for App. Ser. No. 04818213.3, issued on Feb. 2, 2012, 5 pages.
European Office Action for App. Ser. No. 07743994.1, issued on Oct. 10, 2012, 8 pages.
European Office Action for App. Ser. No. 4025700.8, issued on Apr. 10, 2006, 3 pages.
European Office Action for App. Ser. No. 06832529.9 issued on Oct. 15, 2009, 1 page.
European Office Action App. Ser. No. 06832529.9 issued on Sep. 12, 2011, 3 pages.
European Response to EESR directed at Appl. No. 07743994.1-2123 filed on Nov. 23, 2010, 22 pages.
European Response to Office Action for Application No. 06832529.9 filed on Apr. 22, 2010, 82 pages.
European Response to Office Action for Application No. 06832529.9 filed on Oct. 4, 2011, 27 pages.
European Search Report dated Jul. 23, 2010 for European application No. 06782407, 8 pages.
European Search Report dated May 4, 2010 for European Application No. 07743994, 9 pages.
European Search Report directed at application No. 06768437.3, issued on Oct. 11, 2010, 10 pages.
European Search Report directed at application No. 06782407.8, issued on Jul. 23, 2010.
European Search Report directed at application No. 06832529.9, issued on Jul. 29, 2009, 6 pages.
European Search Report directed at application No. 06833681.7, issued on Nov. 24, 2010, 15 pages.
European Search Report directed at application No. 07806561.2, issued on Jan. 19, 2011, 16 pages.

(56) References Cited

OTHER PUBLICATIONS

European Search Report directed at application No. 10015141.4, issued on Sep. 9, 2011, 6 pages.
European Search Report for App. Ser. No. 03791389.4, issued on Jul. 7, 2011, 5 pages.
European Search Report for App. Ser. No. 04025700.8, dated Jan. 13, 2005, 3 pages.
European Search Report for App. Ser. No. 04719054.1, issued on Apr. 17, 2009, 4 pages.
European Search Report for App. Ser. No. 04818213.3, issued on Jul. 30, 2007, 3 pages.
European Search Report for App. Ser. No. 05783232.1, issued on Sep. 7, 2007, 5 pages.
European Search Report for App. Ser. No. 06023078.6, issued on Mar. 16, 2007, 5 pages.
European Search Report for App. Ser. No. 06767145.3, issued on May 23, 2011, 7 pages.
European Search Report for App. Ser. No. 10809938.3, issued on Jan. 2, 2013, 5 pages.
European Search Report for EP 08704376.6 dated Jun. 14, 2012, 12 pages.
Examination Report dated Feb. 18, 2005 for NZ App. Ser. No. 525324, 1 page.
Examination Report dated Feb. 21, 2008 for AU App. Ser. No. 2006203099, 2 pages.
Examination Report dated Jan. 30, 2013 for AU App. Ser. No. 2009210098, 10 pages.
Examination Report dated Mar. 26, 2008 for AU App. Ser. No. 2006236039, 2 pages.
Examination Report dated May 4, 2006 for AU App. Ser. No. 2001295986, 2 pages.
Examination Report dated Nov. 24, 2012 for AU App. Ser. No. 2008325608, 3 pages.
Examination Report dated Oct. 13, 2003 for NZ App. Ser. No. 525324, 2 pages.
Examination Report dated Sep. 2, 2004 for NZ App. Ser. No. 525324, 1 page.
Examination Report dated Sep. 20, 2005 for AU App. Ser. No. 2001295986, 3 page.
Examination report from EP 040257008 mailed Apr. 10, 2006, 3 pages.
Examination Report in AU App. Ser. No. 2005217325, dated Aug. 1, 2007, 2 pages.
Examination Report in AU App. Ser. No. 2005217328, dated Aug. 1, 2007, 2 pages.
Examination Report in AU App. Ser. No. 2007288793, dated Dec. 22, 2011, 2 pages.
Examination Report in AU App. Ser. No. 2007289787, dated Nov. 25, 2011, 2 pages.
Examination Report in AU App. Ser. No. 2008217931, dated Jun. 28, 2012, 3 pages.
Examination Report in PK App. Ser. No. 155/2005, dated Mar. 11, 2009, 2 pages.
Experimental Medicine, Supplementary Volume, "A New Handbook of Genetic Engineering", Section 4, Yodosha, 2003(Japanese).
Explanation of Circumstances Concerning Accelerated Examination filed May 10, 2012 for JP Patent Application No. 2011-527665, 21 pages (with English Translation).
Extended European Search Report dated Feb. 21, 2013 for EP App. Ser. No. 12195436.6, 8 pages.
Extended European Search Report for App. Ser. No. 08846814.5, issued on Jun. 18, 2012, 11 pages.
Extended European Search Report in EP App. Ser. No. 06796594.7, dated Sep. 7, 2011, 5 pages.
Extended European Search Report in EP App. Ser. No. 07793075.8, dated Sep. 8, 2010, 6 pages.
Extended European Search Report in EP App. Ser. No. 07805959.9, dated Nov. 16, 2010, 6 pages.
Extended European Search Report in EP App. Ser. No. 08711837.8, dated Mar. 28, 2011, 5 pages.
Extended European Search Report in EP App. Ser. No. 09713617.0, dated Apr. 28, 2011, 5 pages.
Extended European Search Report mailed on Dec. 7, 2012 issued in connection with Corresponding European Application No. 06797249.7, 6 pages.
Extended Search Report in EP App. Ser. No. 12786619.2, dated Nov. 25, 2014, 6 pages.
Ezzat et al., "Dual Inhibition of RET and FGFR4 Retains Medullary Thyroid Cancer Cell Growth," Clinical Cancer Research, Feb. 2005, 11:1336-1341.
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
Final Office Action for U.S. Appl. No. 12/092,539 issued on May 9, 2011, 10 pages.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
First Office Action issued on Mar. 6, 2012 for the corresponding JP application, JP2007-542863, 17 pages and English translation.
FMC BioPolymer; http://www.Fmcbiopolymer.com/portals/pharm/contect/docs/fmc_alubra_brochurefinal.pdf; accessed Mar. 16, 2015, 6 pages.
Folkman et al., "Angiogenesis," The Journal of Biological Chemistry, 267(16):10931-10934 (1992).
Folkman et al., "Seminars in Medicine of the Beth Israel Hospital, Boston: Clinical Applications of Research on Angiogenesis," The New England Journal of Medicine, 333(26):1757-1763 (1995).
Folkman et al., "What is the Evidence That Tumors are Angiogenesis Dependent?," Journal of the National Cancer Institute, 82(1):4-6 (1990).
Folkman, "New Perspective in Clinical Oncology From Angiogenesis Research," J. Eur. J. Cancer, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," International Journal of Pharmaceutics, 126:199-208 (1995).
Formality Requirement dated Jun. 18, 2003 for PH App. Ser. No. 1-2003-500266, 3 pages.
Freshney, R. Ian, "Culture of Animal Cells, A Manual of Basic Technique," Alan R. Liss, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "Angiogenesis Inhibitor/Kekkan Shinsei Sogaiyaku," Clin Gastroenterol., May 25, 2004, 19:220-227.
Fujii et al., "MP-412, a dual EGFR/HER2 tyrosine kinase inhibitor: 2. In vivo antitumor effects," Am. Assoc. Cancer Research, A3394, 2005, 2 pages.
Funahashi et al., "P-2123, Lenvatinib treatment of differentiated thyroid cancer (DTC): Analysis to identify biomarkers associated with response," The 71$^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," J. Clin. Invest., 92:1736-1744 (1993).

(56) References Cited

OTHER PUBLICATIONS

Furitsu et al., "Stable medicinal compositions of quinolinecarboxamide derivative," Database Caplus Chemical Abstracts Service, Columbus, OH, US (2006) (XP002520305), 11 pages.
Furuta et al., "Synthesis and Biological Evaluation of Selective Inhibitors of PDGF Receptor Auto Phosphorylation," #64, American Chemical Society, 226$^{th}$ ACS National Meeting, New York, NY (Sep. 7-11, 2003), 72 pages.
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," Acta Chimica Hungarica, 112(2):241-247 (1983).
Gardner et al., "In Vitro Activity Sorghum-Selective Fluorophenyl Urea Herbicides," Pesticide Biochemistry and Physiology, 24(3):285-297 (1985).
Gatzemeier et al., "Phase III comparative study of high-dose cisplatin versus a combination of paclitaxel and cisplatin in patients with advanced non-small-cell lung cancer," J. Clin. Oncol., 18(19):3390-3399 (2000).
Genitourinary Cancers, Prostate Cancer Genitourinary, http://www.merkmanuals.com/professional/print/sec17/ch241/ch241e.html Mar. 16, 2011, 7 pages.
Gild et al, "Multikinase inhibitors: a new option for the treatment of thyroid cancer", Nature Reviews Endocrinol., 7:617-624, Oct. 2011.
Giles, "The vascular endothelial growth factor (VEGF) signaling pathway: a therapeutic target in patients with hematologic malignancies," Oncologist, 6(suppl 5):32-39 (2001).
Gingrich et al., "A New Class of Potent Vascular Endothelial Growth Factor Receptor Tyrosine . . .Clinical Candidate CEP-7055", Journal of Medicinal Chemistry., 46: 5375-88, 2003.
Glen "Pre-clinical investigation and clinical development of E7080, a multi-targeted tyrosine inhibitor: implications for melanoma," Ph.D. thesis submitted to the Faculty of Medicine, Division of Cancer Sciences and Molecular Pathology, University of Glasgow, Aug. 2010, 2 pages.
Goede, "Identification of serum angiopoietin-2 as a biomarker—for clinical outcome of colorectal cancer patients treated with bevacizumab-containing therapy," British Journal of Cancer, Oct. 2010, 103(9):1407-1414.
Golkar et al., "Mastocytosis," Lancet, 349:1379-1385 (1997).
Gould, "Salt Selection for Basic Drugs," International Journal of Pharmaceutics, 33:201-217, (1986) (XP025813036).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, pp. 1125-1132, 2005.
Gura, "Cancer Models Systems for Identifying new drugs are often faulty," Science, 278:1041-1042 (1997).
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Haleblian,"Characterization of habits and crystalline modification of solids and their pharmaceutical applications," J. Pharm. Sci., 64(8):1269-1288 (1975).
Haller, "Chemotherapy for advanced pancreatic cancer," Int. J. Radiation Oncol. Biol. Phys., 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).

Hara et al., "Amplification of c-myc, K-sam, and c-met in Gastric Cancers: Detection by Fluorescence In Situ Hybridization", Laboratory Investigation, 78, 1143-1153, 1998.
Hattori et al., "Immunohistochemical detection of K-sam protein in stomach cancer," Clin. Cancer Res., 2(8):1373-1381 (1996).
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Hayamo et al., "Pericytes in experimental MDA-MB231 tumor angiogenesis," Histochemistry and Cell Biology, 117(6):527-534, Abstract (Jun. 2002).
Hayek et al., "An in Vivo Model for Study of the Angiogenic Effects of Basic Fibroblast Growth Factor," Biochemical and Biophysical Research Communications, 147(2):876-880 (1987).
Haymo et al., "Pericytes in experimental MDA-MB231 tumor angiogenesis," Histochemistry and Cell Biology, 117(6):527-534 (2002) (abstract).
Hearing Notice issued May 4, 2012, in India Patent Application No. 383/CHENP/2008.
Heinemann, V., et al., "Comparison of the Cellular Pharmacokinetics and Toxicity of . . .1-beta-d-Arabinofuranosylcytosine", Cancer Research, 48, 4024-4031, 1988.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Heinrich et al, "Inhibition of c-kit receptor tyrosine kinase activity by STI 571, a selective tyrosine kinase inhibitor," Blood, 96(3):925-932 (2000) (XP001097629).
Heinrich et al., "Inhibition of KIT tyrosine kinase activity: a novel molecular approach to the treatment of KIT-positive malignancies," J. Clin. Oncol., 20(6):1692-1703 (2002).
Helfrich et al., "Angiopoietin-2 Levels Are Associated with Disease—Progression in Metastatic Malignant Melanoma," Clinical Cancer Research, Feb. 2009, 15(4):1384-1392.
Hennequin et al., "Design and Structure-Activity Relationship of a New Class of Potent VEGF Receptor Tyrosine Kinase Inhibitors", Journal of Medicinal Chemistry., 42: 5369-5389, 1999.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.
Hertel LW., et al., "Evaluation of the Antitumor Activity of Gemcitabine (2',2' -Difluoro-2'-deoxycytidine)", Cancer Research, 50, 4417-4422, 1990.
Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012).
Hines et al., "Coexpression of the c-kit and Stem Cell Factor Genes in Breast Carcinomas," Cell Growth & Differentiation, 6:769-779 (1995).
Hogaboam et al., "Novel Role of Transmembrane SCF for Mast Cell Activation and Eotaxin Production in Mast Cell-Fibroblast Interactions," J. Immunol., 160:6166-6171 (1998).
Hon et al., "Suppression of Solid Tumor Growth by Immunoneutralizing Monoclonal Antibody against Human Basic Fibroblast Growth Factor", Cancer Research, 51, 6180-4, 1991.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hurwitz et al., "Bevacizumab plus irinotecan, fluorouracil, and leucovorin for metastatic colorectal cancer," N. Engl. J. Med., 350(23):2335-2342 (2004).

(56) References Cited

OTHER PUBLICATIONS

Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al., "Changes in Phenotype and Proliferative Potential of Human Acute Myeloblastic Leukemia Cells in Culture with Stem Cell Factor," Experimental Hematology, 21:1686-1694 (1993).
Ikeda et al., "Expression and Functional Role of the Proto-Oncogene c-kit in Acute Myeloblastic Leukemia Cells," Blood, 78(11):2962-2968 (1991).
Ikota et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov. 24, 2009, 15(23):7229-7237.
Inai et al, "Inhibition of vascular endothelial growth factor (VEGF) signaling in cancer causes loss of endothelial fenestrations, regression of tumor vessels, and appearance of basement membrane ghosts," American Journal of Pathology, 165:35-52 (2004).
Indian Office Action for App. Ser. No. 1571/CHENP/2007, issued on Oct. 30, 2012, 2 pages.
Indian Office Action for IN App. Ser. No. 383/CHENP/2008, issued on May 3, 2012, 2 pages.
Indian Office Action in App. Ser. No. 6415/CHENP/2008, dated Oct. 3, 2013, 2 pages.
Indian Patent Application No. 2572/CHENP/2006 filed Jul. 13, 2006, 1 page.
Information about decision on request for EP App. Ser. No. 06023078.6, dated Mar. 21, 2007, 1 page.
Inoue et al., "Molecular Target Therapy Targeting Angiogenesis Pathways," The Nishinihon Journal of Urology, 66:425-432 (2004).
International Preliminary Report in International App. Ser. No. PCT/IB2008/003880, dated Aug. 11, 2009, 4 pages.
International Preliminary Report in International App. Ser. No. PCT/JP2007/066185, dated Mar. 5, 2009, 6 pages.
International Preliminary Report in International App. Ser. No. PCT/JP2007/066635, dated Mar. 12, 2009, 9 page.
International Preliminary Report in International App. Ser. No. PCT/JP2008/053066, dated Sep. 11, 2009, 12 pages.
International Preliminary Report in International App. Ser. No. PCT/JP2008/071881, dated Jul. 14, 2011, 7 pages pages.
International Preliminary Report in International App. Ser. No. PCT/JP2009/0524001, dated Oct. 14, 2010, 5 pages.
International Preliminary Report in Patentability in International App. Ser. No. PCT/JP2006/316331, dated Feb. 26, 2008, 5 pages.
International Preliminary Report on Patentability for App. Ser. No. PCT/JP2012/057949, dated Oct. 10, 2013, 7 pages.
International Preliminary Report on Patentability for International Application No. PCT/JP2001/09221, dated Jan. 8, 2003, 9 pages.
International Preliminary Report on Patentability for International Application No. PCT/JP2003/010964 dated Aug. 10, 2004, 7 pages.
International Preliminary Report on Patentability for International Application No. PCT/JP2004/003087, issued on Feb. 13, 2006, 5 pages.
International Preliminary Report on Patentability for International Application No. PCT/JP2005/016941, dated on Mar. 20, 2007, 10 pages.
International Preliminary Report on Patentability for International Application No. PCT/JP2006/312487, issued on Dec. 24, 2007, 7 pages.
International Preliminary Report on Patentability for International Application No. PCT/JP2007/060560 on Nov. 18, 2008, 6 pages with English translation.
International Preliminary Report on Patentability for International Application No. PCT/JP2007/060560, dated Dec. 10, 2008, 7 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability for International Application No. PCT/JP2008/051697, issued on Aug. 4, 2009, 18 pages.
International Preliminary Report on Patentability for International Application No. PCT/JP2008/070321, issued May 11, 2010, 15 pages with English translation.
International Preliminary Report on Patentability for International Application No. PCT/JP2009/051244 issued on Aug. 31, 2010, 12 pages (with English translation).
International Preliminary Report on Patentability for International Application No. PCT/JP2010/063804 dated Mar. 13, 2012, 6 pages.
International Preliminary Report on Patentability for International Application No. PCT/JP2011/064430, dated Jan. 24, 2013, 6 pages.
International Preliminary Report on Patentability in International App. No. PCT/JP2013/084052, dated Jul. 2, 2015, 7 pages.
International Preliminary Report on Patentability in International App. Ser. No. PCT/JP2005/003701, dated Sep. 16, 2006, 7 pages.
International Preliminary Report on Patentability in International App. Ser. No. PCT/JP2005/003704, dated Sep. 19, 2006, 7 pages.
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
International Preliminary Report on Patentability in International Application No. PCT/JP2006/315563 dated Feb. 5, 2008, 10 pages with English translation.
International Preliminary Report on Patentability in International Application No. PCT/JP2006/315698 dated Feb. 5, 2008, 17 pages English translation.
International Preliminary Report on Patentability in International Application No. PCT/JP2006/322514 issued on May 7, 2008, 8 pages.
International Preliminary Report on Patentability in International Application No. PCT/JP2006/322516 issued on May 7, 2008, 8 pages.
International Preliminary Report on Patentability in PCT App. Ser. No. PCT/US2012/040183, dated Apr. 3, 2014, 9 pages.
International Search Report and Written Opinion for PCT Application No. PCT/JP2011/064430, Sep. 13, 2011, 8 pages.
International Search Report and Written Opinion dated Sep. 14, 2010 for International Application No. PCT/JP2010/063804, 11 pages.
International Search Report and Written Opinion in International App. Ser. No. PCT/JP2008/071881, dated Jan. 27, 2009, 12 pages.
International Search Report and Written Opinion in International App. Ser. No. PCT/JP2009/0524001, dated Mar. 10, 2009, 9 pages.
International Search Report dated Apr. 1, 2008 for International Application No. PCT/JP2008/051024, 6 pages.
International Search Report dated Jan. 20, 2009 for International Application No. PCT/JP2008/070321, 8 pages.
International Search Report dated Jan. 23, 2007 for International Application No. PCT/JP2006/322514, 10 pages.
International Search Report dated Jan. 23, 2007 for International Application No. PCT/JP2006/323881, 6 pages.
International Search Report dated Mar. 24, 2009 for International Application No. PCT/JP2009/051244, 6 pages.
International Search Report dated Mar. 4, 2008 for International Application No. PCT/JP2008/051697, 7 pages.
International Search Report dated Nov. 20, 2007 for International Application No. PCT/JP2007/067088, 6 pages.
International Search Report dated Oct. 17, 2006 for International Application No. PCT/JP2006/315698, 5 pages.
International Search Report dated Sep. 11, 2007 for International Application No. PCT/JP2007/060560, 6 pages.
International Search Report dated Sep. 4, 2007 for International Application No. PCT/JP2007/063525, 7 pages.
International Search Report dated Sep. 5, 2006 for International Application No. PCT/JP2006/315563, 2 pages.
International Search Report for App. U.S. Appl. No. PCT/JP2005/016941, dated on Nov. 15, 2005, 4 pages.

(56) References Cited

OTHER PUBLICATIONS

International Search Report for International Application No. PCT/JP2001/09221, issued on Jan. 15, 2002, 9 pages.
International Search Report for International Application No. PCT/JP2004/003087, issued on Jul. 13, 2004, 3 pages.
International Search Report for International Application No. PCT/JP2006/317307, issued on Dec. 12, 2006, 3 pages.
International Search Report for PCT/JP2012/060279, May 29,2012, 5 pages.
International Search Report in International App. Ser. No. PCT/IB2008/003880, dated Aug. 11, 2009, 7 pages.
International Search Report in International App. Ser. No. PCT/JP2005/003701, dated May 31, 2005, 6 pages (with English translation).
International Search Report in International App. Ser. No. PCT/JP2005/003704, dated May 31, 2005, 6 pages (with English translation).
International Search Report in International App. Ser. No. PCT/JP2006/316331, dated Oct. 17, 2006, 5 pages (with English translation).
International Search Report in International App. Ser. No. PCT/JP2007/066185, dated Sep. 25, 2007, 4 pages.
International Search Report in International App. Ser. No. PCT/JP2007/066635, dated Oct. 16, 2007, 5 pages.
International Search Report in International App. Ser. No. PCT/JP2008/053066, dated May 20, 2008, 8 pages.
International Search Report in International Application No. PCT/JP2006/322516 issued on Jan. 23, 2007, 5 pages.
International Search Report in International Application No. PCT/JP2013/084052, dated Mar. 4, 2014, 2 pages.
Interview Summary in U.S. Appl. No. 12/558,982, dated Oct. 20, 2011, 3 pages.
Invitation to declare maintenance of the application for EP App. Ser. No. 01976786.2, dated Jul. 12, 2004, 1 page.
Invitation to declare maintenance of the application for EP App. Ser. No. 05783232.1, dated Sep. 25, 2007, 1 page.
Invitation to declare maintenance of the application for EP App. Ser. No. 06023078.6, dated May 2, 2007, 1 page.
Israel 200090 Office Actions issued on Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 issued on Jan. 26, 2010, 4 pages with English translation.
Israel Office Action directed at Appl. No. 205512 issued on Nov. 13, 2011, 4 pages with English translation.
Israel Response (IDS List) to Office Action directed at Appl. No. 195282 filed on May 3, 2010, 6 pages with English translation.
Israeli Office Action dated Mar. 27, 2012 for Israeli Application No. 189589, 3 pages with English translation.
Israeli Office Action for App. Ser. No. 155447, issued on Oct. 16, 2007, 3 pages (with English translation).
Israeli Office Action for App. Ser. No. 189677, issued on Feb. 18, 2009, 2 pages (with English translation).
Israeli Office Action for App. Ser. No. 195282, issued on Feb. 5, 2012, 3 pages (with English translation).
Israeli Office Action for App. Ser. No. 199907, issued on Apr. 22, 2012, 3 pages (with English translation).
Israeli Office Action issued on May 16, 2010 for corresponding Israeli Application No. 189589, 3 pages with English translation.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 5 pages.
Issue Notification in U.S. Appl. No. 12/558,982, dated Sep. 26, 2012, 1 page.
Issued Notification in U.S. Appl. No. 11/892,785, dated Aug. 18, 2010, 1 page.
Itoh et al., "Preferential alternative splicing in cancer generates a K-sam messenger RNA with higher transforming activity," Cancer Res., 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," Endocrinology, 133(2):848-859 (1993).
Jang et al., "Mutations in Fibroblast Growth Factor Receptor 2 and Fibroblast Growth Factor Receptor 3 Genes Associated with Human Gastric and Colorectal Cancers", Cancer Research,61:3541-3543 (2001).
Japanese Allowance for App. Ser. No. P2005-515330, issued on Apr. 21, 2009, 2 pages.
Japanese Allowance for App. Ser. No. P2005-516605, issued on Dec. 7, 2010, 5 pages (with English translation).
Japanese Classification of Gastric Carcinoma "Igan-Toriatsukai Kiyaku" (Jun. 1999, 13th ed.) and an English translation, 10 pages.
Japanese Decision to Grant a Patent dated Jan. 30, 2013 for Japanese Application No. 2007-533350, 3 pages with English translation.
Japanese Notice of Reasons for Rejection dated May 15, 2012 for Japanese Application No. 2007-533350, 6 pages with English translation.
Japanese Office Action dated Apr. 11, 2005 for App. Ser. No. 2002-536056, 6 pages (with English translation).
Japanese Office Action for App. Ser. No. 2005-516605, issued on Jun. 1, 2010, 3 pages.
Japanese Office Action for App. Ser. No. 2005-516605, issued on Nov. 4, 2009, 7 pages (with English translation).
Japanese Office Action for App. Ser. No. 2007-522356, issued on Feb. 8, 2011, 5 pages (with English translation).
Japanese Office Action for App. Ser. No. P2008-516724, issued on Oct. 9, 2012, 6 pages (with English translation).
Jhiang, "The RET proto-oncogene inn human cancers," Oncogene, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," J. Clin. Endocrinol. Metab., 89:4142-4145 (2004).
Joao et al., "Somatic trinucleotide change encompassing codons 882 and 883 of the RET proto-oncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Paclitaxel plus carboplatin in advanced non-small-cell lung cancer: a phase II trial," J. Clin. Oncol., 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," Eur. J. Cancer, 38:1133-1140 (2002).
Juurikivi et al , "Inhibition of c-kit tyrosine kinase by imatinib mesylate induces apoptosis in mast cells in rheumatoid synovia: a potential approach to the treatment of arthritis," Ann Rheum. Dis., 64:1126-1131 (2005).
Kanai et al., "Development Status and Future Prospects of Novel Molecular Target Drugs for Hepatocellular Carcinoma", Journal of the Japanese Society of Gastroenterology, 106:1727-1735 (2009).
Kanai et al., "Current status and future perspective of molecular targeted therapy for hepatocellular carcinoma," Journal of the Japanese Society of Gastroenterology, 106:1727-1735 (2009) (English translation).

(56) References Cited

OTHER PUBLICATIONS

Kanakura et al., "Expression, Function and Activation of the Proto-Oncogene c-kit Product in Human Leukemia Cells," Leukemia and Lymphorma, 10:35-41 (1993).

Kashuk et al., "Phenotype-genotype correlation in Hirschsprung disease is illuminated by comparative analysis of the RET protein sequence," PNAS, 102(25):8949-8954 (2005).

Kawano et al., "Presentation Abstract, Abstract Number; 1619, Combination of VEGFR inhibitor lenvatinib (E7080) and Met/EphB4inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.

Kay et al., "Eosinophils and Eosinophil-Associated Cytokines in Allergic Inflammation," Int. Arch. Allergy Immunol , 113:196-199 (1997).

Kelly et al., "Randomized phase III trial of paclitaxel plus carboplatin versus vinorelbine plus cisplatin in the treatment of patients with advanced non--small-cell lung cancer: a Southwest Oncology Group trial," J Clin. Oncol., 19(13):3210-3218 (2001).

Kibbe, Handbook of Pharmaceutical Excipients. Third Edition, 2000, pp. 6-1 through 6-6.

Kim et al., "RET Oligonucleotide Microarray for the Detection of RET Mutations in Multiple Endocrine Neoplasia Type 2 Syndromes", Clinical Cancer Research, 8,457-463, (2002).

Kim et al., "A phase II study of irinotecan plus cisplatin for patients with advanced stage IIIB or IV NSCLC previously treated with nonplatinum-based chemotherapy," Cancer, 107(4):799-805 (2006).

Kim et al., "An orally administered multitarget tyrosine kinase inhibitor, SU11248, is a novel potent inhibitor of thyroid oncogenic RET/papillary thyroid cancer kinases," J. Clin. Endocrinol. Metlab., 91(10):4070-4076 (2006).

Kim, "Technology evaluation: Matuzumab, Merck KGaA", Curr Opin Mol Ther. 2004; 6(1):96-103.

Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.

Kitamura et al., "Regulation of Development, Survival and Neoplastic Growth of Mast Cells through the c-kit Receptor," Int. Arch Allergy Immunol , 107:54-56 (1995).

Kitteringham et al., "A Simple Method for the Synthesis of Unsymmetrical Ureas," Synthetic Communications, 30(11):1937-1943 (2000).

Kleespies et al., "Tyrosine kinase inhibitors and gemcitabine: New treatment options in pancreatic cancer,?" Drug Resistance Updates, 9:1-18 (2006).

Klugbauer and Rabes, "The transcription coactivator HT1 F1 and a related protein are fused to the RET receptor tyrosine kinase in childhood papillary thyroid carcinomas", Oncogene, 18: 4388-4393 (1999).

Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).

Klugbauer et al., "Detection of a Novel Type of RET Rearrangement (PTC5) in Thyroid Carcinomas after Chernobyl and Analysis of the Involved RET -fused Gene RFG5", Cancer Research, 58:198-203 (1998).

Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.

Kolibaba et al., "Protein Tyrosine Kinases and Cancer," Biochimica et Biophysica Acta, 1333:F217-F248 (1997).

Korean ("KR") Notice of Allowance issued on Aug. 25, 2010 corresponding KR Application No. 10-2008-7005195, 3 pages with English translation.

Korean ("KR") Office Action issued on Dec. 24, 2009 for corresponding KR Application No. 10-2008-7005195, 7 pages with English translation.

Korean ("KR") Office Action issued on May 29, 2010 for corresponding KR Application No. 10-2008-7005195, 6 pages with English translation.

Korean Office Action for App. Ser. No. 10-2003-7005506, issued on Jan. 5, 2006, 5 pages (with English translation).

Korean Office Action for App. Ser. No. 10-2005-7020292, issued on Dec. 8, 2005, 5 pages (with English translation).

Korean Office Action for App. Ser. No. 10-2006-7013993, issued on Jul. 31, 2007, 9 pages (with English translation).

Korean Office Action for App. Ser. No. 10-2007-7001347, issued on Apr. 27, 2012, 6 pages (with English translation).

Korean Office Action for App. Ser. No. 10-2007-7001347, issued on Sep. 28, 2011 (with English translation).

Korean Office Action for App. Ser. No. 10-2009-7005657, issued on Sep. 30, 2013, 27 pages (with English translation).

Korean Office Action in KR App. Ser. No. 10-2008-7029472, dated Sep. 30, 2013, 27 pages (with English translation).

Kotva et al., "Substances with Antineoplastic Activity, LIII. N-(δ-(4-Pyrrolo[2,3-d]Pyrimidinylthio) Valeryl]} Amino Acids and Analogous Derivatives of Di-and Triglycine," Collection Czechoslov. Chem. Commun., 38:1438-1444 (1973).

Koyama et al, "Anti-tumor effect of E7080, a novel angiogenesis inhibitor," *Folia Pharmacol. Japan.*, 2008, 132: 100-104 (with English translation).

Kremer, "Lenvatinib Advisory Board", The presentation document, American Society of Clinical Oncology, Annual meeting 2014, May 31, 2014, 138 pages.

Kruckeberg et al., "Pyrosequencing Technology as a Method for the Diagnosis of Multiple Endocrine Neoplasia Type 2", Clinical Chemistry, 50, 522-529, 2004.

Krystal et al., "Indolinone Tyrosine Kinase Inhibitors Block Kit Activation and Growth of Small Cell Lung Cancer Cells", Cancer Research., 61, 3660-3668, 2001.

Kubo et al., "A novel series of 4-phenoxyquinolines: potent and highly selective inhibitors of pdgf receptor autophosphorylation", Bioorganic and Medicinal Chemistry Letters., 7, 2935-2940, 1997.

Kubo et al., "Novel Potent Orally Active Selective VEGFR-2 Tyrosine Kinase Inhibitors: . . .ureas", Journal of Medicinal Chemistry., 48, 1359-1366, 2005.

Kumar et al., "Survival and Failure Outcomes in Primary Thyroid Lymphomas: A Single Centre Experience of Combined Modality Approach," Journal of Thyroid Research, vol. 2013, Jun. 18, 2013, 6 pages.

Kumar et al., "Discovery and biological evaluation of GW654652: A pan inhibitor of VEGF receptors," Proceedings of the American Association for Cancer Research, 44, 9, (Abstract 39), 2003, 2 pages.

Laird et al., "SU6668 Is a Potent Antiangiogenic and Antitumor Agent That Induces Regression of Established Tumors1", Cancer Research., 60, 4152-4160, 2000.

Lam et al., "High prevalence of RET proto-oncogene activation (RET/PTe) in papillary thyroid carcinomas", Eur J Endocrinology, 147: 741-745 (2002).

Lasota et al., "Mutations in Exons 9 and 13 of KIT Gene Are Rare Events in Gastrointestinal Stromal Tumors," American Journal of Pathology, 157(4):1091-1095 (2000).

LeDoussal et al. "Bispecific-antibody-mediated targeting of radiolabeled bivalent haptens: theoretical, experimental and clinical results", Int. J. Cancer Suppl. 7: 58-62, 1992.

Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.

Lennartsson et al., The Stem Cell Factor Receptor/c-Kit as a Drug Target in Cancer, Current Cancer Drug Targets, 6:561-571 (2006).

Lenvatinib in Wikipedia: The Free Encyclopedia, http://en/wikipeida/org/wiki/Lenvatinib (accessed Dec. 18, 2013), 2 pages.

Lesueur et al., "Polymorphisms in RET and its coreceptors and ligands as genetic modifiers of multiple endocrine neoplasia type 2A," Cancer Res., 66:1177-1180 (2006).

Leukemias, Hematology, and Oncology, http://www.merkmanuals.com/professional/print/sec11/ch14a.html Mar. 16, 2011, 5 pages.

(56) References Cited

OTHER PUBLICATIONS

Lev et al., "A Specific Combination of Substrates is Involved in Signal Transduction by the Kit-Encoded Receptor," The EMBO Journal, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).
Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).
Liu et al., "Structure of Human Methionine Aminopeptidase-2 Complexed with Fumagillin", Science., 282, 1324-1327, 1998.
Logie et al., "Activating mutations of the tyrosine kinase receptor FGFR3 are associated with benign skin tumors in mice and humans," Human Mol. Genet., 14:1153-1160 (2005).
Longley et al., "Altered Metabolism of Mast-Cell Growth Factor (c-kit Ligand) in Cutaneous Mastocytosis," The New England Journal of Medicine, 328(18):1302-1307 (1993).
Longley et al., "Classes of c-KIT activating mutations: proposed mechanisms of action and implications for disease classification and therapy," Leuk. Res., 25:571-576 (2001).
Longley et al., "Somatic c-KIT Activating Mutation in Urticaria Pigmentosa and Aggressive Mastocytosis: Establishment of Clonality in a Human Mast Cell Neoplasm," Nature Genetics, 12:312-314 (1996).
Lu et al., "Tailoring in Vitro Selection for a Picomolar Affinity Human Antibody Directed Against Vascular Endothelial Growth Factor Receptor 2 for Enhanced Neutralizing Activity," J Biol Chem., 2003, 278(44):43496-43507.
Lukacs et al., "Stem Cell Factor (c-kit Ligand) Influences Eosinophil Recruitment and Histamine Levels in Allergic Airway Inflammation," J. Immunol, 156:3945-3951 (1996).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Maintenance and Response to EP Search Report in EP App. U.S. Appl. No. 06796594.7, dated Dec. 21, 2011, 43 pages.
Maintenance of the application for EP App. Ser. No. 01976786.2, dated Sep. 6, 2004, 1 page.
Maintenance of the application for EP App. Ser. No. 05783232.1, dated Nov. 9, 2007, 1 pages.
Maintenance of the application for EP App. Ser. No. 06023078.6, dated Jun. 19, 2007, 1 page.
Marchetti et al., "Clinical Features and Outcome of Patients with Non-Small-Cell Lung Cancer Harboring BRAF Mutations," J Clin Oncol., 29(26):3574-3579 (Aug. 8, 2011).
Masferrer et al., "COX-2 Inhibitors A New Class of Antiangiogenic Agents", Annals of N.Y. Acad. Science., 889:84-6, 1999.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003), 1 page.
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003), 1 page (abstract only).
Matsui et al., "E7080, a novel inhibitor that targets multiple kinases, has potent antitumor activities against stem cell factor producing human small cell lung cancer H146, based on angionenesis inhibition," Int. J. Cancer, 122:664-671 (2008).
Matsui et al., "E7080, a novel multi-receptor Tyrosine Kinase Inhibitor, inhibited in vitro / in vivo VEGF- and SCF-driven angiogenesis SCLC cell line," Abstract #146, *EORTC-NCI-AACR*, Geneva, Switzerland (Sep. 28-Oct. 1, 2004).
Matsui et al., "E7080, a novel multi-receptor Tyrosine Kinase Inhibitor, inhibited in vitro / in vivo VEGF- and SCF-driven angiogenesis SCLC cell line," Abstract #146, EORTC-NCI-AACR, Geneva, Switzerland (Sep. 28-Oct. 1, 2004) (abstract only).
Matsui et al., "E7080, a novel multi-targeted tyrosine kinase inhibitor, exhibits anti-angiogenic activity via inhibition of KIT signaling in a small cell lung cancer xenograft model," Eur. J. Cancer, 2004, 2(8):47 (abstract only).
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., Asco Meeting Abstracts, Part 1, Abstract No: 8567, 2 pages.
Matsui et al., "Quantitative analysis of the profile of tumor vessels may be useful as predictive biomarkers for E7080," Abstract #4631, 98th AACR annual meeting, Los Angeles, CA, (Apr. 14-18, 2007), 1 page.
Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics*," Prague, Czech Republic (Nov. 7-10, 2006), 1 page.
Matsui, "Extracellular matrix of linitis plastica as a possible new therapeutic target," Surgical Treatment, Sep. 2003, 89(3):301-306 (with English translation).
Matsushima et al., "Preparation of pyridine and pyrimidine derivatives as inhibitors of hepatocyte growth factor receptor (HGFR)," Hcaplus, 2005, 977021.
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," Mol. Cancer Ther., 3(9):1041-1048 (2004).
McCulloch et al., "Astragalus-based Chinese herbs and platinum-based chemotherapy for advanced non-small-cell lung cancer: meta-analysis of randomized trials," J. Clin. Oncol., 24(3):419-430 (2006).
Meltzer, "The Pharmacological Basis for the Treatment of Perennial Allergic Rhinitis and Non-Allergic Rhinitis with Topical Corticosteroids," Allergy, 52:33-40 (1997).
Memorandum in Response to Office Action in IL App. Ser. No. 197141, dated Apr. 8, 2013, 18 pages (with English translation).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Clin. Cancer Res., 9:327-337 (2003).
Metcalfe et al., "Lineage Commitment in the Progeny of Murine Hematopoietic Preprogenitor Cells: Influence of Thrombopoietin and Interleukin 5," Proc. Nat'l Acad. Sci. USA, 95:6408-6412 (1998).
Metcalfe et al., "Mast cells," Physiol. Rev., 77(4):1033-1079 (1997).
Metcalfe, "Classification and Diagnosis of Mastocytosis: Current Status," J. Invest. Dermatol., 96:2S-4S (1991).
Mexican Office Action in App. U.S. Appl. No. MX/a/2010/008187, dated Aug. 21, 2013, 6 pages (with English translation).
Micke et al., "Characterization of c-kit expression in small cell lung cancer: prognostic and therapeutic implications," Clin. Cancer Res., 9:188-194 (2003).
Miknis et al., "AARY-334543, A potent, orally active small molecule inhibitor of EGFR and ErbB-2," Am. Assoc. Cancer Res. Abstract 3399, 2005, 2 pages.
Miller et al., "Genomic amplification of MET with boundaries within fragile site FRA7G and upregulation of MET pathways in esophageal adenocarcinoma," Oncogene, 2005, 25(3):409-418.

(56) References Cited

OTHER PUBLICATIONS

Miller et al., "Paclitaxel plus bevacizumab versus paclitaxel alone for metastatic breast cancer," N. Engl. J. Med., 357(26):2666-2676 (2007).
Milstein and Cuello, "Hybrid hybridomas and their use in immunohistochemistry", Nature 305: 537-9, 1983.
Mitchell et al, "The influence of additives on the cloud point, disintegration and dissolution of hydroxypropylmethylcellulose gels and matrix tablets," International journal of pharmaceutics, 1990, vol. 66, No. 1/3, pp. 233-242.
Miyauchi et al., "Two Germline Missense Mutations of Co dons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," AIMECS03, Kyoto, Japan (Oct. 14-17, 2003), 1 page.
Mohammadi et al., "Crystal structure of an angiogenesis inhibitor bound to the FGF receptor tyrosine kinase domain", Embo J., 17, 5896-5904, 1998.
Mologni et al., "Inhibition of RET tyrosine kinase by SU5416," J. Mol. Endocrinol., 37(2):199-212 (2006).
Montalbetti and Falque, "Tetrahedron report No. 740: Amide bond formation and peptide coupling," Tetrahedron, 2005, 61:10827-10852.
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 21(21):3955-3964 (2003).
Morikawa et al., "Angiogenesis and Pericytes," the Cell, 37(4):164-168 (2005) (English translation).
Morris et al., "An Integrated Approach to the Selection of optimal Salt Form for a New Drug Candidate," International Journal of Pharmaceutics, 105:209-217 (1994) (XP023724810).
Mototsugu, "mTOR inhibitors," Nippohn Rinsho, Jun. 2010, 68(6):1067-1072 (with English abstract).
Myers et al., "The Preparation and SAR of 4-(Anilino), 4-(Phenoxy), and 4-(Thiophenoxy)-Quinazolines: Inhibitors of p561ck and EGF-R Tyrosine Kinase Activity," Bioorgan. & Med. Chem. Letters, 7:417-420 (1997).
Naclerio et al., "Rhinitis and Inhalant Allergens," JAMA, 278(22):1842-1848 (1997).
Nagata et al., "Elevated Expression of the Proto-Oncogene c-kit in Patients with Mastocytosis," Leukemia, 12:175-181 (1998).
Nakagawa et al., "E7050: A dual c-Met and VEGFR-2 tyrosine kinase inhibitor promotes tumor regression and prolongs survival in mouse xengraft models," Cancer Sci., Jan. 2010, 101(1):210-215.
Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, AACR, Toronto, Canada (Apr. 5-9, 2003).
Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Nakazawa et al., "Maximizing the efficacy of anti-angiogenesis cancer therapy: A multi-targeting strategy by tyrosine kinase inhibitors,"
AACR Annual Meeting 2014, Presentation Abstract and Poster, Apr. 5-9, 2014, 2 pages (abstract only).
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Naran eta l., "Inhibition of HGF/MET as therapy for malignancy," Expert Opin. Ther. Targets, 2009, pp. 569-581.
Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).
Naski et al., "Graded activation of fibroblast growth factor receptor 3 by mutations causing achondroplasia and thanatophoric dysplasia," Nat. Genet., 13:233-237 (1996).
Natali et al., "Breast Cancer is Associated with Loss of the c-kit Oncogene Product," Int. J. Cancer, 52:713-717 (1992).
NCBI GenBank Accession No. NM_000222, Coffey et al. (Feb. 11, 2008), 7 pages.
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Nishikawa et al., "Cys611Ser mutation in RET proto-oncogene in a kindred with medullary thryroid carcinoma and Hirschsprung's disease", European Journal of Human Genetics, 11,364-368 (2003).
Nishio et al, "Phase 1 study of lenvatinib combined with carboplatin and paclitaxel in patients with non-small-cell lung cancer", British Journal of Cancer, 2013, 109:538-544.
Nocka et al., "Expression of c-kit gene products in known cellular targets of W mutations in normal and W mutant mice—evidence for an impaired c-kit kinase in mutant mice," *Cold Spring Harbor Laboratory Press*, 3:816-826 (1989) (XP002522472).
Non-Final Office Action in U.S. Appl. No. 10/577,531, mailed Sep. 23, 2008, 17 pages.
Non-Final Office Action in U.S. Appl. No. 10/797,903, mailed Aug. 20, 2009, 10 pages.
Non-Final Office Action in U.S. Appl. No. 10/797,903, mailed Dec. 11, 2007, 12 pages.
Noriyuki et al., "Anti-tumor effect of E7080, a novel angiogenesis inhibitor," Database BIOSIS [Online] Biosciences Information Service, Philadelphia, PA, US: Database accession no. PREV200800475929, Aug. 2008, XP002677323, 1 page.
Notice of Acceptance dated Aug. 10, 2004 for ZA Patent App. No. 2003/3567, 1 page.
Notice of Acceptance dated Aug. 3, 2006 for AU App. Ser. No. 2001295986, 4 pages.
Notice of Acceptance dated May 13, 2008 for AU App. Ser. No. 2006236039, 4 pages.
Notice of Acceptance for AU App. Ser. No. 2009210098, dated Jun. 4, 2013, 3 pages.
Notice of Acceptance in AU App. Ser. No. 2005217325, dated Nov. 20, 2007, 3 pages.
Notice of Acceptance in AU App. Ser. No. 2005217328, dated Sep. 24, 2007, 3 pages.
Notice of Acceptance in AU App. Ser. No. 2006282456, dated Aug. 17, 2009, 1 page.
Notice of Acceptance in AU App. Ser. No. 2007288793, dated Apr. 10, 2012, 3 pages.
Notice of Acceptance in AU App. Ser. No. 2007289787, dated Mar. 16, 2012, 3 pages.
Notice of Acceptance in DB App. Ser. No. 60/2005, dated Nov. 16, 2006, 1 page.
Notice of Acceptance in NZ App. Ser. No. 547517, dated Mar. 6, 2009, 1 page.
Notice of Acceptance in NZ App. Ser. No. 566793, dated Feb. 12, 2010, 2 pages.
Notice of Acceptance of Complete Specification dated Mar. 4, 2005 for NZ App. Ser. No. 525324, 1 page.
Notice of Allowability dated Nov. 28, 2007 for PH App. Ser. No. 1-2003-500266, 1 page.
Notice of Allowability in PH App. Ser. No. 1-2007-502319, dated Feb. 29, 2012, 1 page.

(56) References Cited

OTHER PUBLICATIONS

Notice of Allowance dated Apr. 19, 2005 for RU App. Ser. No. 2003114740, 79 pages (with English translation).
Notice of Allowance dated Apr. 19, 2011 for JP App. Ser. No. 2007-522356, 5 pages.
Notice of Allowance dated Apr. 24, 2012 for U.S. Appl. No. 12/524754, 10 pages.
Notice of Allowance dated Apr. 29, 2010 for AU App. Ser. No. 2005283422, 3 pages.
Notice of Allowance dated Aug. 2, 2005 for JP App. Ser. No. 2002-536056, 2 pages (with English translation).
Notice of Allowance dated Aug. 7, 2012 for Japanese App. Ser. No. P2007-529565, 6 pages (with English translation).
Notice of Allowance dated Dec. 15, 2006 for CN App. Ser. No. 01819710.8, 4 pages.
Notice of Allowance dated Dec. 26, 2007 for IL App. Ser. No. 155447, 2 pages (with English translation).
Notice of Allowance dated Feb. 15, 2013 for NZ App. Ser. No. 598291, 1 page.
Notice of Allowance dated Feb. 27, 2009 for U.S. Appl. No. 11/293,785, 4 pages.
Notice of Allowance dated Feb. 5, 2010 for CN App. Ser. No. 200580026468.7, 5 pages (with English translation).
Notice of Allowance dated Jul. 17, 2012 for JP App. Ser. No. P2011-527665, 4 pages (with English translation).
Notice of Allowance dated Jul. 21, 2009 for JP App. Ser. No. 2005-124034, 6 pages (with English translation).
Notice of Allowance dated Jun. 13, 2006 for U.S. Appl. No. 10/420,466, 2 pages.
Notice of Allowance dated Jun. 20, 2012 for EP App. Ser. No. 06782407.8, 35 pages.
Notice of Allowance dated Jun. 25, 2012 for EP App. Ser. No. 07806561.2, 7 pages.
Notice of Allowance dated Jun. 3, 2008 for U.S. Appl. No. 11/293,785, 6 pages.
Notice of Allowance dated Mar. 14, 2010 for IL App. Ser. No. 189677, 3 pages (with English translation).
Notice of Allowance dated Mar. 16, 2007 for U.S. Appl. No. 10/420,466, 3 pages.
Notice of Allowance dated Mar. 21, 2013 for EP App. Ser. No. 07793075.8, 2 pages.
Notice of Allowance dated Mar. 22, 2012 for U.S. Appl. No. 12/986,638, 12 pages.
Notice of Allowance dated Mar. 8, 2013 for CA App. Ser. No. 2627598, 1 page.
Notice of Allowance dated May 16, 2013 for EP App. Ser. No. 06796594.7, 2 pages.
Notice of Allowance dated May 18, 2009 for U.S. Appl. No. 11/293,785, 4 pages.
Notice of Allowance dated May 6, 2013 for EP App. Ser. No. 04818213.3, 22 pages.
Notice of Allowance dated Nov. 14, 2011 for IL App. Ser. No. 181697, 4 pages (with English translation).
Notice of Allowance dated Nov. 19, 2008 for U.S. Appl. No. 11/293,785, 4 pages.
Notice of Allowance dated Nov. 2, 2012 for EP App. Ser. No. 06782407.8, 2 pages.
Notice of Allowance dated Nov. 2, 2012 for EP App. Ser. No. 07806561.2, 2 pages.
Notice of Allowance dated Oct. 14, 2010 for CA App. Ser. No. 2426461, 1 page.
Notice of Allowance dated Oct. 17, 2011 for CA App. Ser. No. 2579810, 1 page.
Notice of Allowance dated Oct. 18, 2006 for MX App. Ser. No. PA/a/2003/003362, 4 pages (with English translation).
Notice of Allowance dated Oct. 20, 2008 for TW App. Ser. No. 90125928, 4 pages (with English translation).
Notice of Allowance dated Oct. 31, 2008 for NO App. Ser. No. 20031731, 4 pages (with English translation).
Notice of Allowance dated Oct. 9, 2010 for CN App. Ser. No. 200710007097.9, 4 pages (with English translation).
Notice of Allowance dated Oct. 9, 2012 for U.S. Appl. No. 12/524,754.
Notice of Allowance dated Sep. 12, 2005 for U.S. Appl. No. 10/420,466, 2 pages.
Notice of Allowance dated Sep. 20, 2011 for JP App. Ser. No. 2006-535174, 4 pages.
Notice of Allowance dated Sep. 25, 2012 for U.S. Appl. No. 12/986,638, 56 page.
Notice of Allowance dated Sep. 4, 2012 in JP App. Ser. No. P2009-123432, 5 pages (with English translation).
Notice of Allowance for CN App. Ser. No. 200980103218.7, dated May 27, 2013, 4 pages (with English translation).
Notice of Allowance for JP App. Ser. No. 2008-516724, dated Jan. 22, 2013, 4 pages, with English translation.
Notice of Allowance for JP App. Ser. No. P2008-532141, dated Sep. 10, 2013, 5 pages (with English translation).
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/741,682, dated Jun. 19, 2013, 10 pages.
Notice of Allowance for U.S. Appl. No. 12/524,754 dated Oct. 9, 2012, 36 pages.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in AU App. Ser. No. 2010285740, dated Nov. 19, 2014, 1 page.
Notice of Allowance in CA App. Ser. No. 2605854, dated Apr. 7, 2010, 1 page.
Notice of Allowance in CA App. Ser. No. 2652442, dated Apr. 16, 2014, 1 page.
Notice of Allowance in CA App. Ser. No. 2661333, dated Dec. 19, 2013, 1 page.
Notice of Allowance in CA App. Ser. No. 2661702, dated Sep. 26, 2013, 1 page.
Notice of Allowance in CA App. Ser. No. 2771403, dated Oct. 22, 2014, 1 page.
Notice of Allowance in CN App. Ser. No. 200680021939.X, dated Jan. 11, 2012, 4 pages (with English translation).
Notice of Allowance in CN App. Ser. No. 200780019200.X, dated Jan. 15, 2013, 4 pages (with English translation).
Notice of Allowance in CN App. Ser. No. 200780019520.5, dated Apr. 27, 2011, 4 pages (with English translation).
Notice of Allowance in CN App. Ser. No. 201180030568.2, dated Sep. 9, 2014, 4 pages (with English translation).
Notice of Allowance in CN App. Ser. No. 201280010898.X, dated Sep. 2, 2015, 4 pages (with English translation).
Notice of Allowance in EP App. Ser. No. 04807580.8, dated Dec. 15, 2014, 103 pages.
Notice of Allowance in EP App. Ser. No. 04818213.3, dated Sep. 19, 2013, 2 pages.
Notice of Allowance in EP App. Ser. No. 07743994.1, dated May 8, 2015, 51 pages.
Notice of Allowance in EP App. Ser. No. 08704376.6, dated Aug. 19, 2014, 62 pages.
Notice of Allowance in EP App. Ser. No. 08846814.5, dated Jan. 8, 2015, 36 pages.
Notice of Allowance in EP App. Ser. No. 10809938.3, dated Sep. 3, 2015, 30 pages.
Notice of Allowance in EP App. Ser. No. 11798224.9, dated Sep. 29, 2015, 37 pages.

(56) References Cited

OTHER PUBLICATIONS

Notice of Allowance in EP App. Ser. No. 12774278.1, dated Jun. 29, 2015, 34 pages.
Notice of Allowance in HU App. Ser. No. P0302603, dated Aug. 19, 2015, 5 pages (with English translation).
Notice of Allowance in ID App. Ser No. W-00 2008 00601, dated Oct. 17, 2012, 12 pages (with English translation).
Notice of Allowance in IL App. Ser. No. 195282, dated Aug. 11, 2014, 5 pages (with English translation).
Notice of Allowance in IL App. Ser. No. 197141, dated Oct. 27, 2013, 2 pages (with English translation).
Notice of Allowance in IL App. Ser. No. 200090, dated Nov. 18, 2013, 5 pages (with English translation).
Notice of Allowance in IL App. Ser. No. 205512, dated Feb. 15, 2015, 5 pages (with English translation).
Notice of Allowance in IL App. Ser. No. 207089, dated Nov. 10, 2014, 5 pages (with English translation).
Notice of Allowance in JP App. Ser. No. 2011-206481, dated Aug. 4, 2015, 7 pages (with English translation).
Notice of Allowance in JP App. Ser. No. P2009-540099, dated Oct. 21, 2014, 6 pages (with English translation).
Notice of Allowance in JP App. Ser. No. P2009-551518, dated Oct. 22, 2013, 5 pages (with English translation).
Notice of Allowance in KR App. Ser. No. 10-2006-7013907, dated Jan. 14, 2008, 3 pages (with English translation).
Notice of Allowance in KR App. Ser. No. 10-2006-7013940, dated Jan. 14, 2008, 3 pages (with English translation).
Notice of Allowance in KR App. Ser. No. 10-2008-7013685, dated Nov. 29, 2013, 3 pages (with English translation).
Notice of Allowance in KR App. Ser. No. 10-2008-7027527, dated Mar. 3, 2014, 4 pages (with English translation).
Notice of Allowance in KR App. Ser. No. 10-2008-7029472, dated Sep. 16, 2014, 3 pages (with English translation).
Notice of Allowance in KR App. Ser. No. 10-2009-7005657, dated Sep. 19, 2014, 3 pages (with English translation).
Notice of Allowance in KR App. Ser. No. 10-2009-7017694, dated Jul. 28, 2014, 3 pages (with English translation).
Notice of Allowance in KR App. Ser. No. 10-2010-7011023, dated Mar. 24, 2015, 3 pages (with English translation).
Notice of Allowance in KR App. Ser. No. 10-2010-7018835, dated Jan. 20, 2015, 3 pages (with English translation).
Notice of Allowance in KR App. Ser. No. 10-2012-7003846, dated Feb. 3, 2015, 3 pages.
Notice of Allowance in MX App. Ser. No. MX/a/2008/002156, dated Oct. 15, 2010, 3 pages (with English translation).
Notice of Allowance in MX App. Ser. No. MX/a/2010/008187, dated Jul. 17, 2014, 3 pages (with English translation).
Notice of Allowance in MX App. Ser. No. MX/a/2012/014776, dated Mar. 18, 2015, 3 pages (with English tranlsation).
Notice of Allowance in MX App. Ser. No. MX/a/2013/009931, dated Jun. 29, 2015, 3 pages.
Notice of Allowance in MY App. Ser. No. PI20071922, dated Jan. 15, 2010, 3 pages.
Notice of Allowance in PK App. Ser. No. 1024/2006, dated Nov. 2, 2010, 1 page.
Notice of Allowance in PK App. Ser. No. 375/2008, dated Nov. 2, 2010, 1 page.
Notice of Allowance in RU App. Ser. No. 2006134254, dated Jan. 14, 2008, 30 pages (with English translation).
Notice of Allowance in RU App. Ser. No. 2012103471, dated Dec. 19, 2014, 12 pages (with English translation).
Notice of Allowance in RU App. Ser. No. 2012158142, dated May 5, 2015, 15 pages (with English translation).
Notice of Allowance in TW App. Ser. No. 095130665, dated Sep. 7, 2012, 4 pages (with English translation).
Notice of Allowance in TW App. Ser. No. 100104281, dated Jun. 9, 2015, 4 pages (with English translation).
Notice of Allowance in UA App. Ser. No. a201203132, dated Mar. 21, 2014, 6 pages.
Notice of Allowance in U.S. Appl. No. 11/892,785, dated Apr. 5, 2010, 23 pages.
Notice of Allowance in U.S. Appl. No. 10/797,903, dated Mar. 10, 2011, 22 pages.
Notice of Allowance in U.S. Appl. No. 11/508,322, dated Sep. 15, 2009, 6 pages.
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 11/997,719, dated Jun. 5, 2014, 14 pages.
Notice of Allowance in U.S. Appl. No. 12/031,568, dated Jun. 1, 2012, 23 pages.
Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/439,339, dated Apr. 1, 2014, 17 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/524,754, dated Sep. 18, 2014, 35 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 12/741,682, dated Feb. 7, 2014, 11 pages.
Notice of Allowance in U.S. Appl. No. 12/741,682, dated May 15, 2014, 13 pages.
Notice of Allowance in U.S. Appl. No. 12/741,682, dated Oct. 21, 2013, 12 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/083,338, dated Feb. 6, 2014, 15 pages.
Notice of Allowance in U.S. Appl. No. 13/083,338, dated Jul. 10, 2014, 22 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in U.S. Appl. No. 13/624,278, dated Oct. 31, 2014, 14 pages.
Notice of Allowance in U.S. Appl. No. 13/624,278, dated Sep. 16, 2013, 20 pages.
Notice of Allowance in U.S. Appl. No. 13/805,826, dated Dec. 17, 2014, 15 pages.
Notice of Allowance in U.S. Appl. No. 13/983,891, dated Mar. 20, 2014, 9 pages.
Notice of Allowance in U.S. Appl. No. 14/002,018, dated Oct. 24, 2014, 70 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in VN App. Ser. No. 1-2008-00723, dated Aug. 19, 2010, 2 pages (with English translation).
Notice of Allowance in VN App. Ser. No. 1-2011-03484, dated Apr. 28, 2014, 2 pages.

(56) References Cited

OTHER PUBLICATIONS

Notice of Allowance in ZA App. Ser. No. 2007/09572, dated Mar. 12, 2009, 1 pages.
Notice of Allowance issued in CN App. Ser. No. 200880115011.7, dated Aug. 5, 2013, 4 pages (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 41 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Notice of decision for patent dated Apr. 17, 2006 for KR App. Ser. No. 10-2005-7020292, 4 pages (with English translation).
Notice of decision for patent dated Jun. 12, 2006 for KR App. Ser. No. 10-2003-7005506, 4 pages (with English translation).
Notice of Final Rejection in KR App. Ser. No. 10-2009-7013723, dated Jul. 29, 2011, 4 pages (with English translation).
Notice of Grant in KR App. Ser. No. 10-2007-7026886, dated Dec. 31, 2009, 5 pages (with English translation).
Notice of Non-Substantive Deficiencies Prior to Allowance in IL App. Ser. No. 197141, dated Feb. 3, 2013, 16 pages (with English translation).
Notice of Reasons for Rejection issued in JP App. Ser. No. P2009-540099, dated Jul. 2, 2013, 7 pages (with English translation).
Notice of Reasons for Rejection mailed on Nov. 13, 2012 issued for corresponding Japanese Application No. 2007-533350 with full English language translation.
Notice Prior to Allowance in IL App. Ser. No. 188670, dated Sep. 12, 2011, 2 pages (with English translation).
Notice Prior to Allowance in IL App. Ser. No. 197002, dated Oct. 28, 2012, 2 pages (with English translation).
Notice Prior to Examination dated Jun. 29, 2008 for IL App. Ser. No. 189677, 3 pages (with English translation).
Notice Prior to Examination dated Mar. 9, 2009 for IL App. Ser. No. 181697, 3 pages (with English translation).
Notice Prior to Examination in IL App. Ser. No. 188670, dated Aug. 13, 2009, 3 pages (with English translation).
Notice Prior to Examination in IL App. Ser. No. 197002, dated Mar. 23, 2010, 3 pages (with English translation).
Notice Prior to Examination in IL App. Ser. No. 197141, dated Mar. 23, 2010, 3 pages (with English translation).
Notice Prior to Examination in IL App. Ser. No. 200466, dated Jun. 22, 2010, 3 pages (with English translation).
Notice Requesting Submission of Opinion in KR Application No. 10-2006-7013993 mailed Jul. 31, 2007, 9 pages (with English translation).
Notification dated Apr. 25, 2008 for PH App. Ser. No. 1-2003-500266, 1 page.
Notification of Defects for IL App. Ser. No. 195282, dated Apr. 10, 2013, 4 pages (with English Translation).
Notification of Non-Compliant Amendment filed on Jan. 13, 2005 for U.S. Appl. No. 10/420,466.
Noy et al., "Tumor-Associated Macrophages From Mechanisms to Therapy," Immunity, Jul. 2014, 41:49-61.
Nugiel et al., "Synthesis and evaluation of indenopyrazoles as cyclin-dependent kinase inhibitors. 2. Probing the indeno ring substituent pattern," J. Med. Chem., 45(24):5224-5232 (2002).
Nyati et al., "Radiosensitization by Pan ErbB Inhibitor CI-1033 in Vitro and in Vivo", Clinical Cancer Research., 10:691-700, 2004.
Observation for CN App. Ser. No. 200880115011.7, dated Apr. 11, 2013, 10 pages (with English translation).
Observations for CN App. Ser. No. 201080030508.6, dated May 27, 2013, 7 pages (with English translation).
Ocqueteau et al., Expression of the CD117 antigen (C-Kit) on normal and myelomatous plasma cells, Br. J. Haematol., 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 27, 2010 for CN App. Ser. No. 200710007097.9, 7 pages (with English translation).
Office Action dated Apr. 28, 2009 for JP App. Ser. No. 2005-124034, 3 pages (with English translation).
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Aug. 11, 2006 for CN App. Ser. No. 01819710.8, 6 pages (with English translation).
Office Action dated Aug. 3, 2012 for CN App. Ser. No. 200680020317.5 (with English translation).
Office Action dated Aug. 8, 2003 for PH App. Ser. No. Jan. 2003-500266, 1 page.
Office Action dated Dec. 20, 2010 for IL App. Ser. No. 181697, 3 pages (with English translation).
Office Action dated Dec. 25, 2009 for CN App. Ser. No. 200710007097.9, 6 pages (with English translation).
Office Action dated Feb. 10, 2006 for CN App. Ser. No. 01819710.8, 8 pages (with English translation).
Office Action dated Jan. 27, 2009 for JP App. Ser. No. 2005-124034, 8 pages (with English translation).
Office Action dated Jul. 15, 2011 for CA App. Ser. No. 2579810, 2 pages.
Office Action dated Jul. 21, 2006 for PH App. Ser. No. 1-2003-500266, 1 pages.
Office Action dated Jul. 24, 2009 for CN App. Ser. No. 200710007096.4, 8 pages. (with English translation).
Office Action dated Jul. 27, 2005 for KR App. Ser. No. 10-2003-7005506, 4 pages (with English translation).
Office Action dated Jun. 26, 2009 for CN App. Ser. No. 200580026468.7, 25 pages (with English translation).
Office Action dated Jun. 27, 2007 for PH App. Ser. No. 1-2003-500266, 1 page.
Office Action dated Jun. 5, 2012 for JP App. Ser. No. 2009-123432, 4 pages (with English translation).
Office Action dated Jun. 7, 2006 for MX App. Ser. No. PA/a/2003/003362, 6 pages (with English translation).
Office Action dated Mar. 14, 2013 for CN App. Ser. No. 200780017371.9, 9 pages (with English translation).
Office Action dated Mar. 21, 2007 for PH App. Ser. No. 1-2003-500266, 1 page.
Office Action dated Mar. 29, 2013 for U.S. Appl. No. 13/624,278, 73 pages.
Office Action dated Mar. 6, 2009 for CN App. Ser. No. 200710007097.9 (with English translation).
Office Action dated Mar. 7, 2007 for NO App. Ser. No. 20031731, 3 pages (with English translation).
Office Action dated May 13, 2005 for CN App. Ser. No. 01819710.8, 8 pages (with English translation).
Office Action dated May 16, 2008 for NO App. Ser. No. 20031731, 2 pages (with English translation).
Office Action dated May 3, 2013 for CA App. Ser. No. 2661702, 2 pages.
Office Action dated Nov. 13, 2012 for JP App. Ser. No. P2008-532141, 8 pages (with English translation).
Office Action dated Nov. 20, 2009 for CN App. Ser. No. 200580026468.7, 9 pages (with English translation).
Office Action dated Nov. 26, 2007 for MX App. Ser. No. PA/a/2005/013764, 6 pages (with English translation).
Office Action dated Oct. 11, 2007 for TW App. Ser. No. 90125928, 5 pages (with English translation).
Office Action dated Oct. 15, 2012 for IL App. Ser. No. 200090, 5 pages (with English translation).

(56) References Cited

OTHER PUBLICATIONS

Office Action dated Oct. 15, 2012 for NZ App. Ser. No. 598291, 2 pages.
Office Action dated Oct. 4, 2005 for MX App. Ser. No. PA/a/2003/003362, 8 pages (with English translation).
Office Action dated Oct. 4, 2007 for NO App. Ser. No. 20031731, 2 pages (with English translation).
Office Action dated Sep. 11, 2009 for CN App. Ser. No. 200710007097.9, 8 pages (with English translation).
Office Action dated Sep. 19, 2012 for CA App. Ser. No. 2627598, 3 pages.
Office Action dated Sep. 28, 2011 for KR App. Ser. No. 10-2007-7001347, 12 pages (with English translation).
Office Action dated Sep. 28, 2012 for CN App. Ser. No. 200780017371.9, 9 pages (with English translation).
Office Action dated Sep. 29, 2012 for CN App. Ser. No. 200980103218.7, 13 pages (with English translation).
Office Action dated Sep. 5, 2008 for NO App. Ser. No. 20031731, 2 pages (with English translation).
Office Action dated Sep. 5, 2012 for CN App. Ser. No. 200880003336.6, 12 pages (with English translation).
Office Action dated Sep. 5, 2012 for CN App. Ser. No. 200880115011.7, 6 pages (with English translation).
Office Action dated Sep. 7, 2007 for PH App. Ser. No. 1-2003-500266, 1 page.
Office Action directed at Israel Application No. 207089 issued on Nov. 13, 2011, 4 pages (with English translation).
Office Action for Canadian Application No. 2,620,594, dated Aug. 15, 2011, 2 pages.
Office Action for EP App. Ser. No. 08846814.5, dated Apr. 16, 2013, 5 pages.
Office Action for IL 199907 issued on Jun. 17, 2010, 3 pages with English translation.
Office Action for IL App. Ser. No. 175363, dated Jan. 2, 2013, 2 pages, with English translation.
Office Action for IL App. Ser. No. 200090, dated Jul. 24, 2013, 5 pages (with English translation).
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for Indian Application No. 1908/DELNP/2008, dated Feb. 2, 2012, 2 pages.
Office Action for JP App. Ser. No. 2008-556208, dated Jan. 22, 2013, 8 pages, with English translation.
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for JP2007-542863 dated May 29, 2012, 8 pages with English translation.
Office Action for KR App. Ser. No. 10-2008-7013685, dated May 20, 2013, 10 pages (with English translation).
Office Action for PH App. Ser. No. 1-2011-502441 on Oct. 1, 2013, 1 page.
Office Action for U.S. Appl. No. 12/039,381, dated Sep. 12, 2013, 15 pages.
Office Action for U.S. Appl. No. 13/083,338, dated Jan. 3, 2013, 9 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action in AU App. Ser. No. 2006282456, dated Jun. 12, 2009, 1 pages.
Office Action in AU App. Ser. No. 2010285740, dated Aug. 22, 2014, 3 pages.
Office Action in BD App. Ser. No. 184/2006, dated May 11, 2007, 2 pages.
Office Action in BR App. Ser. No. PI0418200-6, dated Jun. 16, 2015, 1 page.
Office Action in CA App. Ser. No. 2543859, dated Aug. 19, 2008, 5 pages.
Office Action in CA App. Ser. No. 2543861, dated Aug. 19, 2008, 4 pages.
Office Action in CA App. Ser. No. 2605854, dated Jul. 29, 2009, 2 pages.
Office Action in CA App. Ser. No. 2652442, dated Oct. 4, 2013, 2 pages.
Office Action in CA App. Ser. No. 2676796, dated Dec. 30, 2013, 5 pages.
Office Action in CA App. Ser. No. 2676796, dated Jan. 29, 2015, 5 pages.
Office Action in CA App. Ser. No. 2704000, dated Jul. 14, 2015, 3 pages.
Office Action in CA App. Ser. No. 2704000, dated Mar. 27, 2015, 3 pages.
Office Action in CA App. Ser. No. 2704000, dated Nov. 4, 2014, 3 pages.
Office Action in CA App. Ser. No. 2713930, dated Jan. 30, 2015, 5 pages.
Office Action in CA App. Ser. No. 2713930, dated Sep. 15, 2015, 3 pages.
Office Action in CA App. Ser. No. 2771403, dated Jul. 16, 2014, 3 pages.
Office Action in Chinese Application No. 200710007097.9, mailed Mar. 6, 2009, 5 pages.
Office Action in CL App. Ser. No. 2012-00412, dated Jan. 28, 2015, 17 pages (with English translation).
Office Action in CL App. Ser. No. 2012-00412, dated Sep. 3, 2014, 22 pages (with English translation).
Office Action in CN App. Ser. No. 200680020317.5, dated Mar. 4, 2014, 13 pages.
Office Action in CN App. Ser. No. 200680020317.5, dated Nov. 28, 2013, 8 pages (with English translation).
Office Action in CN App. Ser. No. 200680021939.X, dated Mar. 30, 2011, 7 pages (with English translation).
Office Action in CN App. Ser. No. 200680021939.X, dated May 27, 2010, 9 pages (with English translation).
Office Action in CN App. Ser. No. 200680021939.X, dated Sep. 2, 2010, 10 pages (with English translation).
Office Action in CN App. Ser. No. 200780017371.9, dated Dec. 11, 2014, 9 pages (with English translation).
Office Action in CN App. Ser. No. 200780017371.9, dated May 15, 2015, 17 pages (with English translation).
Office Action in CN App. Ser. No. 200780019200.X, dated Apr. 6, 2012, 9 pages (with English translation).
Office Action in CN App. Ser. No. 200780019520.5, dated Dec. 21, 2010, 7 pages (with English translation).
Office Action in CN App. Ser. No. 200780019520.5, dated Sep. 27, 2010, 8 pages (with English translation).
Office Action in CN App. Ser. No. 2008800045113, dated Jul. 5, 2011, 10 pages (with English translation).
Office Action in CN App. Ser. No. 201180030568.2, dated Mar. 24, 2014, 8 pages (with English translation).
Office Action in CN App. Ser. No. 201180030568.2, dated Oct. 12, 2013, 11 pages (with English translation.
Office Action in CN App. Ser. No. 201280010427.9, dated Mar. 31, 2014, 11 pages (with English translation).
Office Action in CN App. Ser. No. 201280010898.X, dated Aug. 11, 2014, 14 pages (with English translation).
Office Action in CN App. Ser. No. 201280010898.X, dated Mar. 30, 2015, 13 pages (with English translation).
Office Action in CO App. Ser. No. 12-022608, dated Dec. 17, 2013, 12 pages (with English translation).
Office Action in DB App. Ser. No. 60/2005, dated Jul. 25, 2006, 2 pages.
Office Action in EP App. Ser. No. 03791389.4, dated Dec. 2, 2014, 5 pages.
Office Action in EP App. Ser. No. 03791389.4, dated Jun. 10, 2014, 4 pages.

(56) References Cited

OTHER PUBLICATIONS

Office Action in EP App. Ser. No. 04807580.8, dated Mar. 18, 2014, 12 pages.
Office Action in EP App. Ser. No. 05719973.9, dated Feb. 11, 2011, 7 pages.
Office Action in EP App. Ser. No. 05719973.9, dated Nov. 2, 2011, 4 pages.
Office Action in EP App. Ser. No. 07793075.8, dated Mar. 1, 2011, 3 pages.
Office Action in EP App. Ser. No. 08704376.6, dated Feb. 24, 2014, 4 pages.
Office Action in EP App. Ser. No. 08846814.5, dated Jun. 4, 2014, 4 pages.
Office Action in EP App. Ser. No. 10809938.3, dated Oct. 16, 2014, 5 pages.
Office Action in EP App. Ser. No. 12774278.1, dated Mar. 9, 2015, 6 pages.
Office Action in EP Application No. 07743994.1, dated Sep. 9, 2014, 8 pages.
Office Action in EP Application No. 10809938.3, dated Feb. 10, 2015, 4 pages.
Office Action in HU App. Ser. No. P0302603, dated Apr. 7, 2015, 5 pages (with English translation).
Office Action in ID App. Ser No. W-00 2008 00601, dated Jan. 13, 2012, 4 pages (with English translation).
Office Action in IL App. Ser. No. 188670, dated Jul. 3, 2011, 2 pages (with English translation).
Office Action in IL App. Ser. No. 197002, dated Feb. 8, 2012, 2 pages (with English translation).
Office Action in IL App. Ser. No. 197141, dated Feb. 22, 2012, 18 pages (with English translation).
Office Action in IL App. Ser. No. 205512, dated Oct. 28, 2013, 5 pages (with English translation).
Office Action in IL App. Ser. No. 205512, dated Sep. 22, 2014, 5 pages (with English translation).
Office Action in IL App. Ser. No. 207089, dated Nov. 25, 2013, 6 pages (with English translation).
Office Action in IL App. Ser. No. 217197, dated Oct. 22, 2014, 4 pages (with English translation).
Office Action in IL App. Ser. No. 223695, dated Aug. 25, 2015, 6 pages.
Office Action in IL App. Ser. No. 223695, dated Feb. 16, 2015, 5 pages (with English translation).
Office Action in IL App. Ser. No. 227558, dated Aug. 2, 2015, 5 pages (with English translation).
Office Action in IL App. Ser. No. 227777, dated Mar. 12, 2014, 5 pages (with English translation).
Office Action in IN App. Ser. No. 1424/CHENP/2008, dated Sep. 19, 2011, 18 pages.
Office Action in IN App. Ser. No. 1571/CHENP/2007, dated Oct. 23, 2013, 2 pages.
Office Action in IN App. Ser. No. 1571/CHENP/2007, Dec. 9, 2013, 2 pages.
Office Action in JP App. Ser. No. 2012-521531, dated Sep. 29, 2015, 4 pages (with English translation).
Office Action in JP App. Ser. No. 2008-530917, dated Oct. 23, 2012, 4 pages (with English translation).
Office Action in JP App. Ser. No. 2011-206481, dated Jun. 2, 2015, 7 pages (with English translation).
Office Action in JP App. Ser. No. 2013-510994, dated Jun. 9, 2015, 6 pages (with English translation).
Office Action in JP App. Ser. No. P2009-510543, dated Sep. 29, 2009, 7 pages (with English translation).
Office Action in JP App. Ser. No. P2009-540099, dated Mar. 25, 2014, 6 pages (with English translation).
Office Action in JP App. Ser. No. P2012-521531, dated Mar. 3, 2015, 6 pages (with English translation).
Office Action in JP Application No. P2005-516605 mailed Jun. 1, 2010, 3 pages.

Office Action in JP. App. Ser. No. 2013-510994, dated Jul. 28, 2015, 5 pages (with English translation).
Office Action in KR App. Ser. No. 10-2006-7013907, dated Jul. 28, 2007, 7 pages (with English translation).
Office Action in KR App. Ser. No. 10-2006-7013940, dated Jul. 31, 2007, 19 pages (with English translation).
Office Action in KR App. Ser. No. 10-2007-7026886, dated Aug. 27, 2009, 5 pages (with English translation).
Office Action in KR App. Ser. No. 10-2008-7027527, dated Dec. 9, 2013, 6 pages (with English translation).
Office Action in KR App. Ser. No. 10-2008-7029472, dated Mar. 28, 2014, 6 pages (with English translation).
Office Action in KR App. Ser. No. 10-2008-7029577, dated Dec. 30, 2013, 7 pages (with English translation).
Office Action in KR App. Ser. No. Oct. 2009-7005657, dated Mar. 28, 2014, 6 pages (with English translation).
Office Action in KR App. Ser. No. 10-2009-7013723, dated May 19, 2011, 10 pages (with English translation).
Office Action in KR App. Ser. No. 10-2009-7017694, dated Jan. 29, 2014, 26 pages (with English translation).
Office Action in KR App. Ser. No. 10-2010-7011023, dated Sep. 3, 2014, 14 pages (with English translation).
Office Action in KR App. Ser. No. 10-2010-7018835, dated Sep. 30, 2014, 6 pages (with English translation).
Office Action in KR App. Ser. No. 10-2012-7003846, dated Oct. 7, 2014, 7 pages.
Office Action in MX App. Ser. No. MX/a/2010/008187, dated Apr. 28, 2014, 4 pages (with English translation).
Office Action in MX App. Ser. No. MX/a/2010/008187, dated Dec. 5, 2013, 8 pages (with English translation).
Office Action in MX App. Ser. No. MX/a/2012/002011, dated Apr. 28, 2014, 10 pages (with English translation).
Office Action in MX App. Ser. No. MX/a/2012/002011, dated Nov. 21, 2013, 8 pages (with English translation).
Office Action in MX App. Ser. No. MX/a/2012/014776, dated Apr. 4, 2014, 22 pages (with English Translation).
Office Action in MX App. Ser. No. MX/a/2012/014776, dated Oct. 15, 2014, 15 pages (with English translation).
Office Action in MX App. Ser. No. MX/a/2013/009931, dated Apr. 9, 2015, 3 pages (with English translation).
Office Action in MX App. Ser. No. MX/a/2013/009931, dated Sep. 5, 2014, 15 pages (with English translation).
Office Action in NO App. Ser. No. 20063383, dated Apr. 15, 2015, 2 pages (with English translation).
Office Action in NZ App. Ser. No. 566793, dated Dec. 4, 2009, 1 page.
Office Action in PH App. Ser. No. 1-2007-502319, dated Dec. 16, 2011, 1 page.
Office Action in PH App. Ser. No. 1-2011-502441, dated Feb. 19, 2014, 2 pages.
Office Action in PH App. Ser. No. 1-2011-502441, dated May 8, 2015, 2 pages.
Office Action in PK App. Ser. No. 1024/2006, dated Dec. 12, 2007, 3 pages.
Office Action in PK App. Ser. No. 1024/2006, dated Feb. 24, 2009, 2 pages.
Office Action in PK App. Ser. No. 1024/2006, dated Oct. 21, 2008, 2 pages.
Office Action in PK App. Ser. No. 155/2005, dated Nov. 17, 2007, 2 pages.
Office Action in PK App. Ser. No. 375/2008, dated Feb. 24, 2009, 1 page.
Office Action in PK App. Ser. No. 375/2008, dated Jul. 20, 2009, 2 pages.
Office Action in PK App. Ser. No. 375/2008, dated Oct. 21, 2008, 3 pages.
Office Action in RU App. Ser. No. 2006134254, dated Oct. 13, 2006, 4 pages (with English translation).
Office Action in RU App. Ser. No. 2006134254, dated Sep. 18, 2007, 9 pages (with English translation).
Office Action in RU App. Ser. No. 2008110932, dated Dec. 3, 2008, 6 pages (with English translation).

(56) References Cited

OTHER PUBLICATIONS

Office Action in RU App. Ser. No. 2012103471, dated May 20, 2014, 5 pages (with English translation).
Office Action in RU App. Ser. No. 2012103471, dated Sep. 16, 2014, 5 pages (with English translation).
Office Action in RU App. Ser. No. 2012158142, dated Feb. 12, 2015, 21 pages (with English translation).
Office Action in RU App. Ser. No. 2013139556, dated Dec. 2, 2013, 6 pages (with English translation).
Office Action in TW App. Ser. No. 095130665, dated Mar. 2, 2012, 8 pages (with English translation).
Office Action in TW App. Ser. No. 100104281, dated Dec. 9, 2014, 13 pages (with English translation).
Office Action in U.S. Appl. No. 12/039,381, dated Oct. 7, 2015, 22 pages.
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 11/662,425, dated Feb. 27, 2014, 152 pages.
Office Action in U.S. Appl. No. 11/662,425, dated Jun. 5, 2014, 30 pages.
Office Action in U.S. Appl. No. 11/662,425, dated Sep. 17, 2014, 3 pages.
Office Action in U.S. Appl. No. 11/997,543, dated Mar. 11, 2014, 20 pages.
Office Action in U.S. Appl. No. 12/031,568, dated Aug. 13, 2010, 15 pages.
Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/039,381, dated Feb. 26, 2015, 13 pages.
Office Action in U.S. Appl. No. 12/039,381, dated Jan. 9, 2014, 16 pages.
Office Action in U.S. Appl. No. 12/039,381, dated May 29, 2014, 78 pages.
Office Action in U.S. Appl. No. 12/315,291, dated Jan. 12, 2011, 9 pages.
Office Action in U.S. Appl. No. 12/315,291, dated Jun. 7, 2010, 20 pages.
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/864,817, dated Aug. 15, 2014, 79 pages.
Office Action in U.S. Appl. No. 12/867,646, dated Oct. 26, 2011, 37 pages.
Office Action in U.S. Appl. No. 13/238,085, dated Nov. 12, 2013, 74 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/805,826, dated Sep. 23, 2014, 25 pages.
Office Action in U.S. Appl. No. 13/870,507, dated Apr. 1, 2015, 82 pages.
Office Action in U.S. Appl. No. 13/870,507, dated Dec. 12, 2014, 10 pages.
Office Action in U.S. Appl. No. 13/923,858, dated Apr. 18, 2014, 64 pages.
Office Action in U.S. Appl. No. 13/923,858, dated Dec. 5, 2014, 67 pages.
Office Action in U.S. Appl. No. 13/923,858, dated Jul. 29, 2015, 15 pages.
Office Action in U.S. Appl. No. 13/983,891, dated Jan. 22, 2014, 11 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Office Action in U.S. Appl. No. 11/065,631, dated Feb. 28, 2008, 12 pages.
Office Action in VN App. Ser. No. 1-2008-00723, dated Mar. 11, 2010, 4 pages (with English translation).
Office Action in VN App. Ser. No. 1-2011-03484, dated Dec. 31, 2013, 2 pages (with English translation).
Office Action issued for CN 200880002425.9 on Mar. 2, 2011, 10 pages with English translation.
Office Action issued for EP 06768437.3 (EPO Form1224) issued on Oct. 28, 2010, 47 pages.
Office Action issued for European Search Report for European Application No. 06782407 on Sep. 29, 2011, 6 pages.
Office Action issued for Japanese Application No. 2007-529565 issued on Dec. 13, 2011, 7 pages with English full translation.
Office Action issued for JP Appl. No. 2007-529565 issued on May 8, 2012, 6 pages with English translation.
Office Action issued in MX App. Ser. No. MX/a/2012/002011, dated Jul. 17, 2013, 6 pages (with English translation).
Office Action issued Jan. 7, 2011, in U.S. Appl. No. 12/092,539, 12 pages.
Office Action, U.S. Appl. No. 11/347,749 mailed Feb. 9, 2009, 6 pages.
Office Communication dated Sep. 13, 2004 for U.S. Appl. No. 10/420,466, 7 pages.
Office Letter Confirmation of Amendment After Allowance dated Jan. 11, 2011 for CA App. Ser. No. 2426461, 1 pages.
Office Letter re Notice of Allowance dated May 25, 2012 for ZA App. Ser. No. 201108697, 3 pages.
Official Letter and Notice of Allowance for AU App. Ser. No. 2008211952, dated Jul. 10, 2012, 10 pages.
Official Letter and Notice of Allowance for AU App. Ser. No. 2008325608, dated Feb. 27, 2013, 7 pages.
Official Letter dated Jun. 27, 2013 in CA App. Ser. No. 2661333, 2 pages.
Official Letter in AU App. Ser. No. 2006282456, dated May 15, 2012, 1 page.
Official Letter in AU App. Ser. No. 2006282456, dated Sep. 24, 2012, 259 pages.
Official Letter in BD App. Ser. No. 184/2006, dated Feb. 2, 2012, 1 page.
Official Letter re Deficiencies in sequence listing in EP App. Ser. No. 06796594.7, dated Mar. 10, 2008, 3 pages.
Official Letter re Grant of Request for Correction of Specification for SG App. Ser. No. 201108602-2, dated Aug. 8, 2012, 2 pages.
Official Letter re Granting Patent in EP App. Ser. No. 06796594.7, dated Sep. 25, 2012, 270 pages.
Official Letter re Intention to Grant Patent in EP App. Ser. No. 05719973.9, dated Feb. 6, 2012, 553 pages.
Official Letter re invitation to declare maintenance in EP App. Ser. No. 06796594.7, dated Sep. 26, 2011, 1 page.
Official Letter re invitation to declare maintenance in EP App. Ser. No. 07793075.8, dated Sep. 27, 2010, 1 page.
Official Letter re invitation to declare maintenance in EP App. Ser. No. 07805959.9, dated Dec. 3, 2010, 1 page.
Official Letter re invitation to declare maintenance in EP App. Ser. No. 08711837.8, dated Apr. 14, 2011, 1 page.
Official Letter re invitation to declare maintenance in EP App. Ser. No. 09713617.0, dated May 17, 2011, 5 pages.
Official Notification in CA App. Ser. No. 2771403, dated Dec. 16, 2014, 1 page.
Official Notification in CO App. Ser. No. 12-022608, dated Jan. 6, 2015, 8 pages (with English translation).
Official Notification in EP App. Ser. No. 04807580.8, dated Jun. 16, 2014, 1 pages.

(56) References Cited

OTHER PUBLICATIONS

Official Notification in EP App. Ser. No. 04807580.8, dated Jun. 27, 2014, 17 pages.
Official Notification re Decision on Petition in U.S. Appl. No. 11/997,719, dated Sep. 23, 2014, 1 page.
Official Notification re Interview Summary in U.S. Appl. No. 13/805,826, dated Dec. 1, 2014, 3 pages.
Official Notification re Interview Summary in U.S. Appl. No. 14/002,018, dated Oct. 6, 2014, 2 pages.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," Ann Oncol., 18(2):317-323 (2007).
Okayama et al., "Activation of Eosinophils with Cytokines Produced by Lung Mast Cells," Int Arch Allergy Immunol., 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," Eur. J. Immunol., 28:708-715 (1998).
Okura et al., "Effects of monoclonal anti-c-kit antibody (ACK2) on melanocytes in newborn mice," J. Invest. Dermatol., 105(3):322-328 (1995).
Olaso et al., "DDR2 receptor promotes MMP-2-mediated proliferation and invasion by hepatic stellate cells," J. Clin. Invest., 108(9):1369-1378 (2001).
O'Reilly et al., "Hydrolysis of tert-Butyl Methyl Ether (MTBE) in Dilute Aqueous Acid," Environ. Sci. Technol., 2001, 35:3954-3961.
Ozols et al., "Phase III trial of carboplatin and paclitaxel compared with cisplatin and paclitaxel in patients with optimally resected stage III ovarian cancer: a Gynecologic Oncology Group study," J. Clin. Oncol., 21(17):3194-3200 (2003).
Pacini, "38th Annual Meeting of the European Thyroid Association", European Thyroid Association, Santiago de Compostela, Spain, Aug. 15, 2014, pp. 73-226.
Pakistani Office Action for App. Ser. No. 94/2011, issued on May 9, 2012, 2 pages.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Park, "Serum Angiopoietin-2 as a Clinical Market for Lung Cancer," Chest, Jul. 2007, 132(1):200.
Partial European Search Report for App. Ser. No. 01976786.2, dated Apr. 6, 2004, 5 pages.
Patel et al., "The effect of excipients on the stability of levothyroxine sodium pentahydrate tablets," Int'l J Pharm., 2003, 264:35-43.
Paterson et al., "Preclinical studies of fibroblast growth factor receptor 3 as a therapeutic target in multiple myeloma," British Journal of Haematology, 124:595-603 (2004).
Paulus, "Preparation and Biomedical Applications of Bispecific Antibodies", Behring Inst. Mitt. 78: 118-132 (1985).
Payment of Final Fee and Amendment after Allowance in CA App. Ser. No. 2771403, dated Nov. 24, 2014, 3 pages.
Paz et al., "Development of angiogenesis inhibitors to vascular endothelial growth factor receptor 2. Current status and future perspective," Frontiers in Bioscience, 10:1415-1439 (May 1, 2005).
Pearson, "Rapid and Sensitive Sequence Comparison with FASTP and FASTA", Methods in Enzymology 183 :63-98 (1990).
Petition in JP App. Ser. No. 2007-532099, dated Dec. 25, 2007, 3 pages (with English translation).
Petition in JP App. Ser. No. 2007-532099, dated Sep. 25, 2007, 3 pages (with English translation).
Petition in JP App. Ser. No. 2009-554285, dated Aug. 19, 2010, 3 pages (with English translation).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood., 103, 3474-3479, 2004.
Polverino et al, "AMG 706, an Oral, Multikinase Inhibitor that Selectively Targets Vascular Endothelial Growth Factor, Platelet—Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed on Aug. 10, 2011, 24 pages.
Preliminary Amendment and Response to Restriction Requirement in U.S. Appl. No. 13/083,338, filed on Apr. 30, 2012, 16 pages.
Preliminary Amendment dated Apr. 26, 2013 for U.S. Appl. No. 13/870,507, 10 pages.
Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Aug. 27, 2015, 7 pages.
Preliminary Amendment filed in U.S. Appl. No. 14/122,339, dated Nov. 26, 2013, 10 pages.
Preliminary Amendment filed on Apr. 18, 2003 for U.S. Appl. No. 10/420,466, 376 pages.
Preliminary Amendment filed on Dec. 2, 2005 for U.S. Appl. No. 10/420466, 36 pages.
Preliminary Amendment filed on Feb. 3, 2006 for U.S. Appl. No. 11/293,785, 33 pages.
Preliminary Amendment filed on May 23, 2003 for KR App. Ser. No. 10-2003-7005506, 42 pages (with English translation).
Preliminary Amendment filed on Oct. 27, 2003 for U.S. Appl. No. 10/420,517, 41 pages.
Preliminary Amendment for U.S. Appl. No. 13/624,278, filed Sep. 21, 2012, 7 pages.
Preliminary Amendment in U.S. Appl. No. 10/577,043, dated Apr. 24, 2006, 12 pages.
Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.
Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.
Pritzker, "Cancer Biomarkers: Easier Said Than Done," Clinical Chemistry, 48(8):1147-1150 (2002).
Reasons for Reexamination dated Sep. 11, 2012 for CN App. Ser. No. 200680020317.5, 7 pages (with English translation).
Reexamination filed on May 25, 2004 for TW App. Ser. No. 90125928, 59 pages (with English translation).
Reexamination filed on Nov. 25, 2004 for TW App. Ser. No. 90125928, 59 pages (with English translation).
Registered dated Feb. 24, 2009 for PH App. Ser. No. 1-2003-500266, 3 pages.
Registry's Letter in MT App. Ser. No. 3723, dated Sep. 29, 2007, 1 page.
Rejection dated Apr. 26, 2004 for TW App. Ser. No. 90125928, 10 pages (with English translation).

(56) References Cited

OTHER PUBLICATIONS

Ren, Xiubao, "Advances in Medical Therapy for Melanoma," Journal of Practical Oncology, Dec. 2010, 2(25):137-140 (with English translation).
Reply to communication from the Examining Division for EP App. Ser. 06023078.6, dated Feb. 4, 2008, 97 pages.
Reply to communication from the Examining Division for EP App. Ser. 06023078.6, dated Sep. 11, 2007, 10 pages.
Reply to communication from the Examining Division for EP App. Ser. No. 01976786.2, dated Jan. 25, 2006, 36 pages.
Reply to communication from the Examining Division for EP App. Ser. No. 01976786.2, dated Jul. 19, 2006, 124 pages.
Reply to communication from the Examining Division for EP App. Ser. No. 04025700.8, dated Feb. 15, 2007, 2 pages.
Reply to communication from the Examining Division for EP App. Ser. No. 04025700.8, dated Jan. 26, 2007, 232 pages.
Reply to communication from the Examining Division for EP App. Ser. No. 04025700.8, dated Sep. 12, 2006, 21 pages.
Reply to Examination Report dated Feb. 8, 2013 for EP App. Ser. No. 07743994.1, 4 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Notice of Allowance in U.S. Appl. No. 11/662,425, dated Jan. 20, 2015, 5 pages.
Reply to Notice of Non-Compliant Amendment in U.S. Appl. No. 12/315,291, dated Nov. 12, 2010, 3 pages.
Reply to official communication for EP App. Ser. No. 05783232.1, dated Apr. 30, 2008, 13 pages.
Reply to Restriction Requirement in U.S. Appl. No. 13/870,507, dated Jan. 27, 2015, 3 pages.
Reply to the invitation to remedy deficiencies for EP App. Ser. No. 06023078.6, dated Jan. 11, 2007, 3 pages.
Request for accelerated examination in KR App. Ser. No. 10-2012-7003846, dated Jun. 18, 2014, 29 pages (with English translation).
Request for amendment of the text intended for grant and translation of claims for EP App. Ser. No. 04025700.8, dated Feb. 1, 2008, 41 pages.
Request for amendment of the text intended for grant and translation of claims for EP App. Ser. No. 06023078.6, dated Nov. 5, 2008, 19 pages.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Request for Continued Examination (RCE) transmittal for U.S. Appl. No. 12/864,817, filed on Dec. 22, 2011, 1 page.
Request for correction of errors in filed documents for EP App. Ser. No. 06023078.6, dated Feb. 13, 2007, 4 pages.
Request for Examination filed in KR App. Ser. No. 10-2012-7033886, dated Aug. 26, 2015, 12 pages (with English translation).
Request for Examination filed in NO App. Ser. No. 20063383, dated Jun. 19, 2015, 8 pages (with English translation).
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 14 pages (with English translation).
Request for Voluntary Amendments filed May 10, 2012, in Ukraine Patent Application No. a 2012 03132, 11 pages with English Abstract.
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response and Amendment for CA App. Ser. No. 2652442, dated Sep. 5, 2013, 17 pages.
Response filed in CA App. Ser. No. 2652442, dated Jan. 8, 2014, 5 pages.
Response filed in CA App. Ser. No. 2713930, dated Jun. 22, 2015, 8 pages.
Response filed in CN App. Ser. No. 201280010898.X, dated Jun. 15, 2015, 12 pages (with English translation).
Response filed in CO App. Ser. No. 12-022608, dated Nov. 13, 2013, 13 pages (with English translation).
Response filed in IL App. Ser. No. 195282, filed Jul. 11, 2013, 13 pages (with English translation).
Response filed in IN App. Ser. No. 1571/CHENP/2007, dated Oct. 30, 2013, 9 pages.
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Feb. 28, 2014, 4 pages.
Response filed in PH App. Ser. No. 1-2011-502441, dated May 22, 2015, 25 pages.
Response filed in PH App. Ser. No. 1-2011-502441, dated Nov. 4, 2013, 28 pages.
Response filed in U.S. Appl. No. 13/870,507, dated Jun. 18, 2015, 13 pages.
Response filed in VN App. Ser. No. 1-2011-03484, dated Feb. 28, 2014, 40 pages (with English translation).
Response filed on Apr. 11, 2006 for CN App. Ser. No. 01819710.8, 4 pages (with English translation).
Response filed on Apr. 17, 2007 for PH App. Ser. No. 1-2003-500266, 1 page.
Response filed on Apr. 27, 2006 for AU App. Ser. No. 2001295986, 22 pages.
Response filed on Apr. 30, 2008 for PH App. Ser. No. 1-2003-500266, 1 page.
Response filed on Aug. 13, 2009 for CA App. Ser. No. 2426461, 4 pages.
Response filed on Aug. 14, 2006 for PH App. Ser. No. 1-2003-500266, 1 page.
Response filed on Aug. 18, 2008 for NO App. Ser. No. 20031731, 2 pages (with English translation).
Response filed on Aug. 21, 2006 for MX App. Ser. No. PA/a/2003/003362, 5 pages (with English translation).
Response filed on Aug. 26, 2004 for NZ App. Ser. No. 525324, 3 pages.
Response filed on Aug. 5, 2003 for PH App. Ser. No. 1-2003-500266, 1 page.
Response filed on Dec. 11, 2007 for TW App. Ser. No. 90125928, 54 pages (with English translation).
Response filed on Dec. 15, 2005 for MX App. Ser. No. PA/a/2003/003362, 9 page (with English translation).
Response filed on Dec. 4, 2007 for IL App. Ser. No. 155447, 35 pages (with English translation).
Response filed on Feb. 23, 2009 for CA App. Ser. No. 2426461, 31 pages.
Response filed on Feb. 26, 2008 for U.S. Appl. No. 11/293,785, 16 pages.
Response filed on Jan. 11, 2010 for CN App. Ser. No. 200580026468.7, 4 pages (with English translation).
Response filed on Jan. 21, 2005 for NZ App. Ser. No. 525324, 2 pages.
Response filed on Jan. 26, 2010 for CN App. Ser. No. 200710007097.9, 3 pages (with English translation).
Response filed on Jan. 26, 2011 for IL App. Ser. No. 181697, 5 pages (with English translation).
Response filed on Jul. 1, 2005 for U.S. Appl. No. 10/420,466, 14 pages.

(56) References Cited

OTHER PUBLICATIONS

Response filed on Jul. 2, 2009 for CN App. Ser. No. 200710007097.9, 4 pages (with English translation).
Response filed on Jul. 26, 2006 for AU App. Ser. No. 2001295986, 11 pages.
Response filed on Jul. 31, 2007 for PH App. Ser. No. 1-2003-500266, 1 page.
Response filed on Jun. 22, 2010 for CN App. Ser. No. 200710007097.9, 3 pages (with English translation).
Response filed on Mar. 17, 2005 for RU App. Ser. No. 2003114740, 75 pages (with English translation).
Response filed on May 13, 2009 for IL App. Ser. No. 189677, 125 pages (with English translation).
Response filed on May 16, 2008 for CA App. Ser. No. 2426461, 79 pages.
Response filed on May 20, 2010 for CA App. Ser. No. 2426461, 23 pages.
Response filed on May 7, 2008 for NO App. Ser. No. 20031731, 2 pages (with English translation).
Response filed on May 8, 2008 for AU App. Ser. No. 2006236039, 2 pages.
Response filed on Nov. 19, 2009 for CN App. Ser. No. 200710007097.9, 9 pages (with English translation).
Response filed on Nov. 30, 2004 for RU App. Ser. No. 2003114740, 90 pages (with English translation).
Response filed on Oct. 13, 2008 for NO App. Ser. No. 20031731, 400 pages (with English translation).
Response filed on Oct. 15, 2007 for PH App. Ser. No. 1-2003-500266, 1 page.
Response filed on Oct. 8, 2004 for U.S. Appl. No. 10/420,466, 19 pages.
Response filed on Oct. 9, 2006 for CN App. Ser. No. 01819710.8, 2 pages (with English translation).
Response filed on Sep. 10, 2007 for NO App. Ser. No. 20031731, 60 pages (with English translation).
Response filed on Sep. 13, 2005 for CN App. Ser. No. 01819710.8, 7 pages (with English translation).
Response filed on Sep. 15, 2003 for PH App. Ser. No. 1-2003-500266, 1 page.
Response filed on Sep. 21, 2011 for CA App. Ser. No. 2579810, 16 pages.
Response filed on Sep. 23, 2009 for CN Patent Application No. 200580026468.7, 4 pages with English translation.
Response filed on Sep. 8, 2003 for PH App. Ser. No. 1-2003-500266, 1 page.
Response in EP App. Ser. No. 06796594.7, dated Mar. 31, 2008, 3 pages.
Response in EP App. Ser. No. 12774278.1, dated Oct. 13, 2014, 4 pages.
Response in Reexamination and Invalidation Procedure in CN App. Ser. No. 200780017371.9, dated Jan. 19, 2015, 8 pages (with English translation).
Response to Advisory Action in U.S. Appl. No. 12/315,291, dated Mar. 31, 2011, 6 pages.
Response to AU OA for AU 2008211952 filed on Jun. 28, 2012, 36 pages.
Response to Australian Office Action filed on Apr. 29, 2010 for corresponding AU Application No. 2006285673, 11 pages.
Response to Australian Office Action filed on Jul. 28, 2010 for corresponding AU Application No. 2006285673, 6 pages.
Response to Australian Office Action filed on Oct. 16, 2009 for corresponding AU Application No. 2006285673, 14 pages.
Response to Canadian Office Action filed Feb. 13, 2012, in Canadian Application No. 2,620,594, 8 pages.
Response to Canadian Office Action filed on Apr. 12, 2011 for corresponding CA Application No. 2,620,594, 4 pages.
Response to Canadian Office Action filed on Apr. 26, 2011 for corresponding CA Application No. 2,620,594.
Response to Canadian Office Action filed on Jun. 21, 2010 for corresponding CA Application No. 2,620,594, 18 pages.
Response to Chinese Office Action filed on Jul. 11, 2012 for Chinese Patent Application No. 200680036592.6, 17 pages with English translation.
Response to Chinese Office Action filed on Mar. 5, 2010 for corresponding CN Application No. 200680036592.6, 11 pages (with English translation).
Response to Chinese Office Action for CN 200680020317.5 dated Sep. 11, 2012, 7 pages with English translation.
Response to CN OA for CN200880003336.6 filed on May 3, 2012, 15 pages.
Response to Communication in EP App. Ser. 07743994.1, dated Dec. 22, 2014, 62 pages.
Response to EESR in EP App. Ser. No. 09713617.0, dated Sep. 2, 2011, 12 pages.
Response to EP OA for EP 07806561.2 filed on Apr. 18, 2012, 8 pages.
Response to Examination Report in AU App. Ser. No. 2005217325, dated Oct. 26, 2007, 33 pages.
Response to Examination Report in AU App. Ser. No. 2005217328, dated Sep. 20, 2007, 6 pages.
Response to Examination Report in AU App. Ser. No. 2007288793, dated Mar. 30, 2012, 5 pages.
Response to Examiner's Report in CL App. Ser. No. 2012-00412, dated Mar. 30, 2015, 16 pages (with English translation).
Response to Examiner's Substantive Report in CL App. Ser. No. 2012-00412, dated Nov. 28, 2014, 39 pages (with English translation).
Response to Extended European Search Report in EP App. Ser. No. 07793075.8, dated Nov. 8 2010, 11 pages.
Response to Extended European Search Report in EP App. Ser. No. 07805959.9, dated Mar. 29, 2011, 2 pages.
Response to Hearing Notice in IN App. Ser. No. 1424/CHENP/2008, dated Sep. 11, 2012, 14 pages.
Response to IL OA for IL 195282 filed on May 28, 2012, 5 pages.
Response to Indian Office Action issued Feb. 2, 2012, dated Jun. 22, 2012, for Application No. 1908/DELNP/2008, 27 pages.
Response to Israeli Office Action filed on Sep. 7, 2010 for the corresponding Israeli Application No. 189589, 9 pages.
Response to Israeli Office Action, filed Jul. 24, 2012 for corresponding Israeli Patent Application No. 189589, 7 pages.
Response to Japanese Office Action dated Jul. 17, 2012 for Japanese Application No. 2007-533350, 12 pages with English translation.
Response to Japanese Office Action filed on Jan. 9, 2013 for corresponding Japanese Application JP-2007-533350, 6 pages.
Response to Korean Office Action filed on Feb. 24, 2010 for corresponding KR Application No. 10-2008-7005195, 31 pages with English translation.
Response to Korean Office Action filed on Jul. 29, 2010 for corresponding KR Application No. 10-2008-7005195, 26 pages with English translation.
Response to Notice of Allowability filed on Dec. 13, 2007 for PH App. Ser. No. 1-2003-500266, 1 page.
Response to Notice of Allowance in U.S. Appl. No. 13/205,328, dated Jul. 8, 2014, 7 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination filed in IL App. Ser. No. 217197, filed Jul. 31, 2013, 9 pages (with English translation).
Response to Notice Prior to Examination filed on Apr. 22, 2009 for IL App. Ser. No. 181697, 11 pages (with English translation).
Response to Notice Prior to Examination filed on Jan. 11, 2009 for IL App. Ser. No. 189677, 7 pages (with English translation).
Response to Notice Prior to Examination in IL App. Ser. No. 188670, dated Nov. 22, 2009, 29 pages (with English translation).
Response to Notice Prior to Examination in IL App. Ser. No. 197002, dated Oct. 13, 2010, 18 pages (with English translation).
Response to Notice Prior to Examination in IL App. Ser. No. 197141, dated Jun. 1, 2010, 22 pages (with English translation).
Response to OA for EP 10015141 filed on Mar. 5, 2012, 47 pages.
Response to Office Action dated Feb. 7, 2013 for CN App. Ser. No. 201080030508.6, 17 pages (with English translation).

(56) References Cited

OTHER PUBLICATIONS

Response to Office Action dated Jul. 5, 2012 for CN App. Ser. No. 200880115011.7, 24 pages (with English translation).
Response to Office Action dated Nov. 30, 2012 for CN App. Ser. No. 200780017371.9, 4 pages (with English translation).
Response to Office Action directed at Australian Appl. No. 2006309551 filed on Mar. 28, 2012, 27 pages.
Response to Office Action filed in EP App. Ser. No. 04807580.8, dated May 16, 2014, 13 pages.
Response to Office Action filed on Jan. 25, 2013 for CA App. Ser. No. 2627598, 9 pages.
Response to Office Action filed on Jul. 11, 2012 for CN App. Ser. No. 200880003336.6 (with English translation), 10 pages.
Response to Office Action filed on May 29, 2012 for RU App. Ser. No. 2012103471 (with English translation), 7 pages.
Response to Office Action for Australian App. Ser. No. 2006309551, filed on Mar. 28, 2012.
Response to Office Action for CA App. Ser. No. 2661702, filed Jul. 16, 2013, 13 pages.
Response to Office Action for EP 08704376.6 dated Jan. 2, 2013, 22 pages.
Response to Office Action for IL 199907 filed on Oct. 11, 2010, 4 pages (with English translation).
Response to Office Action for Israeli App. Ser. No. 205512, filed on Mar. 11, 2012 (with English translation), 12 pages.
Response to Office Action for Israeli App. Ser. No. 207089, filed on Mar. 11, 2012, with English translation, 13 pages.
Response to Office Action for MX App. Ser. No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005, 14 pages.
Response to Office Action in AU App. Ser. No. 2006282456, dated Jul. 16, 2009, 2 pages.
Response to office action in AU App. Ser. No. 2007289787, dated Feb. 16, 2012, 27 pages.
Response to office action in AU App. Ser. No. 2010285740, dated Oct. 28, 2014, 14 pages.
Response to Office Action in BD App. Ser. No. 184/2006, dated Dec. 13, 2007, 2 pages.
Response to Office Action in CA App. Ser. No. 2605854, dated Oct. 8, 2009, 18 pages.
Response to Office Action in CA App. Ser. No. 2661333, dated Nov. 12, 2013, 18 pages.
Response to Office Action in CA App. Ser. No. 2676796, dated Jun. 27, 2014, 18 pages.
Response to Office Action in CA App. Ser. No. 2704000, dated Dec. 19, 2014, 13 pages.
Response to Office Action in CA App. Ser. No. 2771403, dated Sep. 10, 2014, 11 pages.
Response to Office Action in CN App. Ser. No. 200680020317.5 filed on Jan. 9, 2014, 7 pages (with English translation).
Response to Office Action in CN App. Ser. No. 200680021939.X, dated Jul. 27, 2010, 44 pages (with English translation).
Response to Office Action in CN App. Ser. No. 200680021939.X, dated May 20, 2011, 39 pages (with English translation).
Response to Office Action in CN App. Ser. No. 200680021939.X, dated Oct. 28, 2010, 40 pages (with English translation).
Response to office action in CN App. Ser. No. 200780019200.X, dated Jul. 24, 2012, 49 pages (with English translation).
Response to office action in CN App. Ser. No. 200780019520.5, dated Dec. 3, 2010, 28 pages (with English translation).
Response to office action in CN App. Ser. No. 200780019520.5, dated Feb. 21, 2011, 7 pages (with English translation).
Response to Office Action in CN App. Ser. No. 201180030568.2 filed on Jan. 13, 2014, 46 pages (with English translation).
Response to Office Action in CN App. Ser. No. 201180030568.2 filed on May 14, 2014, 10 pages (with English translation).
Response to Office Action in CN App. Ser. No. 201280010427.9, dated Jun. 12, 2014, 13 pages (with English translation).
Response to office action in CN App. Ser. No. 201280010898.X, dated Nov. 25, 2014, 7 pages (with English translation).
Response to Office Action in EP App. Ser. No. 03791389.4, dated Jul. 25, 2014, 75 pages.
Response to office action in EP App. Ser. No. 05719973.9, dated Dec. 21, 2011, 150 pages.
Response to office action in EP App. Ser. No. 05719973.9, dated May 24, 2011, 26 pages.
Response to office action in EP App. Ser. No. 07793075.8, dated May 27, 2011, 17 pages.
Response to Office Action in EP App. Ser. No. 08704376.6, dated Apr. 30, 2014, 73 pages.
Response to Office Action in EP App. Ser. No. 08846814.5, dated Jul. 24, 2014, 71 pages.
Response to Office Action in EP App. Ser. No. 10809938.3, dated Apr. 13, 2015, 12 pages.
Response to office action in EP App. Ser. No. 12786619.2, dated May 12, 2015, 99 pages.
Response to office action in ID App. Ser No. W-00 2008 00601, dated Jun. 18, 2012, 3 pages (with English translation).
Response to office action in IL App. Ser. No. 188670, dated Aug. 15, 2011, 43 pages (with English translation).
Response to office action in IL App. Ser. No. 197002, dated Feb. 29, 2012, 7 pages (with English translation).
Response to office action in IL App. Ser. No. 197141, dated Jun. 6, 2012, 10 pages (with English translation).
Response to office action in IL App. Ser. No. 217197, dated Nov. 26, 2014, 7 pages (with English translation).
Response to office action in IN App. Ser. No. 1424/CHENP/2008, dated Jan. 18, 2012, 17 pages.
Response to office action in JP App. Ser. No. 2008-530917, dated Dec. 13, 2012, 9 pages (with English translation).
Response to office action in JP App. Ser. No. P2009-510543, dated Nov. 9, 2009, 12 pages (with English translation).
Response to office action in JP App. Ser. No. P2009-540099, dated Apr. 28, 2014, 9 pages (with English Translation).
Response to office action in KR App. Ser. No. 10-2006-7013907, dated Sep. 28, 2007, 10 pages (with English translation).
Response to office action in KR App. Ser. No. 10-2006-7013940, dated Oct. 1, 2007, 20 pages (with English translation).
Response to Office Action in MX App. Ser. No. MX/a/2010/008187, dated Feb. 17, 2014, 7 pages (with English translation).
Response to Office Action in MX App. Ser. No. MX/a/2010/008187, dated Jun. 25, 2014, 5 pages (with English translation).
Response to Office Action in MX App. Ser. No. MX/a/2012/002011 filed on Jan. 16, 2014, 20 pages (with English translation).
Response to Office Action in MX App. Ser. No. MX/a/2012/014776, dated Jan. 7, 2015, 20 pages (with English translation).
Response to Office Action in MX App. Ser. No. MX/a/2012/014776, dated Jun. 20, 2014, 9 pages (with English translation).
Response to Office Action in MX App. Ser. No. MX/a/2013/009931, dated Dec. 9, 2014, 24 pages (with English translation).
Response to office action in NZ App. Ser. No. 566793, dated Jan. 17, 2010, 17 pages.
Response to office action in PH App. Ser. No. 1-2007-502319, dated Feb. 6, 2012, 19 pages.
Response to office action in PK App. Ser. No. 1024/2006, dated Apr. 20, 2009, 14 pages.
Response to office action in PK App. Ser. No. 1024/2006, dated Apr. 7, 2008, 17 pages.
Response to office action in PK App. Ser. No. 1024/2006, dated Jan. 29, 2009, 6 pages.
Response to office action in PK App. Ser. No. 155/2005, dated Jan. 4, 2008, 34 pages.
Response to office action in PK App. Ser. No. 375/2008, dated Apr. 8, 2009, 19 pages.
Response to office action in PK App. Ser. No. 375/2008, dated Dec. 20, 2008, 1 page.
Response to office action in PK App. Ser. No. 375/2008, dated Sep. 1, 2009, 20 pages.

(56) References Cited

OTHER PUBLICATIONS

Response to office action in RU App. Ser. No. 2006134254, dated Dec. 15, 2006, 23 pages (with English translation).
Response to office action in RU App. Ser. No. 2006134254, dated Nov. 20, 2007, 32 pages (with English translation).
Response to office action in RU App. Ser. No. 2008110932, dated Jan. 26, 2009, 29 pages (with English translation).
Response to Office Action in RU App. Ser. No. 2012103471, dated Jul. 21, 2014, 7 pages (with English translation).
Response to office action in RU App. Ser. No. 2012103471, dated Nov. 18, 2014, 17 pages (with English translation).
Response to Office Action in RU App. Ser. No. 2012158142, dated Apr. 13, 2015 (with English translation).
Response to Office Action in RU App. Ser. No. 2013139556, dated Dec. 25, 2013, 10 pages (with English translation).
Response to Office Action in SG App. Ser. No. 201108602-2, dated May 22, 2014, 37 pages.
Response to office action in TW App. Ser. No. 095130665, dated May 28, 2012, 379 pages (with English translation).
Response to Office Action in U.S. Appl. No. 13/923,858, filed Apr. 1, 2015, 12 pages.
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to Office Action in U.S. Appl. No. 11/662,425, filed on May 20, 2014, 8 pages.
Response to office action in U.S. Appl. No. 12/031,568, dated Aug. 12, 2011, 12 pages.
Response to office action in U.S. Appl. No. 12/031,568, dated Jun. 2, 2010, 13 pages.
Response to Office Action in U.S. Appl. No. 12/039,381, dated Apr. 3, 2014, 7 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 21 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 13/983,891, dated Feb. 27, 2014, 6 pages.
Response to Office Action in U.S. Appl. No. 14/002,018, dated Jul. 18, 2014, 8 pages.
Response to Office Action in U.S. Appl. No. 14/002,018, filed on May 28, 2014, 7 pages.
Response to office action in VN App. Ser. No. 1-2008-00723, dated May 10, 2010, 7 pages (with English translation).
Response to Office Action under 37 C.F.R. §1.111 for U.S. Appl. No. 12/523495, filed on Dec. 7, 2011, 13 pages.
Response to Office Action under 37 C.F.R. §1.111 for U.S. Appl. No. 13/083,338, filed on Apr. 8, 2011, 6 pages.
Response to Office Action under 37 C.F.R. §1.111 for U.S. Appl. No. 13/083,338, filed on Sep. 6, 2012, 8 pages.
Response to Office Action under 37 C.F.R.S 1.111 and Information Disclosure Statement for U.S. Appl. No. 11/997,719, filed Jul. 3, 2013, 26 pages.
Response to Restriction Requirement for U.S. Appl. No. 11/997,543, filed on Mar. 22, 2011, 4 pages.
Response to Restriction Requirement for U.S. Appl. No. 12/301,353, filed on Nov. 23, 2010, 4 pages.
Response to Restriction Requirement for U.S. Appl. No. 12/524,754, filed on Dec. 1, 2011, 2 pages.
Response to Restriction Requirement in U.S. Appl. No. 11/892,785, dated Oct. 30, 2009, 16 pages.
Response to Restriction Requirement in U.S. Appl. No. 13/238,085, dated Oct. 4, 2013, 3 pages.
Response to Restriction Requirement in U.S. Appl. No. 11/065,631, dated Nov. 26, 2007, 16 pages.
Response to Restriction Response in U.S. Appl. No. 13/805,826, dated Jun. 2, 2014, 2 pages.
Response to the European Search Report for European Application No. 06782407 filed on Nov. 8, 2010, 105 pages.
Response to the Office Action for European Application No. 06782407 filed on Jan. 23, 2012, 17 pages.
Response to the Office Action issued for IN App. Ser. No. 6415/CHENP/2008 filed on Jan. 17, 2014, 16 pages.
Response to the Office Action issued for Japanese Application No. 2007-529565 filed on Feb. 3, 2012, 44 pages with English full translation.
Restriction Requirement for U.S. Appl. No. 11/997,543, dated Feb. 23, 2011, 9 pages.
Restriction Requirement for U.S. Appl. No. 12/092,539, dated Oct. 29, 2010, 8 pages.
Restriction Requirement for U.S. Appl. No. 12/301,353, dated Oct. 29, 2010, 11 pages.
Restriction Requirement for U.S. Appl. No. 12/439,339, dated Jul. 29, 2011, 10 pages.
Restriction Requirement for U.S. Appl. No. 12/524,754, dated Nov. 3, 2011, 11 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Restriction Requirement in U.S. Appl. No. 11/065,631, dated Oct. 25, 2007, 8 pages.
Roberts et al., "Antiangiogenic and Antitumor Activity of a Selective PDGFR Tyrosine Kinase Inhibitor, CP-673,451", Cancer Research., 65, 957-966, 2005.
Robinson et al, "Characterization of Tumor Size Changes Over Time From the Phase 3 Study of (E7080) Lenvatinib in Differentiated Cancer of the Thyroid (Select)", The Poster, No. 1031P, presented at European Society for Medical Oncology 2014 Congress, Sep. 26-30, 2014, 1 page.
Rosen and Goldberg, "Scatter Factor and Angiogenesis," Advances in Cancer Research, 1995, 67:257-279.
Rowe, R.C. et al. (ed.), Handbook of Pharmaceutical Excipients, 5th ed. Pharmaceutical Press, London, 2006, pp. 336-343.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Russian Decision of Grant directed at Appl. No. 2008149948115(065561) received on Nov. 9, 2011, 16 pages with English translation.
Russian Office Action dated Apr. 11, 2012 for App. Ser. No. 2012103471, 6 pages (with English translation).
Russian Office Action dated Jan. 19, 2005 for App. Ser. No. 2003114740 (with English translation), 3 pages.
Russian Office Action dated Jun. 29, 2004 for App. Ser. No. 2003114740 (with English translation), 16 pages.
Russian Office Action directed at Appl. No. 2008149948115(065561) issued on May 24, 2011, 8 pages with English translation.
Russian Response to Office Action directed at Appl. No. 2008149948115(065561) filed on Jul. 27, 2011, 14 pages with English translation.
Saeki et al., "Concurrent overexpression of Ets-1 and c-Met correlates with a phenotype of high cellular motility in human esophageal cancer," International J Cancer, 2002, 98(1):8-13.
Salassidis et al., "Translocation t(1 0; 14) (q11.2; q22.1) Fusing the Kinectin to the RET Gene Creates a Novel Rearranged Form (PTC8)

(56) References Cited

OTHER PUBLICATIONS of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," Cancer Invest., 23(8):712-726 (2005).
Salvatore et al., "Molecular profile of hyalinizing trabecular tumours of the thyroid: High prevalence of RET/PTC rearrangements and absence of B-raf and N-raspoint mutations", European Journal of Cancer, 41:816-821 (2005).
Sandler et al., "Phase III trial of gemcitabine plus cisplatin versus cisplatin alone in patients with locally advanced or metastatic non-small-cell lung cancer," J. Clin. Oncol., 18(1):122-130 (2000).
Sanger et al., "DNA sequencing with chain-terminating inhibitors", Proc. Natl. Acad. Sci. USA 74:5463 (1977).
Santoro et al., "Drug insight: Small-molecule inhibitors of protein kinases in the treatment of thyroid cancer," Nat. Clin. Pract. Endocrinol. Metab., 2(1):42-52 (2006).
Santoro et al., "Minireview: RET: normal and abnormal functions," Endocrinology, 145:5448-5451 (2004).
Santoro et al., "Molecular Mechanisms of RET Activation in Human Cancer," Ann. N.Y. Academy of Sciences, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," Oncogene, 21:3314-3333 (2002).
Schlumberger et al., "A phase 3, multicenter, double-blind, placebo-controlled trial of lenvatinib (E7080) in patients with $^{131}$I-refractory differentiated thyroid cancer (SELECT)," Am Soc Clin Oncol., Annual Meeting Abstract LBA6008, 2012, 4 pages.
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Schlumberger et al., "Lenvatinib versus Placebo in Radioiodine-Refractory Thyroid Cancer," N Engl J Med., 372(7):621-630, Feb. 12, 2015.
Search Report in EP App. Ser. No. 09705712.9, dated Aug. 7, 2014, 6 pages.
Search Report in EP App. Ser. No. 11798224.9, dated Mar. 21, 2014, 1 page.
Search Report in EP App. Ser. No. 11798224.9, dated Mar. 4, 2014, 6 pages.
Search Report in EP App. Ser. No. 12774278.1, dated Aug. 14, 2014, 8 pages.
Search Report in EP App. Ser. No. 12786619.2, dated Dec. 15, 2014, 6 pages.
Search Report in EP App. Ser. No. 12793322.4, dated May 26, 2015, 9 pages.
Search Report in EP App. Ser. No. 12793322.4, dated Sep. 10, 2015, 13 pages.
Second Preliminary Amendment and Response to Restriction Requirement for U.S. Appl. No. 12/092,539, filed on Nov. 22, 2010, 5 pages.
Section 18 Submission in IL App. Ser. No. 223695, dated May 4, 2015, 4 pages (with English translation).
Sekido et al., "Preferential Expression of c-kit Protoonocogene Transcripts in Small Cell Lung Cancer," Cancer Res., 51:2416-2418 (1991).
Sennino and McDonald, "Controlling escape from angiogenesis inhibitors", Nature Rev Cancer, 12:699-709, Oct. 2012.
Sharma et al., "Thyroid Cancer," Feb. 18, 2015, pp. 1-16.
Shiang et al., "Mutations in the transmembrane domain of FGFR3 cause the most common genetic form of dwarfism, achondroplasia," Cell., 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).

Shimizu et al., "Orally active anti-proliferation agents: novel diphenylamine derivatives as FGF-R2 autophosphorylation inhibitors," Bioorganic and Medicinal Chemistry Letters, 14(4):875-879 (2004).
Shirai, et al., ""Role of low-substituted hydroxypropylcellulose in dissociation and bioavalability of novel fine granule system for masking bitter taste,"" Biol. Pharm. Bull, 17(3): 427-431 (1994).".
Shumaker et al., "Effect of lenvatinib (E7080) on the QTc interval: results from a thorough QT study in healthy volunteers," Cancer Chemother Pharmacol., published online Mar. 23, 2014, 9 pages (with English abstract).
Siegel et al., "Sorafenib: Where Do We Go from Here?," *Hepatology*, 52:360-369 (2010).
Siemeister et al., "ZK304709, the oral Multitarget Tumor Growth Inhibitor™, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Sondergaard et al., Differential sensitivity of melanoma cell lines with $BRAF^{v600E}$ mutation to the specific Raf inhibitor PLX4032, J Translational Med., 2010, 8:39, 11 pages.
Spacey et al., "Indolocarbazoles, Potent and Selective Inhibitors of Platelet-Derived Growth Factor Receptor Autophosphorylation," *Biochemical Pharmacology*, 55:261-271 (1998).
St. Bernard et al., "Fibroblast Growth Factor Receptors as Molecular Targets in Thyroid Carcinoma," Endocrinology, Mar. 2005, 146(3):1145-1153.
Stahl and Wermuth, "Handbook of Pharmaceutical Salts: Properties, selection, and use," 2002, pp. 117-122.
Stjepanovic and Capdevila, "Multikinase inhibitors in the treatment of thyroid cancer: specific role of lenvatinib," Biologics: Targets and Therapy, 8:129-139, Aug. 2014.
Strohmeyer et al., "Expression of the hst-1 and c-kit Protoonocogenes in Human Testicular Germ Cell Tumors," Cancer Res., 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Se. No. 207089, 7 pages (with English translation).
Submission Document Before the Patent Office dated Mar. 14, 2013 for IL App. Ser. No. 205512, 12 pages (with English translation).
Submission Document Before the Patent Office for CL App. Ser. No. 2012-00412, dated Aug. 31, 2012, 6 pages (with English translation).
Submission Document Before the Patent Office for EP App. Ser. No. 03791389.4, dated Dec. 20, 2012, 4 pages.
Submission Document Before the Patent Office for EP App. Ser. No. 08846814.5, dated Jan. 3, 2013, 102 pages.
Submission Document Before the Patent Office for EP App. Ser. No. 8704376.6, dated Jan. 2, 2013, 22 pages.
Submission Document Before the Patent Office re Observation dated Feb. 16, 2013 for CN App. Ser. No. 200980103218.7, 8 pages (with English translation).
Submission Document in CL App. Ser. No. 2012-00412, dated Aug. 12, 2014, 2 pages (with English translation).
Submission Document in EP App. Ser. No. 09705712.9, dated Feb. 24, 2015, 196 pages.
Submission Document in HU App. Ser. No. P0302603, dated Jul. 7, 2015, 45 pages (with English translation).
Submission Document in MX App. Ser. No. MX/a/2014/010594, dated Sep. 4, 2014, 70 pages (with English translation).
Submission Document in MY App. Ser. No. PI2011700172, dated Nov. 4, 2014, 3 pages.
Submission Document in PH App Ser. No. 1-2011-502441, dated May 22, 2015, 25 pages.
Submission Document re figures in AR App. Ser. No. P110100513, dated Oct. 22, 2014, 3 pages.
Submission Document re Petition on Oct. 2, 2013 in CL App. Ser. No. 2012-00412, 22 pages (with English translation).
Submission Document re RCE and Amendment in U.S. Appl. No. 12/031,568, dated Oct. 26, 2010, 23 pages.

(56) References Cited

OTHER PUBLICATIONS

Submission Document re RCE and Information Disclosure Statement in U.S. Appl. No. 11/065,631, dated Oct. 8, 2008, 7 pages.
Submission Document re RCE and Information Disclosure Statement in U.S. Appl. No. 12/558,982, dated May 9, 2012, 36 pages.
Submission Document re RCE and Information Disclosure Statement on Oct. 18, 2013, in U.S. Appl. No. 12/524,754, 17 pages.
Submission Document re RCE and Information Disclosure Statement on Sep. 19, 2013 in U.S. Appl. No. 12/741,682, 19 pages.
Submission Document re RCE in U.S. Appl. No. 12/031,568, dated Aug. 30, 2012, 12 pages.
Submission Document re RCE in U.S. Appl. No. 12/031,568, dated Jan. 18, 2012, 11 pages.
Submission Document re RCE in U.S. Appl. No. 12/558,982, dated Nov. 29, 2011, 13 pages.
Submission Document re RCE in U.S. Appl. No. 12/741,682, dated Aug. 14, 2014, 1 page.
Submission Document re RCE in U.S. Appl. No. 13/205,328, dated Sep. 10, 2013, 12 pages.
Submission Documents Before the Patent Office for CN App. Ser. No. 201080030508.6, dated May 27, 2013, 7 pages (with English translation).
Submission Documents Before the Patent Office for KR App. Ser. No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents in EG App. Ser. No. PCT 283/2012, dated Jan. 18, 2015, 26 pages (with English translation).
Submission Documents in TW App. Ser. No. 100104281, dated Mar. 9, 2015, 12 pages (with English translation).
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission documents re RCE filed in U.S. Appl. No. 11/997,719, dated Dec. 11, 2013, 10 pages.
Submission Documents re RCE filed in U.S. Appl. No. 12/524,754, dated May 13, 2014, 1 page.
Submission documents re RCE filed in U.S. Appl. No. 12/741,682, dated Jan. 17, 2014, 1 page.
Submission Documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Submission documents re RCE in U.S. Appl. No. 12/439,339, dated Jan. 27, 2014, 1 page.
Submission documents re RCE in U.S. Appl. No. 12/524,754, filed on Feb. 3, 2014, 1 page.
Submission Documents re Request for Continued Examination filed in U.S. Appl. No. 12/741,682, dated May 6, 2014, 1 page.
Submission Documents re Request for Continued Examination filed in U.S. Appl. No. 13/083,338, dated May 6, 2014, 1 page.
Submission documents re Request for Continued Examination in U.S. Appl. No. 13/205,328, dated Apr. 28, 2014, 1 page.
Submission in EP App. Ser. No. 04807580.8, dated Jun. 13, 2014, 18 pages.
Submission of Amendments and Complete Specification dated Apr. 10, 2013 for in IN App. Ser. No. 1571/CHENP/2007, 15 pages.
Submission of Claims in IL App. Ser. No. 223695, dated Jan. 17, 2015, 16 pages.

Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012, 16 pages.
Submission of Document re Request for Examination in CO App. Ser. No. 12-022608, submitted on Jun. 12, 2012, 6 pages.
Submission of Documents before the Patent Office for CN App. Ser. No. 200880115011.7, dated Apr. 11, 2013, 10 pages (with English translation).
Submission of Documents before the Patent Office for CN App. Ser. No. 200980103218.7, dated Mar. 13, 2013, 6 pages (with English translation).
Submission of Documents Before the Patent Office for IL App. Ser. No. 175363, dated Feb. 27, 2013, 22 pages.
Submission of Documents re Amendment in UA App. Ser. No. a2012 03132, submitted on May 22, 2012, 11 pages (with English translation).
Submission of Documents re Claim 3 and Figure 3 for KR App. Ser. No. 10-2009-7005657, filed on Jul. 13, 2012, 5 pages.
Submission of Reference Materials in KR App. Ser. No. 10-2008-7013685, filed Jul. 5, 2013, 43 pages, (with English translation).
Sun et al., " Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119 (2003).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplemental Search Report in EP App. Ser. No. 05719973.9, dated Dec. 6, 2007, 3 pages.
Supplemental Search Report in EP App. Ser. No. 05719976.2, dated Dec. 6, 2007, 3 pages.
Supplementary European Search Report for App. Ser. No. 01976786.2, dated Jul. 6, 2004, 6 pages.
Supplementary European Search Report for App. Ser. No. 08 70 4376, dated Jun. 14, 2012.
Supplementary European Search Report for App. Ser. No. 08846814.5, issued on Jun. 18, 2012.
Supplementary European Search Report issued Jul. 5, 2012, in European Patent Application No. 08846814.5, 1 page.
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Taguchi et al., "A novel orally active inhibitor of VEGF receptor tyrosine kinases KRN951: Anti-angiogenic and anti-tumor activity against human solid tumors," Proc Am Assoc Cancer Res., 45:1070-1071, Abstract 2575, 2004.
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 24 pages.
Tahara et al., "Lenvatinib in Radioactive Iodine-refractory Differentiated Thyroid Cancer: Results of the Phase 3 trial (SELECT trial)," Jan. 1, 2001, Abstract and Presentation Document, 12$^{th}$ Annual Meeting of Japanese Society of Medical Oncology, Jul. 17, 2014, 21 pages.
Takahashi et al, "Phase II Study of Lenvatinib, A Multitargeted Tyrosine Kinase Inhibitor, in Patients With All Histologic Subtypes of Advanced Thyroid Cancer (Differentiated, Medullary, and Anaplastic)", The Poster, presented at the European Society for Medical Oncology 2014 Congress, Sep. 26-30, 2014, 1 page.
Takahashi et al., "A case of inoperable scirrhous gastric cancer that responded remarkably to a combination of TS-1+paclitaxel and showed complete loss of ascites," *Japanese Journal of Cancer and Chemotherapy*, 31(7):1093-1095 (2004).

(56) References Cited

OTHER PUBLICATIONS

Takeda et al., "AZD2171 shows potent anti-tumor activity against gastric cancer expressing variant K-SAM/FGFR2," Abstract #3785, *Proceeding of the American Association for Cancer Research*, 47:890 (2006).
Tamura et al., "Molecular Characterization of Undifferentiated-Type Gastric Carcinoma," Laboratory Investigation, 81(4):593-598, Apr. 2001.
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," Cancer Res., 59:4297-4300 (1999).
The Pharmacology of Monoclonal Antibody, vol. 113, Chapter 11, Rosenburg and Moore ed., Springer Verlag (1994) pp. 269-315.
Third Office Action dated Feb. 25, 2013 for CN App. Ser. No. 200880115011.7, 6 pages (with English translation).
Thomas et al., "The Eosinophil and its Role in Asthma," Gen. Pharmac., 27(4)593-597 (1996).
Thyroid Cancers, Endocrine and Metabolic Disorders, http://www.merkmanuals.com/professional/print/sec12/ch152/ch152j.html Mar. 16, 2011, 4 pages.
Tian et al., "Activating c-kit Gene Mutations in Human Germ Cell Tumors," *American Journal of Pathology*, 154(6):1643-1647 (1999).
To and Tsao, "The roles of hepatocyte growth factor/scatter factor and Met receptor in human cancers (Review)," *Oncology Reports*, 1998, 5:1013-1024.
Tohyama et al, "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis," Int. J. Cancer, 89:242-250 (2000).
Tong et al., "Vascular normalization by vascular endothelial growth factor receptor 2 blockade induces a pressure gradient across the vasculature and improves drug penetration in tumors," Cancer Res., 64:3731-3736 (2004).
Toshiyuki et al., "Thermal recording materials with improved background stability," Database CA (Online) Chemical Abstracts Service, Columbus, OH, US (Feb. 20, 1996) (XP002443195), 1 page.
Transmittal of Information Disclosure Statement, Terminal Disclaimer, Request for Continued Examination, and Response to Office Action under 37 C.F.R. §1.116 for U.S. Appl. No. 11/997,719, filed on Jul. 6, 2011, 15 pages.
Traxler et al., "AEE788; A dual family epidermal growth factor receptor/ErbB2 and vascular endothelial growth factor receptor tyrosine kinase inhibitor with antitumor and antiangiogenic activity," Cancer Res., 64:4931-4941 (2004).
Trudel et al., "CHIR-258, a novel, multitargeted tyrosine kinase inhibitor for the potential treatment of t(4;14) multiple myeloma," Blood, 105:2941-2948 (2005).
Trudel et al, "Inhibition of fibroblast growth factor receptor 3 induces differentiation and apoptosis in t(4;14) myeloma," Blood, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signaling: from development to cancer," Nature Reviews, Cancer, 10:116-129 (2010).
U.S. Certificate of Correction in U.S. Appl. No. 12/524,754, dated Aug. 11, 2015, 1 page.
U.S. Certificate of Correction in U.S. Appl. No. 13/624,278, dated Aug. 18, 2015, 1 page.
U.S. Final Office Action in U.S. Appl. No. 10/797,903, dated Jul. 23, 2008, 11 pages.
U.S. Notice of Allowance for U.S. Appl. No. 12/244,227, dated Oct. 22, 2010, 32 pages.
U.S. Office Action for U.S. Appl. No. 10/797,903, issued on Aug. 20, 2009, 10 pages.
U.S. Office Action for U.S. Appl. No. 10/577,531, issued on Sep. 23, 2008, 17 pages.
U.S. Office Action for U.S. Appl. No. 10/797,903, issued on Apr. 1, 2010, 11 pages.
U.S. Office Action for U.S. Appl. No. 10/797,903, issued on Dec. 11, 2007, 12 pages.
U.S. Office Action for U.S. Appl. No. 10/797,903, issued on Sep. 1, 2010, 7 pages.
U.S. Office Action for U.S. Appl. No. 11/293,785, issued on Sep. 4, 2007, 18 pages.
U.S. Office Action for U.S. Appl. No. 11/347,749, issued on Feb. 9, 2009.
U.S. Office Action for U.S. Appl. No. 11/662,425, issued on May 3, 2010, 16 pages.
U.S. Office Action for U.S. Appl. No. 11/662,425, issued on Sep. 28, 2010, 35 pages.
U.S. Office Action for U.S. Appl. No. 11/997,543, issued on Feb. 23, 2011, 9 pages.
U.S. Office Action for U.S. Appl. No. 11/997,543, issued on May 19, 2011, 38 pages.
U.S. Office Action for U.S. Appl. No. 11/997,543, issued on Nov. 9, 2011, 12 pages.
U.S. Office Action for U.S. Appl. No. 11/997,719, issued on Apr. 6, 2011, 6 pages.
U.S. Office Action for U.S. Appl. No. 11/997,719, issued on Sep. 3, 2010, 10 pages.
U.S. Office Action for U.S. Appl. No. 12/092,539, issued on Jan. 7, 2011.
U.S. Office Action for U.S. Appl. No. 12/092,539, issued on Jun. 28, 2011, 3 pages.
U.S. Office Action for U.S. Appl. No. 12/092,539, issued on May 9, 2011, 10 pages.
U.S. Office Action for U.S. Appl. No. 12/094,492, issued on Mar. 24, 2011, 16 pages.
U.S. Office Action for U.S. Appl. No. 12/301,353, issued on Jan. 24, 2011, 10 pages.
U.S. Office Action for U.S. Appl. No. 12/400,562, issued on Mar. 31, 2010, 11 pages.
U.S. Office Action for U.S. Appl. No. 12/439,339, issued on Mar. 30, 2012, 6 pages.
U.S. Office Action for U.S. Appl. No. 12/439,339, issued on Nov. 14, 2011, 44 pages.
U.S. Office Action for U.S. Appl. No. 12/523,495, issued on Dec. 27, 2011, 11 pages.
U.S. Office Action for U.S. Appl. No. 12/523,495, issued on Sep. 27, 2011, 37 pages.
U.S. Office Action for U.S. Appl. No. 12/524,754, issued on Dec. 19, 2011, 53 pages.
U.S. Office Action for U.S. Appl. No. 12/741,682, issued on Apr. 30, 2012, 50 pages.
U.S. Office Action for U.S. Appl. No. 12/864,817, issued on Dec. 16, 2011, 4 pages.
U.S. Office Action for U.S. Appl. No. 12/864,817, issued on May 19, 2011, 11 pages.
U.S. Office Action for U.S. Appl. No. 12/864,817, issued on Nov. 3, 2011, 11 pages.
U.S. Office Action for U.S. Appl. No. 13/083,338, issued on Apr. 12, 2012, 8 pages.
U.S. Office Action for U.S. Appl. No. 13/083,338, issued on Jun. 8, 2012, 55 pages.
U.S. Office Action for U.S. Appl. No. 13/083,338, issued on Nov. 23, 2012, 38 pages.
U.S. Office Action for U.S. Appl. No. 13/205,328, issued on Jan. 12, 2012, 37 pages.
U.S. Office Action for U.S. Appl. No. 13/205,328, issued on May 1, 2012, 21 pages.

(56) References Cited

OTHER PUBLICATIONS

U.S. Office Action for U.S. Appl. No. 13/322,961, issued on Sep. 25, 2012, 62 pages.
U.S. Office Action for U.S. Appl. No. 10/420,466, issued on Apr. 13, 2005, 16 pages.
U.S. Supplemental Notice of Allowance in U.S. Appl. No. 12/315,291, dated Jul. 21, 2011, 4 pages.
Ueda et al., "VGA1155, a Novel Binding Antagonist of VEGF, Inhibits Angiogenesis in Vitro and in Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
US Office Action for U.S. Appl. No. 11/997,543, dated Sep. 30, 2013, 88 pages.
US Response to Notice of Non-Compliant Amendment dated Jan. 13, 2005 for U.S. Appl. No. 10/420,466, 17 pages.
US Response to Notice of Non-Compliant Amendment dated Jan. 18, 2005 for U.S. Appl. No. 10/420,466.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
van Oers et al., "A simple and fast method for the simultaneous detection of nine fibroblast growth factor receptor 3 mutations in bladder cancer and voided urine," Clin. Cancer Res., 11:7743-7748 (2005).
Varvoglis et al., "Chemical Transformations Induced by Hypervalent Iodine Reagents," Tetrahedron, 1997, 53(4):1179-1255.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.
Vianna et al., "The histological rarity of thyroid cancer", Brazilian Journal of Otorhinolaryngology, 2012, 78(4):48-51.
Vippagunta et al., "Crystalline solids," Advanced Drug Delivery Reviews, 48:3-26 (2001).
Vogel et al., "Sensing extracellular matrix: an update on discoidin domain receptor function," Cell Signaling, 18:1108-1116 (2006).
Voluntary Amendment filed in CA App. Ser. No. 2704000, filed Aug. 6, 2013, 6 pages.
Voluntary Amendment filed in CA App. Ser. No. 2802644, dated Nov. 22, 2013, 25 pages.
Voluntary Amendment filed on Aug. 11, 2010 for CN App. Ser. No. 200710007097.9, 12 pages (with English translation).
Voluntary Amendment filed on Aug. 19, 2010 for CA App. Ser. No. 2426461, 2 pages.
Voluntary Amendment filed on Aug. 30, 2006 for AU App. Ser. No. 2006203099, 16 pages.
Voluntary Amendment filed on Feb. 16, 2012 for BR Patent App. No. BR112012003592-4, 18 pages (with partial English translation).
Voluntary Amendment filed on Feb. 21, 2007 for AU App. Ser. No. 2006203099.
Voluntary Amendment filed on Feb. 27, 2007 for AU App. Ser. No. 2006236039, 10 pages.
Voluntary Amendment filed on Feb. 9, 2010 for AU App. Ser. No. 2005283422, 12 pages.
Voluntary Amendment filed on Jul. 6, 2010 for AU App. Ser. No. 2005283422, 21 pages.
Voluntary Amendment filed on Sep. 10, 2010 for HU App. Ser. No. P0302603, 36 pages (with English translation).
Voluntary Amendment for Australian App. Ser. No. 2010285740, filed on Nov. 21, 2011, 3 pages.
Voluntary Amendment for Chinese counterpart of App. No. PCT/JP2010/063804, filed on Jan. 5, 2012, 8 pages (with English translation).
Voluntary Amendment for counterpart Canadian patent application, filed on Feb. 16, 2012, 3 pages.
Voluntary Amendment for Russian App. Ser. No. 2012103471, filed on Feb. 1, 2012, 3 pages (with English translation).
Voluntary Amendment for Thailand App. Ser. No. 1201000221, filed on Feb. 17, 2012, 8 pages.
Voluntary Amendment in BR App. Ser. No. PI0616799/3, dated May 29, 2009, 21 pages.
Voluntary Amendment in CA App. Ser. No. 2605854, dated Oct. 23, 2007, 14 pages.
Voluntary Amendment in CA App. Ser. No. 2661702, dated Feb. 24, 2009, 4 pages.
Voluntary Amendment in CA App. Ser. No. 2679602, dated Aug. 20, 2009, 6 pages.
Voluntary Amendment in ID App. Ser. No. W-00201201031, dated Nov. 5, 2014, 2 pages (with English translation).
Voluntary Amendment in IN App. Ser. No. 1424/CHENP/2008, dated Mar. 24, 2008, 257 pages.
Voluntary Amendment in IN App. Ser. No. 5625/CHENP/2009, dated Sep. 23, 2009, 147 pages.
Voluntary Amendment in LK App. Ser. No. 14703, dated Mar. 31, 2011, 256 pages.
Voluntary Amendment in MX App. Ser. No. MX/a/2014/010594, dated Oct. 23, 2014, 4 pages (with English translation).
Voluntary Amendment in TW App. Ser. No. 095130665, dated Mar. 20, 2009, 36 pages (with English translation).
Voluntary Amendments in AU App. Ser. No. 2007288793, dated May 29, 2009, 9 pages.
Voluntary Amendments in AU App. Ser. No. 2008217931, dated Nov. 18, 2009, 17 pages.
Voluntary Brief Amendments for Venezuelan App. Ser. No. 2011-000193, filed on Dec. 21, 2011, 8 pages (with English translation).
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14):2398-2406 (1994) (English abstract).
Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Wang et al., "A Convenient Set of Bidentate Pyridine Ligands for Combinatorial Synthesis," Tetrahedron Lett., 40:4779-1478 (1999).
Wang et al., "Phase II study of gemcitabine and carboplatin in patients with advanced non-small-cell lung cancer," Cancer Chemother Pharmacol., 60(4):601-607 (2007).
Wang et al., "The Expression of the Proto-Oncogene C-Kit in the Blast Cells of Acute Myeloblastic Leukemia," Leukemia, 3(10):699-702 (1989).
Wang, "Everolimus in renal cell carcinoma," Drugs of Today, Aug. 2010, 46(8), abstract, 1 page.
Waterman, M., "Computer Analysis of Nucleic Acid Sequences", Methods in Enzymology, 164:765-793 (1988).
Watson et al, "Inhibition of c-Met as a therapeutic strategy for esophageal adenocarcinoma," Neoplasia, 2006, 8(11):949-955.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 24-28, 2001, New Orleans, LA, USA, abstract 3126, 2 pages.
Wells et al., "Targeting the RET Pathway in Thyroid Cancer," Clin. Cancer Res., 15:7119-7123 (2009).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Werner et al., "Gastric adenocarcinoma: pathomorphology and molecular pathology," J. Cancer Res. Clin. Oncology, 127:207-216 (2001) (English abstract).

(56) References Cited

OTHER PUBLICATIONS

Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. And Lipman, DJ., "Rapid similarity searches of nucleic acid and protein data banks", Natl. Acad. Sci, U.S.A. 80:726-730 (1983).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Wirth et al, "Treatment-Emergent Hypertension and Efficacy in the Phase 3 Study of (E7080) Lenvatinib in Differentiated Cancer of the Thyroid (Select)", The Poster, No. 1030P, presented at the European Society for Medical Oncology 2014 Congress, Sep. 26-30, 2014, 1 page.
Wisniewski et al.,"Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research, 64, 6652-6659. 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Wozniak et al., "Randomized trial comparing cisplatin with cisplatin plus vinorelbine in the treatment of advanced non-small-cell lung cancer: a Southwest Oncology Group study," J Clin. Oncol., 16(7):2459-2465 (1998).
Written Amendment filed on Jun. 16, 2009 for JP App. Ser. No. 2009-123432, 12 pages (with English translation).
Written Amendment filed on Sep. 21, 2011 for JP App. Ser. No. 2011-527665, 2 pages (with English translation).
Written Statement filed on Jun. 16, 2009 for JP App. Ser. No. 2009-123432, 32 pages (with English translation).
Written Statement filed on Sep. 21, 2011 for JP App. Ser. No. 2011-527665, 2 pages (with English translation).
Written Submission regarding hearing in in App. Ser. No. 1571/CHENP/2007 filed on Jan. 23, 2014, 8 pages.
Written Verdict in SA App. Ser. No. 06270287, dated Feb. 17, 2013, 11 pages (with English translation).
Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Yamada et al., "Phase 1 Dose-Escalation Study and Biomarker Analysis of E7080 in Patients with Advanced Solid Tumors," Clinical Cancer Research, Mar. 2011, 17(8):2528-2537 (with supplementary data).
Yamada et al., "New technique for staining," Monthly Medical Technology Supplementary vol. (Apr. 1999) (with English translation), 13 pages.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, AACR, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, AACR, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR, Washington, DC.* (Apr. 1-5, 2006).
Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*, 45:1070-1071 (Mar. 2004).
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066 (with English translation).
Yanagihara et al., "Development and biological analysis of peritoneal metastasis mouse models for human scirrhous stomach cancer," Cancer Sci., 96(6):323-332 (2005).
Yang et al., "RG7204 (PLX4032), a Selective BRAF V600E Inhibitor, Displays Potent Antitumor Activity in Preclinical Melanoma Models," Cancer Res., 2010, 70(13):5518-5527.
Yigitbasi et al., "Tumor Cell and Endothelial Cell Therapy of Oral Cancer by Dual Tyrosine Kinase Receptor Blockade", Cancer Research, 64, 7977-7984, 2004.
Yokota, "ASCO report: Gastrointestinal Cancer field/ASCO Hokoku Shokakigan Ryoiki," Gan Bunshi Hyoteki Chiryo, 2010, 8(4):271-283.
Yu, "Amorphous Pharmaceutical Solids:Preparation Characterization and Stabilization," Advanced Drug Delivery Reviews, 48:27-42 (2001) (XP009065056).
Zhang et al., "Induction of apoptosis in EMT-6 breast cancer cell in line by a Sigma-2 selective ligand," Am. Assoc. Cancer Research, Abstract 5353, 2005, 2 pages.
Zhang et al , "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor a in Endothelial Cells of Hepatocellular Carcinoma Associated with High Metastatic Potential," Clin. Cancer Res., 11(24):8557-8563 (2005).
Zhang et al., "Synergic antiproliferative effect of DNA methyltransferase inhibitor in combination with anticancer drugs in gastric carcinoma," Cancer Sci., Sep. 2006, 97(9):938-944.
Zhong et al., "Mechanisms underlying the synergistic effect of SU5416 and cisplatin on cytotoxicity in human ovarian tumor cells," Inter'l J Oncol., 25(2):445-451, 2004.
Zhou et al., "Correlation Research on VEGF Testing in Primary Gastric Cancer and Clinical Pathology Factor," Journal of Practical Oncology, 20(2):103-105 (Apr. 25, 2006) with English translation.
Zhu et al., "Fibroblast growth factor receptor 3 inhibition by short hairpin RNAs leads to apoptosis in multiple myeloma," Mol. Cancer Ther., 4(5):787-798 (2005).
Zhu et al., "Inhibition of human leukemia in an animal model with human antibodies directed against vascular endothelial growth factor receptor 2. Correlation between antibody affinity and biological activity," Leukemia, 17:604-611 (2003).
Zieger et al., "Role of activating fibroblast growth factor receptor 3 mutations in the development of bladder tumors," Clin. Cancer Res., 11:7709-7719 (2005).
Zimmermann et al., "Potent and Selective Inhibitors of the Abl— Kinase:Phenylamino-Pyrimidine (PAP) Derivatives", Bioorganic and Medicinal Chemistry Letters., 7(2):187-192, 1997.

(56) References Cited

OTHER PUBLICATIONS

Zimmermann, "Electrical Breakdown, Electropermeabilization and Electrofusion", Rev. Physiol. Biochem. Pharmacol. 105:176-260 (1986).
Zurita et al., "A cytokine and angiogenic factor (CAF) analysis in—plasma for selection of sorafenib therapy in patients with metastatic renal cell carcinoma," Annals of oncology, Apr. 2011, 23(1):46-52.
Zurita et al., "Circulating biomarkers for vascular—endothelial growth factor inhibitors in renal cell carcinoma," Cancer, May 2009, 115(S10):2346-2354.
Amendment to Specification in IL App. Ser. No. 217197, dated Dec. 24, 2015, 5 pages (with English tmnslation).
International Search Report and Written Opinion in International Application No. PCT/JP2014/063134, dated Sep. 9, 2014, 8 pages.
Kato et al., "Effects of lenvatinib on tumor-associated macrophages enhance antitumor activity of PD-1 signal Inhibitors," Eisai Co., Ltd, poster, Nov. 6, 2015, 1 page.
Kharkyevitch, "Farmakologiya," Third ed (revised and supplemented), Moscow, "Meditsina," 1987, 5 pages (with English Translation).
"Molecular Targets and Cancer Therapeutics," Poster Session A. A92, Nov. 6, 2015, p. 64 (134 total pages).
Notice of Allowance in CA App Ser. No. 2676796, dated Oct. 8, 2015, 1 page.
Notice of Allowance in MK App. Ser. No. P/2015/231, dated Oct. 13, 2015, 2 pages (with English tmnslation).
Notice of Appeal, Pre-appeal Brief Request for Review and Petition for Extension of Time in U.S. Appl. No. 13/923,858, dated Nov. 25, 2015, 8 pages.
Office Action in AU App. Ser. No. 2011270165, dated Nov. 6, 2015, 3 pages.
Office Action in CA App. Ser. No. 2802644, dated Oct. 23, 2015, 6 pages.
Office Action in CA App. Ser. No. 2828946, dated Nov. 30, 2015, 4 pages.
Office Action in EP App. Ser. No. 12786619.2, dated Dec. 8, 2015, 4 pages.
Office Action in IL App. Ser. No. 217197, dated Oct. 25, 2015, 4 pages (with English translation).
Office Action in IL App. Ser. No. 238463, dated Oct. 28, 2015, 6 pages (with English translation).
Office Action in MX App. Ser. No. MX/a/2014/010594, dated Oct. 13, 2015, 8 pages (with English tmnslation).
Office Action in RU App. Ser. No. 2013140169, dated Nov. 6, 2015, 9 pages (with English translation).
Prior Art Submission and List of Corresponding Applications in IL App. Ser. No. 227558, dated Nov. 30, 2015, 3 pages (with English translation).
Rectification for a Voluntary Amendment in CN App. Ser. No. 201510031628.2, dated Oct. 10, 2015, 5 pages (with English translation).
Response filed in U.S. Appl. No. 10/797,903, dated Dec. 29, 2010, 13 pages.
Request for Examination and Voluntary Amendment in TH App. Ser. No. 0401005163, dated Aug. 21, 2015, 29 pages (with English translation).
Request to Enter PPH and Amended Claims in MX App. Ser. No. MX/a/2014/010594, dated Oct. 8, 2015, 10 pages (with English translation).
Response in AU App. Ser. No. 2011270165, dated Dec. 4, 2015, 5 pages.
Submission of Relevant Patent in MX App. Ser. No. MX/a/2014/010594, dated Sep. 24, 2015, 2 pages (with English translation).
Voluntary Amendment (Specification) in AU App. Ser. No. 2010285740, dated Nov. 20, 2015, 11 pages.

* cited by examiner

AMORPHOUS FORM OF QUINOLINE DERIVATIVE, AND METHOD FOR PRODUCING SAME

TECHNICAL FIELD

The present invention relates to an amorphous form of 4-(3-chloro-4-(cyclopropylaminocarbonyl)aminophenoxy)-7-methoxy-6-quinolinecarboxamide as well as a method for producing the same.

BACKGROUND ART

The compound 4-(3-chloro-4-(cyclopropylaminocarbonyl)aminophenoxy)-7-methoxy-6-quinolinecarboxamide is known to exhibit an excellent inhibiting effect on angiogenesis, and to be effective for prevention and treatment of tumors (Patent Literature 1). The compound has been reported as polymorphic crystals of the free form (Patent Literature 2), and as a crystalline or amorphous form of a methanesulfonate salt or an ethanesulfonate salt (Patent Literatures 3 and 4).

CITATION LIST

Patent Literature

Patent Literature 1: U.S. Patent Application Publication No. 2004/0053908
Patent Literature 2: U.S. Patent Application Publication No. 2007/0117842
Patent Literature 3: U.S. Patent Application Publication No. 2007/0078159
Patent Literature 4: U.S. Patent Application Publication No. 2007/0004773

SUMMARY OF INVENTION

Technical Problem

It is an object of the invention to provide a novel amorphous form of 4-(3-chloro-4-(cyclopropylaminocarbonyl)aminophenoxy)-7-methoxy-6-quinolinecarboxamide as well as a method for producing the same.

Solution to Problem

The invention provides the following [1] to [11].
[1] Amorphous 4-(3-chloro-4-(cyclopropylaminocarbonyl)aminophenoxy)-7-methoxy-6-quinolinecarboxamide.
[2] The amorphous compound according to [1], exhibiting a halo pattern without a distinct peak in X-ray powder diffraction.
[3] The amorphous compound according to [1] or [2], having peaks at chemical shifts of 158.1 ppm, 107.4 ppm, 56.3 ppm and 6.8 ppm in $^{13}$C solid nuclear magnetic resonance spectrum.
[4] A method for producing amorphous 4-(3-chloro-4-(cyclopropylaminocarbonyl)aminophenoxy)-7-methoxy-6-quinolinecarboxamide, comprising a step of dissolving 4-(3-chloro-4-(cyclopropylaminocarbonyl)aminophenoxy)-7-methoxy-6-quinolinecarboxamide crystals in a solvent.
[5] The method according to [4], further comprising a step of freeze-drying the solution of 4-(3-chloro-4-(cyclopropylaminocarbonyl)aminophenoxy)-7-methoxy-6-quinolinecarboxamide.
[6] The method according to [4] or [5], wherein the solvent is selected from the group consisting of water, an alcohol, an ether and acetonitrile, and a combination thereof
[7] The method according to [4] or [5], wherein the solvent is selected from the group consisting of water, a C1-6 alcohol and a combination thereof
[8] A pharmaceutical composition comprising an amorphous compound according to any one of [1] to [3].
[9] An antitumor agent comprising an amorphous compound according to any one of [1] to [3].
[10] The antitumor agent according to [9], wherein the tumor is thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.
[11] A metastasis inhibitor against tumor comprising an amorphous compound according to any one of [1] to [3].
[12] A method for preventing or treating a tumor, comprising administering a pharmacologically effective amount of an amorphous compound according to any one of [1] to [3] to a patient.
[13] The method according to [12], wherein the tumor is thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.
[14] A method for inhibiting tumor metastasis, comprising administering a pharmacologically effective amount of an amorphous compound according to any one of [1] to [3] to a patient.
[15] An amorphous compound according to any one of [1] to [3] for use in a method of preventing or treating a tumor.
[16] An amorphous compound according to [15], wherein the tumor is thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.
[17] An amorphous compound according to any one of [1] to [3] for use in a method of inhibiting metastasis of a tumor.
[18] Use of an amorphous compound according to any one of [1] to [3] for the manufacture of an antitumor agent.
[19] The use of an amorphous compound according to [18], wherein the tumor is thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.
[20] Use of an amorphous compound according to any one of [1] to [3] for the manufacture of a metastasis inhibitor against tumor.

Advantageous Effects of Invention

The amorphous 4-(3-chloro-4-(cyclopropylaminocarbonyl)aminophenoxy)-7-methoxy-6-quinolinecarboxamide of the invention has excellent solubility in water.

DESCRIPTION OF EMBODIMENTS

Figure 1:
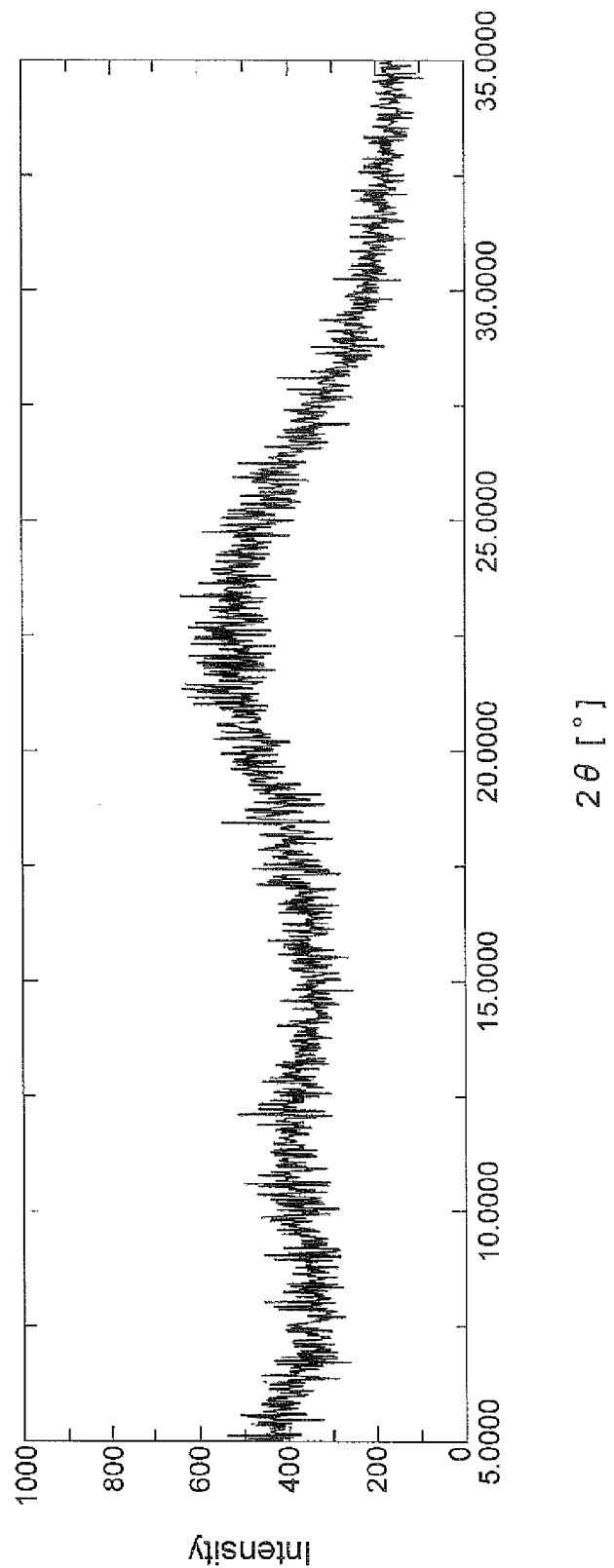
FIG. 1 is a diagram showing the X-ray powder diffraction pattern of the amorphous 4-(3-chloro-4-(cyclopropylaminocarbonyl)aminophenoxy)-7-methoxy-6-quinolinecarboxamide obtained in Example 1.

The amorphous 4-(3-chloro-4-(cyclopropylaminocarbonyl)aminophenoxy)-7-methoxy-6-quinolinecarboxamide of the invention (hereunder also referred to as "amorphous compound A") can be produced by the general production method described below, or by the method described in Example 1.

[General Production Method]

An amorphous form of 4-(3-chloro-4-(cyclopropylaminocarbonyl)aminophenoxy)-7-methoxy-6-quinolinecarboxamide of the invention (hereunder also referred to as "compound A") may be produced as amorphous compound A by mixing crystalline compound A and a solvent, and freeze-drying the solution. A portion of the solvent may also be distilled off before freeze-drying.

The crystalline compound A can be obtained by the method described in Patent Literature 1 or 2, for example, and it may be any desired crystal form or a mixture thereof.

The solvent used may be an alcohol including a C1-6 alcohol such as methanol, ethanol, 1-propanol, 2-propanol and tert-butyl alcohol, an ether such as tetrahydrofuran, acetonitrile, and/or water, with a C1-6 alcohol and water being preferred. These solvents may be used alone, or two or more thereof may be used in admixture.

The amount of solvent is not particularly restricted, but it may be 100 to 500 mL, preferably 150 to 300 mL and even more preferably 200 to 250 mL with respect to 1 g of compound A. When compound A is dissolved, it may be heated as appropriate. The temperature for heating will differ depending on the type of solvent but is not particularly restricted so long as it is below the boiling point of the solvent used, and it may be between 40° C. and the boiling point of the solvent, and preferably between 60° C. and the boiling point of the solvent.

There are no particular restrictions on the time required for freeze-drying, and it may be 6 to 168 hours, preferably 12 to 120 hours and more preferably 24 to 96 hours.

The amorphous compound of the invention exhibits a halo pattern without a distinct peak in X-ray powder diffraction. In other words, the amorphous compound of the invention does not have a sharp or definite diffraction peak in X-ray powder diffraction.

The amorphous compound of the invention has peaks at chemical shifts of 158.1 ppm, 107.4 ppm, 56.3 ppm and 6.8 ppm in $^{13}C$ solid NMR spectrum.

Since the chemical shift (ppm) in $^{13}C$ solid NMR spectrum is usually obtained with some degree of error, it is to be understood that the invention encompasses not only amorphous forms whose peaks (chemical shifts) in $^{13}C$ solid NMR spectrum completely match, but also amorphous forms having peaks with essentially equal chemical shifts when $^{13}C$ solid NMR spectrum is measured under ordinary measuring conditions or under essentially the same conditions as described in the present specification, and specifically it is interpreted as including values in a range of about ±0.5 ppm. Specifically, the invention includes not only amorphous forms whose peaks (chemical shifts) in the $^{13}C$ solid NMR spectrum completely match, but also amorphous forms whose peaks (chemical shifts) match within an error of about ±0.5 ppm.

The amorphous compound of the invention has potential for use as an antitumor agent for thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.

When the amorphous compound of the invention is to be administered as an antitumor agent, its dose may be appropriately selected according to the severity of symptoms, the age, gender, body weight and sensitivity of the patient, the administration route, the time of administration, the interval of administration and the type of pharmaceutical formulation. Normally, it will be 1-600 mg, preferably 5 to 400 mg and more preferably 5 to 200 mg per day, for oral administration to adults (60 kg body weight). It may be administered in 1 to 3 dosages per day.

When the amorphous compound of the invention is to be used as a medicament, it may be used as the drug substance itself or as a formulation of the drug substance prepared by a known method, such as a method described in the General Rules for Preparations in the Japanese Pharmacopeia, 15th Edition.

When the amorphous compound of the invention is to be formulated, it may be as granules, fine granules, tablets, capsules or the like. If necessary, a pharmacologically acceptable carrier may be added to the amorphous compound of the invention, and specifically, an excipient, binder, disintegrating agent, lubricant, antioxidant, corrigent, coloring agent, aromatic agent or the like may be added.

Examples of excipients include lactose, saccharose, glucose, fructose, starch, potato starch, corn starch, wheat starch, rice starch, crystalline cellulose, microcrystalline cellulose, powdered *glycyrrhiza*, mannitol, erythritol, maltitol, sorbitol, trehalose, silicic anhydride, calcium silicate, sodium hydrogencarbonate, calcium phosphate, anhydrous calcium phosphate, calcium sulfate and the like.

Examples of binders include gelatin, starch, gum Arabic, tragacanth, carboxymethyl cellulose, hydroxypropyl cellulose, hydroxypropyl methyl cellulose, polyvinylpyrrolidone, methyl cellulose, partially pregelatinized starch, pregelatinized starch, polyvinyl alcohol, sodium alginate, pullulan, glycerin and the like.

Disintegrating agents include corn starch, partially pregelatinized starch, hydroxypropyl starch, carmellose, carmellose sodium, carmellose calcium, carboxymethyl starch sodium, croscarmellose sodium, low-substituted hydroxypropyl cellulose, crospovidone and the like.

Examples of lubricants include magnesium stearate, stearic acid, calcium stearate, sodium stearyl fumarate, talc, macrogol and the like.

Examples of antioxidants include sodium ascorbate, L-cysteine, sodium sulfite, tocopherol, soybean lecithin and the like.

Examples of corrigents include citric acid, ascorbic acid, tartaric acid, malic acid, aspartame, acesulfame potassium, thaumatin, saccharin sodium, dipotassium glycyrrhizinate, sodium glutamate, sodium 5'-inosinate, sodium 5'-guanylate and the like.

Examples of coloring agents include titanium oxide, iron sesquioxide, yellow iron sesquioxide, cochineal, carmine, riboflavin, food Yellow No. 5, food Blue No. 2 and the like.

Examples of aromatic agents include lemon oil, orange oil, menthol, peppermint oil, borneol, vanilla flavor and the like.

EXAMPLES

The invention will now be explained in further detail by examples, with the understanding that the invention is not limited to these examples.

Example 1

Production of amorphous 4-(3-chloro-4-(cyclopropylaminocarbonyl)aminophenoxy)-7-methoxy-6-quinolinecarboxamide After measuring out 300 mg of B-form crystals of 4-(3-chloro-4-(cyclopropylaminocarbonyl)aminophenoxy)-7-methoxy-6-quinolinecarboxamide (Patent Literature 2), it was placed in a 200 mL-volume beaker and 40 mL of tert-butyl alcohol (tBA) was added. This was heated to boiling on a hot plate, and a suitable amount of tBA was added until dissolution of compound A, and then 10 mL of water was added. It was then heated mildly so that the solution did not boil, to prepare a sample solution. Finally the solvent volume was adjusted to 60 mL. A 200 mL-volume eggplant shaped flask was rotated while dipped in ethanol cooled with dry ice. The sample solution was added dropwise into the flask and frozen. After freezing the total amount of the sample solution, the orifice of the flask was wiped with a wiping cloth and freeze-drying was performed. This yielded 290 mg of amorphous compound A.

Test Example 1

Evaluation of Solubility

The dissolved concentration of amorphous compound A obtained in Example 1 was measured by the Paddle method. Approximately 40 mg of amorphous compound A was loaded into an equipment for the elution test, and 500 µL of solution was sampled at 5, 10, 20, 30, 45 and 60 minutes each. The concentration of compound A in the solution was measured by HPLC. As a comparative control there was used B-form crystals of 4-(3-chloro-4-(cyclopropylaminocarbonyl)aminophenoxy)-7-methoxy-6-quinolinecarboxamide (see Patent Literature 2).

[Conditions for Paddle Method]
Solvent: 100 mL of fasting artificial intestinal juice (buffer with pH 6.5, containing 29 mM $NaH_2PO_4$, 100 mM KCl, 7.5 mM lecithin, and 30 mM sodium taurocholate) Temperature: 37° C.
Paddle rotational speed: 50 rpm
[HPLC Conditions]
Column: YMC-UltraHT C18 (product of YMC Inc., inner diameter: 2.0 mm, column length: 50 mm, particle size: 2 µm)
Column temperature: 40° C. (using a column oven)
Flow rate: 0.42 mL/min
Mobile phase: Solution A and solution B were used for elution with the linear gradient shown in Table 1.
Solution A $H_2O:CH_3CN:HClO_4$*=990:10:1 (V/V/V)
Solution B $CH_3CN:H_2O:HClO_4$*=900:100:1 (V/V/V)
(*: 70% aqueous solution)
Injection volume: 10 µL
Detection: Ultraviolet absorptiometer (measuring wavelength: 252 nm).
Autosampler temperature: 10° C.

TABLE 1

| Time [minute] | Concentration of solution B [%] |
|---|---|
| 0 | 10 |
| 3.5 | 100 |
| 4 | 100 |

[Results]
The concentrations of compound A at each sampling time are shown in Table 2. At each sampling time, the concentration of compound A was 5.3 to 6.1 times higher when the amorphous compound was dissolved, than when the B-form crystal was dissolved.

TABLE 2

| Sampling time [minute] | Compound A Amorphous A [µg/mL] | Compound A Crystalline B [µg/mL] |
|---|---|---|
| 5 | 4.90 | 0.81 |
| 10 | 5.36 | 0.87 |
| 20 | 5.63 | 0.93 |
| 30 | 5.52 | 0.94 |
| 45 | 5.41 | 0.98 |
| 60 | 5.31 | 1.00 |

Test Example 2

X-Ray Powder Diffraction

X-ray powder diffraction of amorphous compound A was performed according to the procedure described in General Test Methods in the Japanese Pharmacopeia, 15th Edition (B-370-374).
[Measuring Conditions]
Apparatus: RINT-TTR-III (product of Rigaku Corp.)
X-rays: CuKα rays
Counter: Scintillation counter
Tube voltage: 50 kV
Tube current: 300 mA
Scan speed: 5°/min
Scanning axis: 2θ/θ
Scanning zone: 2θ=5°-35°
Divergence slit 0.5 mm
Scattering slit: open
Receiving slit: open The X-ray powder diffraction pattern for amorphous compound A is shown in FIG. 1. The amorphous compound A obtained in Example 1 exhibited a halo pattern without a distinct peak.

Test Example 3

Measurement of $^{13}C$ Solid NMR Spectrum

Figure 2:
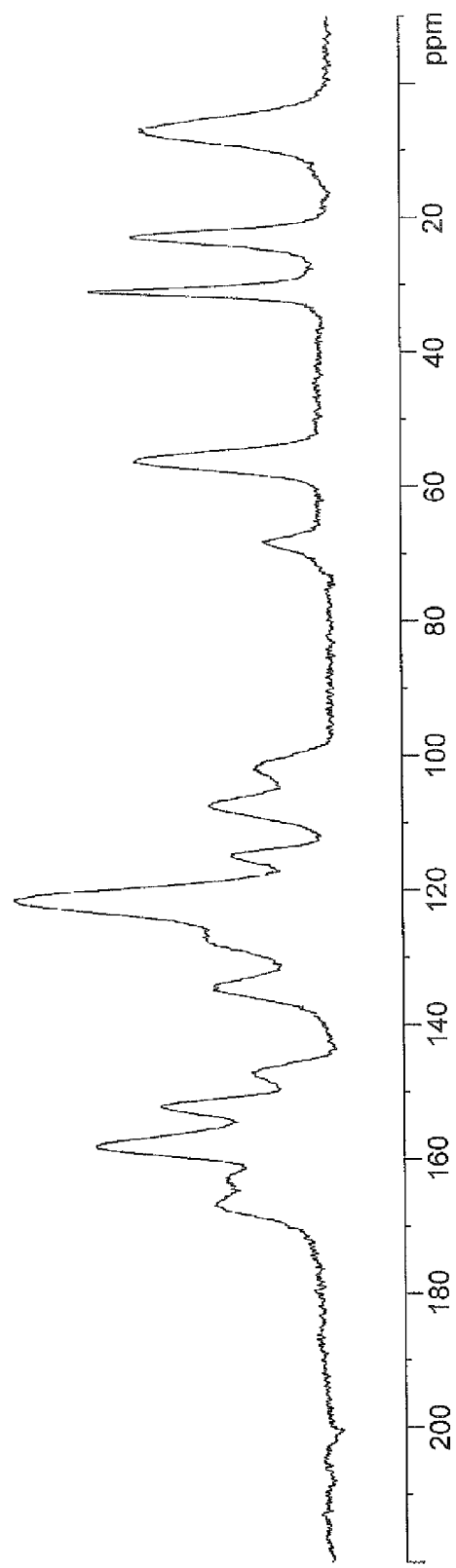
FIG. 2 is a diagram showing the $^{13}$C solid NMR spectrum of the amorphous 4-(3-chloro-4-(cyclopropylaminocarbonyl)aminophenoxy)-7-methoxy-6-quinolinecarboxamide obtained in Example 1.

The $^{13}C$ solid NMR spectrum of amorphous compound A was measured.
[Measuring Conditions]
Apparatus: AVANCE400 (manufactured by Bruker Corp.)
Measuring temperature: Room temperature (22° C.)
Reference material: Glycine (external reference: 176.03 ppm)
Measured nucleus: $^{13}C$ (100.6248425 MHz)
Pulse repetition time: 3 seconds
Pulse mode: TOSS The $^{13}C$ solid NMR spectrum for amorphous compound A is shown in FIG. 2, and the chemical shifts are shown in Table 3.

TABLE 3

| Chemical shift (ppm) |
|---|
| 166.9 |
| 162.7 |
| 158.1 |

TABLE 3-continued

| Chemical shift (ppm) |
|---|
| 152.2 |
| 147.1 |
| 134.8 |
| 127.0 |
| 121.4 |
| 115.0 |
| 107.4 |
| 102.0 |
| 68.3* |
| 56.3 |
| 31.1* |
| 22.9 |
| 6.8 |

*Peak for t-butyl alcohol

The invention claimed is:

1. Amorphous 4-(3-chloro-4-(cyclopropylaminocarbonyl)aminophenoxy)-7-methoxy-6-quinolinecarboxamide.

2. The amorphous compound according to claim 1, exhibiting a halo pattern without a distinct peak in X-ray powder diffraction.

3. The amorphous compound according to claim 1, having peaks at chemical shifts of 158.1 ppm, 107.4 ppm, 56.3 ppm and 6.8 ppm in $^{13}$C solid nuclear magnetic resonance spectrum.

4. A method for producing amorphous 4-(3-chloro-4-(cyclopropylaminocarbonyl)aminophenoxy)-7-methoxy-6-quinolinecarboxamide, comprising a step of dissolving 4-(3-chloro-4-(cyclopropylaminocarbonyl)aminophenoxy)-7-methoxy-6-quinolinecarboxamide crystals in a solvent.

5. The method according to claim 4, further comprising a step of freeze-drying the solution of 4-(3-chloro-4-(cyclopropylaminocarbonyl)aminophenoxy)-7-methoxy-6-quinolinecarboxamide.

6. The method according to claim 4, wherein the solvent is selected from the group consisting of water, an alcohol, an ether, acetonitrile, and a combination thereof.

7. The method according to claim 4, wherein the solvent is selected from the group consisting of water, a C1-6 alcohol and a combination thereof.

8. A pharmaceutical composition comprising the amorphous compound according to claim 1, and a pharmacologically acceptable carrier.

9. A method for treating a tumor, comprising administering a pharmacologically effective amount of the amorphous compound according to claim 1 to a patient in need thereof.

10. The method according to claim 9, wherein the tumor is thyroid cancer, uterine cancer, ovarian cancer, renal cell carcinoma, lung cancer, glioma, melanoma, hepatic cancer, gastric cancer, colorectal cancer, breast cancer, prostate cancer, brain tumor or blood tumor.

11. A method for inhibiting tumor metastasis, comprising administering a pharmacologically effective amount of the amorphous compound according to claim 1 to a patient in need thereof.

12. The amorphous compound according to claim 2, having peaks at chemical shifts of 158.1 ppm, 107.4 ppm, 56.3 ppm and 6.8 ppm in $^{13}$C solid nuclear magnetic resonance spectrum.

13. The method according to claim 5, wherein the solvent is selected from the group consisting of water, an alcohol, an ether, acetonitrile, and a combination thereof.

14. The method according to claim 5, wherein the solvent is selected from the group consisting of water, a C1-6 alcohol and a combination thereof.

15. A pharmaceutical composition comprising the amorphous compound according to claim 2, and a pharmacologically acceptable carrier.

16. A pharmaceutical composition comprising the amorphous compound according to claim 3, and a pharmacologically acceptable carrier.

17. A method for treating a tumor, comprising administering a pharmacologically effective amount of the amorphous compound according to claim 2 to a patient in need thereof.

18. A method for treating a tumor, comprising administering a pharmacologically effective amount of the amorphous compound according to claim 3 to a patient in need thereof.

19. A method for inhibiting tumor metastasis, comprising administering a pharmacologically effective amount of the amorphous compound according to claim 2 to a patient in need thereof.

20. A method for inhibiting tumor metastasis, comprising administering a pharmacologically effective amount of the amorphous compound according to claim 3 to a patient in need thereof.

21. The amorphous compound according to claim 1, having peaks at chemical shifts of 158.1±0.5 ppm, 107.4±0.5 ppm, 56.3±0.5 ppm and 6.8±0.5 ppm in $^{13}$C solid nuclear magnetic resonance spectrum.

22. The amorphous compound according to claim 2, having peaks at chemical shifts of 158.1±0.5 ppm, 107.4±0.5 ppm, 56.3±0.5 ppm and 6.8±0.5 ppm in $^{13}$C solid nuclear magnetic resonance spectrum.

23. The amorphous compound according to claim 1 prepared by a process comprising the step of freeze-drying a solution of 4-(3-chloro-4-(cyclopropylaminocarbonyl)aminophenoxy)-7-methoxy-6-quinolinecarboxamide.

* * * * *